(12) United States Patent
Xiong et al.

(10) Patent No.: US 12,102,633 B2
(45) Date of Patent: *Oct. 1, 2024

(54) SPIROLACTONE COMPOUNDS

(71) Applicant: Quixgen, Inc., North Brunswick, NJ (US)

(72) Inventors: Yusheng Xiong, Plainsboro, NJ (US); Hong-Ping Guan, Scotch Plains, NJ (US); Wenjun Huang, Doylestown, PA (US)

(73) Assignee: Quixgen, Inc., North Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/092,723

(22) Filed: Jan. 3, 2023

(65) Prior Publication Data

US 2023/0355609 A1 Nov. 9, 2023

Related U.S. Application Data

(63) Continuation of application No. 16/627,627, filed as application No. PCT/US2018/040328 on Jun. 29, 2018, now Pat. No. 11,541,046.

(Continued)

(51) Int. Cl.

| | | |
|---|---|---|
| *A61K 31/4709* | (2006.01) | |
| *A61K 9/00* | (2006.01) | |
| *A61K 31/145* | (2006.01) | |
| *A61K 31/18* | (2006.01) | |
| *A61K 31/192* | (2006.01) | |
| *A61K 31/197* | (2006.01) | |
| *A61K 31/203* | (2006.01) | |
| *A61K 31/40* | (2006.01) | |
| *A61K 31/401* | (2006.01) | |
| *A61K 31/4164* | (2006.01) | |
| *A61K 31/438* | (2006.01) | |
| *A61K 31/444* | (2006.01) | |
| *A61K 31/575* | (2006.01) | |
| *A61K 31/616* | (2006.01) | |
| *A61K 31/65* | (2006.01) | |
| *A61K 31/7048* | (2006.01) | |
| *A61K 31/7056* | (2006.01) | |
| *A61K 38/26* | (2006.01) | |
| *A61K 47/10* | (2017.01) | |
| *A61K 47/32* | (2006.01) | |

(Continued)

(52) U.S. Cl.
CPC ........ *A61K 31/4709* (2013.01); *A61K 9/0014* (2013.01); *A61K 31/145* (2013.01); *A61K 31/18* (2013.01); *A61K 31/192* (2013.01); *A61K 31/197* (2013.01); *A61K 31/203* (2013.01); *A61K 31/40* (2013.01); *A61K 31/401* (2013.01); *A61K 31/4164* (2013.01); *A61K 31/438* (2013.01); *A61K 31/444* (2013.01); *A61K 31/575* (2013.01); *A61K 31/616* (2013.01); *A61K 31/65* (2013.01); *A61K 31/7048* (2013.01); *A61K 31/7056* (2013.01); *A61K 38/26* (2013.01); *A61K 47/10* (2013.01); *A61K 47/32* (2013.01); *A61K 48/005* (2013.01); *A61P 1/16* (2018.01); *A61P 3/04* (2018.01); *A61P 17/10* (2018.01); *C07D 491/107* (2013.01); *C07D 519/00* (2013.01)

(58) Field of Classification Search
CPC ......... A61K 31/4709; A61P 3/04; A61P 17/10
See application file for complete search history.

(56) References Cited

U.S. PATENT DOCUMENTS

| | | |
|---|---|---|
| 3,686,186 A | 8/1972 | Houlihan |
| 5,536,716 A | 7/1996 | Chen |

(Continued)

FOREIGN PATENT DOCUMENTS

| | | |
|---|---|---|
| EP | 2123652 A1 | 11/2009 |
| RU | 2422446 C2 | 6/2011 |

(Continued)

OTHER PUBLICATIONS

Abu-Elheiga, L., et al. "Acetyl-CoA carboxylase 2 mutant mice are protected against obesity and diabetes induced by high-fat/high-carbohydrate diets." Proceedings of the National Academy of Sciences 100.18 (2003): 10207-10212.

(Continued)

*Primary Examiner* — Marcos L Sznaidman
(74) *Attorney, Agent, or Firm* — Quarles & Brady, LLP

(57) ABSTRACT

Provided herein are spirolactone compounds of Formula I that are useful as inhibitors of ACC1 and/or ACC2. The spirolactone compounds described herein can be used for treating a disease or disorder associated with aberrant ACC1 and/or ACC2 activities, for example, non-alcoholic steatohepatitis (NASH), acne, obesity, diabetes, and cancer. Also provided herein are pharmaceutical compositions comprising the spirolactone compound of Formula I, or pharmaceutically acceptable salt thereof.

Formula I

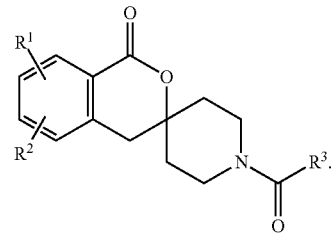

20 Claims, 1 Drawing Sheet

Related U.S. Application Data

(60) Provisional application No. 62/527,829, filed on Jun. 30, 2017.

(51) Int. Cl.
| | |
|---|---|
| *A61K 48/00* | (2006.01) |
| *A61P 1/16* | (2006.01) |
| *A61P 3/04* | (2006.01) |
| *A61P 17/10* | (2006.01) |
| *C07D 491/107* | (2006.01) |
| *C07D 519/00* | (2006.01) |

(56) References Cited

U.S. PATENT DOCUMENTS

| | | |
|---|---|---|
| 8,288,405 B2 | 10/2012 | Bagley |
| 8,884,034 B2 | 11/2014 | Daynard |
| 2011/0312952 A1 | 12/2011 | Lachance |
| 2012/0157432 A1 | 6/2012 | Edmondson |
| 2013/0303517 A1 | 11/2013 | Boyce |
| 2016/0220557 A1 | 8/2016 | Esler |

FOREIGN PATENT DOCUMENTS

| | | |
|---|---|---|
| WO | 2007011809 A1 | 1/2007 |
| WO | 2011025690 A1 | 3/2011 |

OTHER PUBLICATIONS

Abu-Elheiga, L., et al. "Continuous fatty acid oxidation and reduced fat storage in mice lacking acetyl-CoA carboxylase 2." Science 291.5513 (2001): 2613-2616.

Abu-Elheiga, L., et al. "Human acetyl-CoA carboxylase 2 molecular cloning, characterization, chromosomal mapping, and evidence for two isoforms." Journal of Biological Chemistry 272.16 (1997): 10669-10677.

Abu-Elheiga, L., et al. "Mutant mice lacking acetyl-CoA carboxylase 1 are embryonically lethal." Proceedings of the National Academy of Sciences 102.34 (2005): 12011-12016.

Abu-Elheiga, L., et al. "The subcellular localization of acetyl-CoA carboxylase 2." Proceedings of the National Academy of Sciences 97.4 (2000): 1444-1449.

Castle, J. C., et al. "ACC2 is expressed at high levels in human white adipose and has an isoform with a novel N-terminus [corrected]." PLoS One 4.2 (2009): e4369-e4369.

Gao, L., et al. "Simultaneous quantification of malonyl-CoA and several other short-chain acyl-CoAs in animal tissues by ion-pairing reversed-phase HPLC/MS." Journal of Chromatography B 853.1-2 (2007): 303-313.

Griffith, D. A., et al. "Decreasing the rate of metabolic ketone reduction in the discovery of a clinical acetyl-CoA carboxylase inhibitor for the treatment of diabetes." Journal of medicinal chemistry 57.24 (2014): 10512-10526.

Harriman, G., et al. "Acetyl-CoA carboxylase inhibition by ND-630 reduces hepatic steatosis, improves insulin sensitivity, and modulates dyslipidemia in rats." Proceedings of the National Academy of Sciences 113.13 (2016): E1796-E1805.

International Searching Authority, International Search Report and Written Opinion for application PCT/US2018/040328. Mailed on Sep. 24, 2018.

National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication No. 98-4083 (1998).

Svensson, R. U., et al. "Inhibition of acetyl-CoA carboxylase suppresses fatty acid synthesis and tumor growth of hon-small-cell lung cancer in preclinical models." Nature medicine 22.10 (2016): 1108.

Yamato M. et al. "Synthesis and Structure-Activity Relationship of Spiro[isochromanpiperidine] Analogues for Inhibition of Histamine Release," J. Med. Chem. 24:194-198 (1981).

Zaenglein, A. L., et al. "Guidelines of care for the management of acne vulgaris." Journal of the American Academy of Dermatology 74.5 (2016): 945-973.

Zhang, H., et al. "Crystal structure of the carboxyltransferase domain of acetyl-coenzyme A carboxylase." Science 299.5615 (2003): 2064-2067.

Zouboulis, C. C. et al., "A new concept for acne therapy: a pilot study with zileuton, an oral 5-lipoxygenase inhibitor", Arch. Dermatol. (2003), vol. 139, pp. 668-670.

Zouboulis, C. C. et al., "Zileuton, an oral 5-lipoxygenase inhibitor, directly reduces sebum production", Dermatology (2005), vol. 210, pp. 36-38.

European Patent Office. Extended European Search Report for application 18824003.0. Mailed on Nov. 2, 2020. 7 pages.

Hashigaki, K., et al. "Synthesis and Structure-Activity Relationship of Spiro [isochroman-piperidine] Analogs for Inhibition of Histamine Release. IV." Chemical and pharmaceutical bulletin 32.9 (1984): 3561-3568.

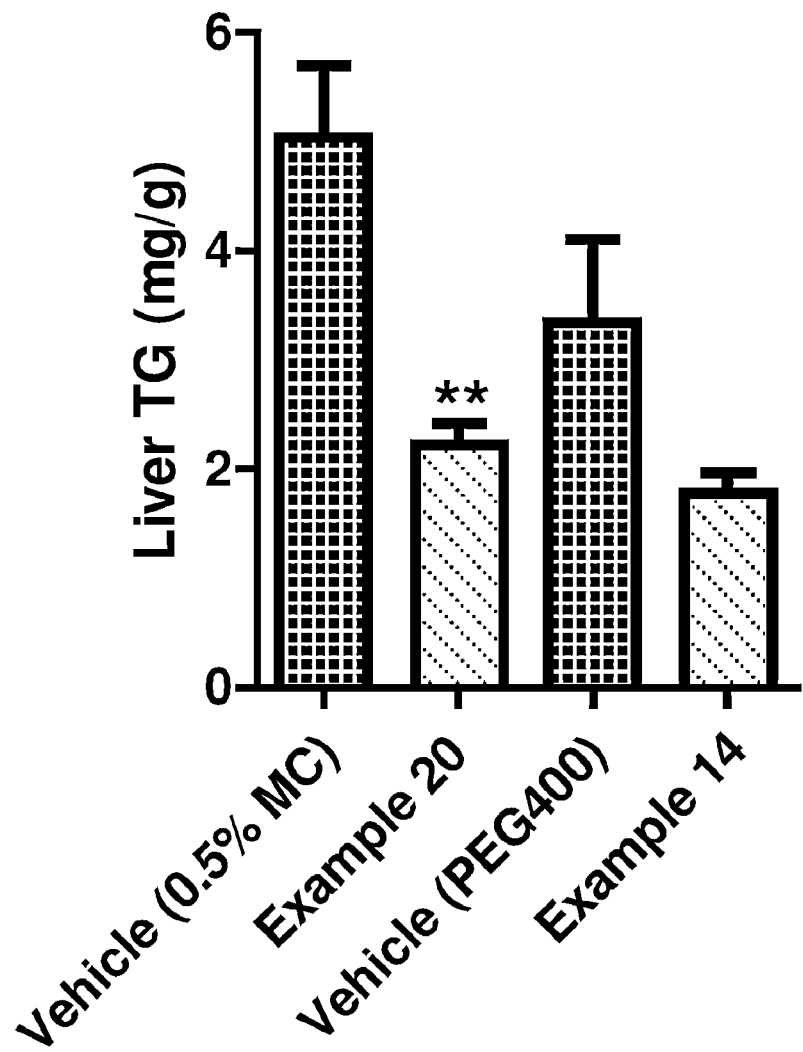

SPIROLACTONE COMPOUNDS

CROSS REFERENCE TO RELATED APPLICATIONS

This application is a continuation of U.S. patent application Ser. No. 16/627,627, filed Dec. 30, 2019, issued on Jan. 3, 2023 as U.S. Pat. No. 11,541,046, which is a national stage filing under 35 U.S.C. § 371 of International Patent Application No. PCT/US2018/040328, filed Jun. 29, 2018, which claims benefit of priority of U.S. Provisional Patent Application No. 62/527,829, filed on Jun. 30, 2017, all of which are incorporated herein by reference in their entirety.

BACKGROUND OF THE INVENTION

Field of the Invention

In various embodiments, the present invention is generally related to a novel class of spirolactone compounds, salts thereof, pharmaceutical compositions comprising the same, synthetic methods thereof, and uses thereof.

Background Art

Fatty acids are essential components for normal function of living cells including membrane biosynthesis, the production of signaling lipids, post-translational modifications, energy production and storage, etc. Acetyl-CoA carboxylase (ACC) is a cytoplasmic enzyme catalyzing the conversion of acetyl-CoA to malonyl-CoA, the rate-limiting step for fatty acid metabolism in cells. Cytoplasmic malonyl-CoA controls two downstream pathways of lipid metabolism, de novo fatty acid synthesis and fatty acid β-oxidation. Malonyl-CoA is the building block for long chain fatty acids synthesis and elongation. Malonyl-CoA can also allosterically inhibit the fatty acid transporter on mitochondrial membrane, carnitine palmitoyltransferase-1, and block the entry of fatty acyl-CoA into mitochondria. By inhibiting ACC, cellular long chain fatty acid synthesis can be blocked and β-oxidation can be stimulated in the mitochondria. As a result, cellular lipid contents are reduced.

ACC has two isoforms, ACC1 and ACC2, localized in cytosol and mitochondrial membrane respectively. ACC protein is composed of three domains, in which biotin carboxylase domain catalyzes the carboxylation of biotin that is covalently linked to the biotin carboxyl carrier protein domain, and the carboxyltransferase domain catalyzes the transfer of the carboxyl group from carboxyl biotin to acetyl-CoA (Zhang et al., Science 299:2064-2067 (2003)). Molecular masses of ACC1 and ACC2 are about 265 and about 280 kDa respectively. Although both isoforms are found in different tissues, ACC1 is mainly expressed in lipogenic tissues such as liver, adipose, and lactating mammary gland, and ACC2 is predominantly expressed in muscle tissues and heart. In rodents, ACC1 is mainly responsible for de novo fatty acid synthesis and ACC2 for fatty acid beta-oxidation (Abu-Elheiga et al., The Journal of biological chemistry 272:10669-10677 (1997); Abu-Elheiga et al., Proceedings of the National Academy of Sciences of the United States of America 92:4011-4015(1995)). In humans, ACC2 isoforms are also abundantly expressed in adipose tissue and liver and capable of de novo lipogenesis in these tissues (Castle et al., PloS one 4:e4369(2009)). Genetic studies show that ACC1 is essential for development and ACC1 deficiency causes embryonic lethality (Abu-Elheiga et al., Proceedings of the National Academy of Sciences of the United States of America 97:1444-1449(2000)). In contrast, ACC2 mutant mice live and breed normally although they are leaner due to increased fatty acid oxidation, and resistant to high-fat high-carbohydrate diets in terms of body weight gain and insulin resistance (Abu-Elheiga et al., Science 291:2613-2616(2001); Abu-Elheiga et al., Proceedings of the National Academy of Sciences of the United States of America 102:12011-12016(2005); Abu-Elheiga et al., Proceedings of the National Academy of Sciences of the United States of America 100:10207-10212(2003)).

Various diseases or disorders are associated with aberrant ACC1 and/or ACC2 activities. Accordingly, there is a need for novel compounds that can modulate ACC1 and/or ACC2 activities.

BRIEF SUMMARY OF THE INVENTION

In various embodiments, the present disclosure provides a spirolactone compound that can be an inhibitor of ACC1 and/or ACC2, or a pharmaceutically acceptable salt thereof. In some embodiments, the present disclosure also provides pharmaceutical compositions comprising the spirolactone compound or pharmaceutically acceptable salt thereof. In some embodiments, the present disclosure also provides methods of using the spirolactone compound or pharmaceutically acceptable salt thereof for treating a disease or disorder associated with aberrant ACC1 and/or ACC2 activities, for example, non-alcoholic steatohepatitis (NASH), acne, obesity, diabetes, and cancer.

Certain embodiments of the present disclosure are directed to a compound of Formula I or a pharmaceutically acceptable salt thereof:

Formula I

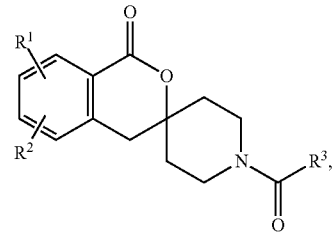

wherein $R^1$, $R^2$ and $R^3$ are defined herein. In some embodiments, the compound of Formula I is a compound of Formula I-1, Formula Ia, Formula Ib, Formula Ic, Formula II-1 to II-3, or Formula III-1 to III-6 as defined herein. In any of the embodiments described herein, the spirolactone compound can be 1'-(4,8-dimethoxy-2-naphthoyl)-7-isopropyl-spiro[isochroman-3,4'-piperidin]-1-one (Example 1), 1'-(4,8-dimethoxyquinoline-2-carbonyl)-7-isopropylspiro[isochroman-3,4'-piperidin]-1-one (Example 2), 1'-(4,8-dimethoxy-2-naphthoyl)-7-ethylspiro[isochroman-3,4'-piperidin]-1-one (Example 3), 1'-(4,8-dimethoxyquinoline-2-carbonyl)-7-ethylspiro[isochroman-3,4'-piperidin]-1-one (Example 4), 1'-(4,8-dimethoxy-2-naphthoyl)-7-((1-methyl-1H-pyrazol-5-yl)amino)spiro[isochroman-3,4'-piperidin]-1-one (Example 5), 1'-(4,8-dimethoxyquinoline-2-carbonyl)-7-((1-methyl-1H-pyrazol-5-yl)amino)spiro[isochroman-3,4'-piperidin]-1-one (Example 6), 7-isopropyl-1'-(2-methyl-1H-benzo[d]imidazole-6-carbonyl)spiro[isochroman-3,4'-piperidin]-1-one (Example 7), 1'-(1H-indazole-5-carbonyl)-7-isopropylspiro[isochroman-3,4'-piperidin]-1-one (Example 8), 7-isopropyl-1'-(1H-pyrrolo[3,2-b]pyridine-2-carbonyl)-spiro[isochroman-3,4'-piperidin]-1-one (Example 9), 1'-(1H-indazole-6-carbonyl)-7-isopropylspiro-[isochroman-3,4'-piperidin]-1-one (Example 10), 7-isopropyl-1'-(6-methoxyquinoline-3-carbonyl)spiro [isochroman-3,4'-piperidin]-1-one (Example 11), 1'-(2-ethyl-1H-benzo[d]imidazole-6-carbonyl)-7-isopropylspiro[isochroman-3,4'-piperidin]-1-one (Example 12), 7-isopropyl-1'-(3-methyl-2-oxo-2,3-dihydro-1H-benzo [d]imidazole-5-carbonyl)spiro [isochroman-3,4'-piperidin]-1-one (Example 13), methyl 5-(1'-(4,8-dimethoxyquinoline-2-carbonyl)-1-oxospiro[isochroman-3,4'-piperidin]-7-yl)nicotinate (Example 14), 5-(1'-(4,8-dimethoxyquinoline-2-carbonyl)-1-oxospiro [isochroman-3,4'-piperidin]-7-yl)nicotinic acid (Example 15), 1-((ethoxycarbonyl)oxy)ethyl 5-(1'-(4,8-dimethoxy-quinoline-2-carbonyl)-1-oxospiro[isochroman-3,4'-piperidin]-7-yl)nicotinate (Example 16), 2-(2-(2-methoxyethoxy)ethoxy) ethyl 5-(1'-(4,8-dimethoxyquinoline-2-carbonyl)-1-oxospiro[isochroman-3,4'-piperidin]-7-yl)nicotinate (Example 17), 2-(2-methoxyethoxy)ethyl 5-(1'-(4,8-dimethoxy-quinoline-2-carbonyl)-1-oxospiro[isochroman-3,4'-piperidin]-7-yl)nicotinate (Example 18), methyl 5-(1'-(8-cyclopropyl-4-methoxyquinoline-2-carbonyl)-1-oxospiro [isochroman-3,4'-piperidin]-7-yl)nicotinate (Example 19), 5-(1'-(8-cyclopropyl-4-methoxyquinoline-2-carbonyl)-1-oxospiro[isochroman-3,4'-piperidin]-7-yl)nicotinic acid (Example 20), methyl 5-(1'-(1-cyclopropyl-4-methoxy-3-methyl-1H-indole-6-carbonyl)-1-oxospiro[isochroman-3,4'-piperidin]-7-yl)nicotinate (Example 21), or 5-(1'-(1-cyclopropyl-4-methoxy-3-methyl-1H-indole-6-carbonyl)-1-oxospiro [isochroman-3,4'-piperidin]-7-yl)nicotinic acid (Example 22), or a pharmaceutically acceptable salt thereof.

Certain embodiments of the present disclosure are directed to a pharmaceutical composition comprising a spirolactone compound of Formula I (e.g., a compound of Formula I-1, Formula Ia, Formula Ib, Formula Ic, Formula II-1 to II-3, or Formula III-1 to III-6, or any of Examples 1-22) as defined herein, or a pharmaceutically acceptable salt thereof. In some embodiments, the pharmaceutical composition further comprises one or more additional active agents.

The pharmaceutical composition described herein can be formulated for different routes of administration. In some embodiments, the pharmaceutical composition can be formulated for intravenous injection or infusion, oral administration, inhalation, or topical administration. In some embodiments, the pharmaceutical composition can be formulated in the form of a topical solution, lotion, shampoo, transdermal spray, topical film, foam, powder, paste, sponge, transdermal patch, tincture, tape, cream, gel, or ointment.

Certain embodiments of the present disclosure are directed to a method of inhibiting ACC1 and/or ACC2 activities in a cell. In some embodiments, the method comprises contacting the cell with a spirolactone compound described herein or pharmaceutically acceptable salts thereof, or a pharmaceutical composition described herein.

In some embodiments, the present disclosure also provides a method of inhibiting malonyl-CoA production, lipogenesis in a cell (e.g., a sebocyte, an adipocyte, or a hepatocyte), proliferation of cells (e.g., sebocytes, keratinocytes, adipocytes, melanocytes, squamous cells, Merkel cells, Langerhans cells, or skin stem cells, e.g., in epidermis, dermis, and/or hypodermis), differentiation of fibroblast to adipocytes, sebum production, or a combination thereof, in a subject in need thereof. In some embodiments, the subject is characterized as having a disease or disorder chosen from acne, seborrhea, sebaceous hyperplasia, seborrheic keratosis, sebaceous adenoma, sebaceous cyst, actinic keratosis, sebaceous carcinoma, squamous cell carcinoma, melanoma, phymatous rosacea, fibrofolliculomas in Birt-Hogg-Dube syndrome, and combinations thereof. In some embodiments, the subject is characterized as having nonalcoholic steatohepatitis (NASH). In some embodiments, the method comprises administering to the subject an effective amount of a spirolactone compound described herein or pharmaceutically acceptable salts thereof, or a pharmaceutical composition described herein.

Certain embodiments of the present disclosure are directed to a method of treating a disease or disorder associated with ACC1 and/or ACC2 in a subject in need thereof. In some embodiments, the method comprises administering to the subject in need thereof a therapeutically effective amount of a spirolactone compound described herein (e.g., a compound of Formula I, Formula I-1, Formula Ia, Formula Ib, Formula Ic, Formula II-1 to II-3, or Formula III-1 to III-6, or any of Examples 1-22), or a pharmaceutically acceptable salt thereof, or a pharmaceutical composition described herein. In some embodiments, the method further comprises treating the subject in need thereof with one or more additional therapies for the respective disease or disorder (e.g., as described herein). Non-limiting diseases or disorders suitable to be treated with the methods described herein include a skin disease, such as a disease or disorder associated with aberrant sebocyte and/or keratinocyte activities (e.g., acne), a non-alcoholic fatty liver disease (such as nonalcoholic steatohepatitis (NASH)), a metabolic disease or disorder (e.g., obesity or diabetes), and cancer.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention.

FIG. 1 presents bar graphs showing that chronic treatment with ACC inhibitors (e.g., Example 14 or 20) reduced liver triglycerides (TG) in C57BL/6J mice. Data were represented as mean±SEM. Statistical significance was determined by using ANOVA analysis, ** $p<0.01$ relative to vehicle.

DETAILED DESCRIPTION OF THE INVENTION

The present disclosure is generally related to novel class of spirolactone compounds that can be used as an ACC inhibitor (ACC1 and/or ACC2 inhibitor). In various embodiments, the present disclosure provides compounds, pharmaceutical compositions, methods, and uses related to the novel spirolactone compounds described herein.

Spirolactone Compounds

Certain embodiments of the present disclosure are directed to novel spirolactone compounds. In some embodiment, the present disclosure provides a compound of Formula I, or a pharmaceutically acceptable salt thereof,

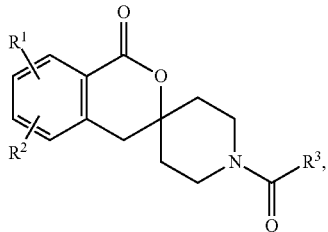

Formula I wherein:
R¹ and R² are each independently hydrogen, halogen, cyano, an optionally substituted alkyl (e.g., an optionally substituted C$_{1-6}$ alkyl), an optionally substituted cycloalkyl (e.g., an optionally substituted C$_{3-6}$ cycloalkyl), an optionally substituted alkenyl (e.g., an optionally substituted C$_{2-6}$ alkenyl), an optionally substituted alkynyl (e.g., an optionally substituted C$_{2-6}$ alkynyl), an optionally substituted aryl (e.g., an optionally substituted C$_{6-10}$ aryl), an optionally substituted heteroaryl (e.g., an optionally substituted 5-10 membered heteroaryl), an optionally substituted heterocyclyl (e.g., an optionally substituted 4-6 membered heterocyclyl), NR$^{10}$R$^{11}$, COOR$^{12}$, CONR$^{13}$R$^{14}$, CN, S(O)$_n$R$^{15}$, or OR$^{16}$;

wherein
R$^{10}$ and R$^{11}$ are each independently hydrogen, an optionally substituted alkyl (e.g., an optionally substituted C$_{1-6}$ alkyl), an optionally substituted cycloalkyl (e.g., an optionally substituted C$_{3-6}$ cycloalkyl), an optionally substituted alkanoyl (e.g., an optionally substituted C$_{1-6}$ alkanoyl), an optionally substituted cycloalkanoyl (e.g., an optionally substituted C$_{3-6}$ cycloalkanoyl), an optionally substituted aryl (e.g., an optionally substituted C$_{6-10}$ aryl), an optionally substituted heteroaryl (e.g., an optionally substituted 5-10 memberedheteroaryl), an optionally substituted heterocyclyl (e.g., an optionally substituted 4-6 membered heterocyclyl), COOR², or CONR$^{13}$R$^{14}$; R$^{12}$, R$^{13}$ and R$^{14}$ are each independently hydrogen or an optionally substituted alkyl (e.g., an optionally substituted C$_{1-6}$ alkyl);

n is 0, 1, or 2;

R$^{15}$ is an optionally substituted alkyl (e.g., an optionally substituted C$_{1-6}$ alkyl), an optionally substituted cycloalkyl (e.g., an optionally substituted C$_{3-6}$ cycloalkyl), or NR$^{10}$R$^{11}$;

R$^{16}$ is hydrogen, an optionally substituted alkyl (e.g., an optionally substituted C$_{1-6}$ alkyl), an optionally substituted cycloalkyl (e.g., an optionally substituted C$_{3-6}$ cycloalkyl), an optionally substituted alkanoyl (e.g., an optionally substituted C$_{1-6}$ alkanoyl), an optionally substituted cycloalkanoyl (e.g., an optionally substituted C$_{3-6}$ cycloalkanoyl), an optionally substituted aryl (e.g., an optionally substituted C$_{6-10}$ aryl), an optionally substituted heteroaryl (e.g., an optionally substituted 5-10 memberedheteroaryl), an optionally substituted heterocyclyl (e.g., an optionally substituted 4-6 membered heterocyclyl) or CONR$^{13}$R$^{14}$;

and R³ is an optionally substituted aryl (e.g., an optionally substituted C$_{6-10}$ aryl) or an optionally substituted heteroaryl (e.g., an optionally substituted 5-10 membered heteroaryl), provided that when R¹ and R² are both hydrogen, then R³ is not an optionally substituted phenyl.

In some embodiments, both R¹ and R² are hydrogen, provided that R³ is not an optionally substituted phenyl. In some embodiments, only one of R¹ and R² is hydrogen, i.e., the phenyl ring in Formula I is monosubstituted. In some embodiments, neither of R¹ and R² is hydrogen, i.e., the phenyl ring in Formula I is disubstituted.

In some preferred embodiments, the compound of Formula I is a compound of Formula I-1:

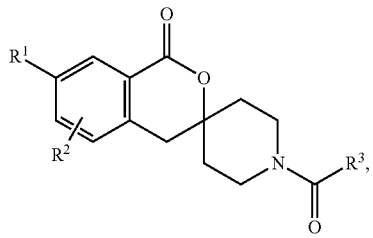

Formula I-1 wherein R¹, R² and R³ are as defined herein. In some embodiments, R¹ is not hydrogen. In some embodiments, R¹ is hydrogen.

In any of the embodiments described herein, R² can be hydrogen. For example, in some embodiments, the compound of Formula I is a compound of Formula Ia.

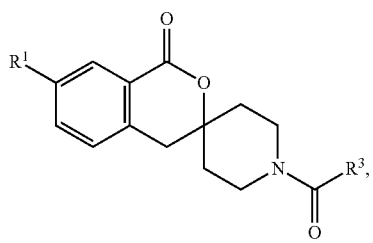

Formula Ia wherein R¹ and R³ are as defined herein. In some embodiments, R¹ is not hydrogen. In some embodiments, R¹ is hydrogen.

In some embodiments, R¹ is a halogen, such as F, Cl, Br, or I. In some embodiments, R¹ is CN. When R¹ is a halogen, the compound of Formula I (e.g., a compound of Formula Ia) can also serve as a synthetic intermediate for the synthesis of other compounds, such as compounds of Formula I wherein R¹ is an optionally substituted alkyl, an optionally substituted cycloalkyl, an optionally substituted aryl, an optionally substituted heteroaryl, an optionally substituted heterocyclyl, NR¹R$^{11}$, COOR$^{12}$, CONR$^{13}$R$^{14}$, CN, S(O)$_n$R¹s, or OR$^{16}$, through a coupling reaction (e.g., a palladium mediated or copper mediated coupling reaction).

In some embodiments, R¹ is an optionally substituted alkyl. In some embodiments, R¹ is an optionally substituted C$_{1-6}$ alkyl. In some preferred embodiments, R¹ is an optionally substituted C$_{1-4}$ alkyl. For example, in some embodiments, R¹ can be a C$_{1-4}$ alkyl (e.g., methyl, ethyl, isopropyl, sec-butyl, tert-butyl). In some embodiments, R¹ can be a C$_{1-4}$ alkyl optionally substituted with one or more (e.g., 1-3) substituents independently chosen from halogen (e.g., F) and C$_{1-4}$ alkyl. For example, R¹ can be a C$_{1-4}$ alkyl optionally substituted with 1-3 fluorines, such as CF$_3$, CF$_3$CH$_2$, etc.

In some embodiments, $R^1$ is an optionally substituted alkoxy. In some embodiments, $R^1$ is an optionally substituted $C_{1-6}$ alkoxy. In some preferred embodiments, $R^1$ is an optionally substituted $C_{1-4}$ alkoxy. For example, $R^1$ can be a $C_{1-4}$ alkoxy (e.g., methoxy, ethoxy, isopropoxy, sec-butoxy, tert-butoxy). In some embodiments, $R^1$ can be a $C_{1-4}$ alkoxy optionally substituted with one or more (e.g., 1-3) substituents independently chosen from halogen (e.g., F) and $C_{1-4}$ alkyl. For example, $R^1$ can be a $C_{1-4}$ alkoxy optionally substituted with 1-3 fluorines, such as $CF_3O$, $CF_3CH_2O$, etc.

In some embodiments, $R^1$ is an optionally substituted cycloalkyl. In some embodiments, $R^1$ is an optionally substituted $C_{3-6}$ cycloalkyl. In some embodiments, $R^1$ is a $C_{3-6}$ cycloalkyl. In some embodiments, $R^1$ is a $C_{3-6}$ cycloalkyl, optionally substituted with one or more (e.g., 1-3) substituents independently chosen from halogen (e.g., F) and $C_{1-4}$ alkyl. For example, in some embodiments, $R^1$ is cyclopropyl or cyclobutyl. In some embodiments, $R^1$ is cyclopropyl or cyclobutyl, optionally substituted with 1-3 fluorines.

In some embodiments, $R^1$ is an optionally substituted cycloalkoxy. In some embodiments, R is an optionally substituted $C_{3-6}$ cycloalkoxy. In some embodiments, R is a $C_{3-6}$ cycloalkoxy. In some embodiments, $R^1$ is a $C_{3-6}$ cycloalkoxy, optionally substituted with one or more (e.g., 1-3) substituents independently chosen from halogen (e.g., F) and $C_{1-4}$ alkyl. For example, in some embodiments, $R^1$ is cyclopropoxy or cyclobutoxy. In some embodiments, $R^1$ is cyclopropoxy or cyclobutoxy, optionally substituted with 1-3 fluorines.

In some preferred embodiments, $R^1$ is halogen, an optionally substituted $C_{1-6}$ alkyl, an optionally substituted $C_{1-6}$ alkoxy, an optionally substituted $C_{3-6}$ cycloalkyl, or an optionally substituted $C_{3-6}$ cycloalkoxy. In some preferred embodiments, $R^1$ is $C_{1-4}$ alkyl, $C_{1-4}$ alkoxy, $C_{3-6}$ cycloalkyl, or $C_{3-6}$ cycloalkoxy, each optionally substituted with 1-3 substituents independently chosen from halogen and $C_{1-4}$ alkyl. In some preferred embodiments, R is $C_{1-4}$ alkyl or $C_{1-4}$ alkoxy, each optionally substituted with 1-3 fluorines.

In some embodiments, $R^1$ is an optionally substituted aryl, such as optionally substituted $C_{6-12}$ aryl (e.g., phenyl). In some embodiments, $R^1$ is a $C_{6-12}$ aryl (e.g., phenyl) optionally substituted with one or more (e.g., 1 or 2) substituents independently chosen from halogen, hydroxyl, cyano, optionally substituted $C_{1-4}$ alkyl, optionally substituted $C_{1-4}$ alkoxy, optionally substituted $C_{3-6}$ cycloalkyl, and optionally substituted $C_{3-6}$ cycloalkoxy. In some embodiments, $R^1$ is a $C_{6-12}$ aryl (e.g., phenyl) optionally substituted with one or more (e.g., 1 or 2) substituents independently chosen from halogen (e.g., F, Cl), cyano, $C_{1-4}$ alkyl, $C_{1-4}$ alkoxy, $C_{3-6}$ cycloalkyl, and $C_{3-6}$ cycloalkoxy, wherein each of the alkyl, alkoxy, cycloalkyl, and cycloalkoxy is optionally substituted with one to three substituents independently chosen from halogen (e.g., F) and $C_{1-4}$ alkyl.

In some embodiments, $R^1$ is an optionally substituted heteroaryl. For example, in some embodiments, $R^1$ is a 5-10 membered heteroaryl (e.g., a 5 or 6 membered heteroaryl as described herein) optionally substituted with one or more (e.g., 1 or 2) substituents independently chosen from halogen, cyano, optionally substituted $C_{1-4}$ alkyl, optionally substituted $C_{1-4}$ alkoxy, optionally substituted $C_{3-6}$ cycloalkyl, and optionally substituted $C_{3\_6}$ cycloalkoxy. In some embodiments, $R^1$ is a 5-10 membered heteroaryl (e.g., a 5 or 6 membered heteroaryl as described herein) optionally substituted with one or more (e.g., 1 or 2) substituents independently chosen from halogen (e.g., F, Cl), cyano, $C_{1-4}$ alkyl, $C_{1-4}$ alkoxy, $C_{3-6}$ cycloalkyl, and $C_{3-6}$ cycloalkoxy, wherein each of the alkyl, alkoxy, cycloalkyl, and cycloalkoxy is optionally substituted with one to three substituents independently chosen from halogen (e.g., F) and $C_{1-4}$ alkyl.

In some embodiments, $R^1$ can be a 5-10 membered heteroaryl (e.g., a 5 or 6 membered heteroaryl as described herein, such as tetrazolyl, pyridinyl etc.) optionally substituted with one or more (e.g., 1 or 2) substituents independently chosen from halogen, hydroxyl, cyano, $COOR^{12}$, wherein $R^{12}$ is hydrogen or an optionally substituted $C_{1-6}$ alkyl, optionally substituted $C_{1-4}$ alkyl, optionally substituted $C_{1-4}$ alkoxy, optionally substituted $C_{3-6}$ cycloalkyl, and optionally substituted $C_{3-6}$ cycloalkoxy. In some embodiments, R can be an optionally substituted pyridinyl (e.g., 2-, 3-, or 4-pyridinyl). In some embodiments, the pyridinyl can be optionally substituted with one or more (e.g., 1 or 2) substituents independently chosen from halogen, hydroxyl, cyano, $COOR^{12}$, wherein $R^{12}$ is hydrogen or an optionally substituted $C_{1-6}$ alkyl, optionally substituted $C_{1-4}$ alkyl, optionally substituted $C_{1-4}$ alkoxy, optionally substituted $C_{3-6}$ cycloalkyl, and optionally substituted $C_{3-6}$ cycloalkoxy. In some embodiments, the pyridinyl can be substituted with $COOR^{12}$ (e.g., COOH). In some embodiments, the pyridinyl can be substituted with COOH or a group that can be converted into a carboxylic acid group (or salt thereof) in vivo. Suitable groups that can be converted into a carboxylic acid group (or salt thereof) in vivo include those known in the art, for example, esters, amides, and the like. Without wishing to be bound by theories, it is believed that the carboxylic acid functional group, such as a pyridinyl carboxylic acid, can help targeted delivery of a compound to liver and thus can be particularly useful for treating a liver disease (e.g., NASH), e.g., with a reduced required systemic exposure.

In some embodiments, $R^1$ can be an optionally substituted 3-pyridinyl. For example, in some embodiments, the compound of Formula I can be a compound of Formula Ic:

Formula Ic

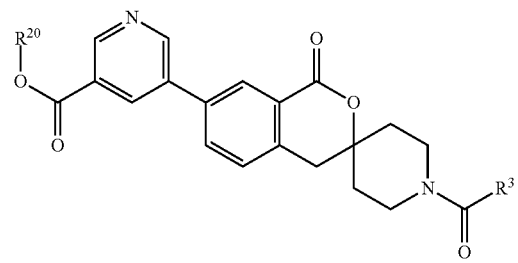

wherein $R^3$ and $R^{20}$ are as defined herein. Suitable $R^{20}$ for compound of Formula Ic include any of those groups wherein the group $COOR^{20}$ is COOH (or salt thereof) or can be converted into COOH (or salt thereof) in vivo. In some embodiments, $R^{20}$ can be hydrogen, an optionally substituted alkyl, or an optionally substituted cycloalkyl (e.g., an optionally substituted $C_{3-6}$ cycloalkyl). In some embodiments, $R^{20}$ can be an optionally substituted $C_{1-6}$ alkyl (e.g., an optionally substituted $C_{1-4}$ alkyl). In some embodiments, $R^{20}$ can be hydrogen or an optionally substituted $C_{1-4}$ alkyl (e.g., methyl, ethyl etc.). Various substituent(s) for the alkyl or cycloalkyl can be used, which include any of those that do not prevent the conversion of the ester group into a carboxylic acid group (or salt thereof) in vivo. However, preferably, the $R^{20}$ group (including any substituent(s)) is selected such that compound of Formula Ic or the resulting cleavage byproduct (i.e., not the spirolactone product produced) is of no or acceptable toxicity to a subject user at therapeutically effective dose. In some embodiments, the group COOR$^{20}$ can be a simple alkyl ester (e.g., methyl, ethyl, or other C$_{1-4}$ alkyl ester).

In some embodiments, R$^{20}$ can include an oligo- or polyethylene glycol chain. For example, in some embodiments, R$^2$ can be

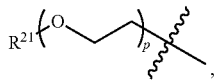

wherein p is an integer from 1-500 (e.g., 1-10, 1-50, 1-100, etc., for example, 1, 2, or 3), and R$^{21}$ is hydrogen, C$_{1-4}$ alkyl (e.g., methyl), or an oxygen protecting group. Suitable oxygen protecting groups include those known in the art, for example, methyl, methoxymethyl, etc., for example, as described in "Protective Groups in Organic Synthesis", 4$^{th}$ ed. P. G. M. Wuts; T. W. Greene, John Wiley, 2007, and references cited therein. In some embodiments, R$^{20}$ can be an oxygen substituted alkyl, which forms an "acetal" structure. Without wishing to be bound by theories, such groups can lead to a more labile ester and can be cleaved faster in vivo. For example, in some embodiments, R$^{20}$ can be

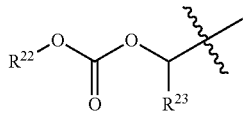

wherein R$^{22}$ is a C$_{1-4}$ alkyl, and R$^{23}$ is hydrogen or a C$_{1-4}$ alkyl.

The approach discussed above is not limited to the spirolactone core described herein. For example, as would be readily apparent to those skilled in the art in view of the present disclosure, any ACC inhibitor can be engineered to include a liver targeting moiety such as a pyridinyl substituted with COOH or a group that can be converted into a carboxylic acid group in vivo, for example, esters, amides, and the like, which can be particularly useful for treating a liver disease (e.g., NASH). In some embodiments, such ACC inhibitor can be engineered to include a pyridinyl substituted with COOR$^{20}$ as described herein, which can be a simple alkyl ester.

In some embodiments, R$^1$ can also be an optionally substituted heterocyclyl. For example, in some embodiments, R$^1$ is a 4-6 membered heterocyclyl optionally substituted with one or more (e.g., 1 or 2) substituents independently chosen from halogen, oxo, optionally substituted C$_{1-4}$ alkyl, optionally substituted C$_{1-4}$ alkoxy, optionally substituted C$_{3-6}$ cycloalkyl, and optionally substituted C$_{3-6}$ cycloalkoxy. In some embodiments, R$^1$ is a 4-6 membered heterocyclyl optionally substituted with one or more (e.g., 1 or 2) substituents independently chosen from halogen (e.g., F, Cl), C$_{1-4}$ alkyl, C$_{1-4}$ alkoxy, C$_{3-6}$ cycloalkyl, and C$_{3-6}$ cycloalkoxy, wherein each of the alkyl, alkoxy, cycloalkyl, and cycloalkoxy is optionally substituted with one to three substituents independently chosen from halogen (e.g., F) and C$_{1-4}$ alkyl.

In some preferred embodiments, R$^1$ is NR$^{10}$R$^{11}$. For example, in some embodiments, the compound of Formula Ia is a compound of Formula Ib:

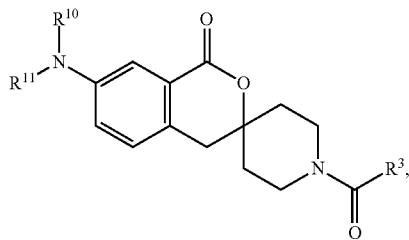

Formula Ib wherein R$^{10}$, R$^{11}$ and R$^3$ are as defined herein. In some embodiments, one of R$^{10}$ and R$^{11}$ is an optionally substituted phenyl or optionally substituted 5 or 6 membered heteroaryl (e.g., as described herein). In some embodiments, one of R$^{10}$ and R$^{11}$ is a 5-membered heteroaryl (e.g., those having 2-4 nitrogen atoms as described herein) optionally substituted with one or more (e.g., 1 or 2) substituents independently chosen from halogen, cyano and C$_{1-4}$ alkyl. For example, in some embodiments, one of R$^{10}$ and R$^{11}$ is a pyrazolyl, triazolyl or tetrazolyl. In some embodiments, one of R$^{10}$ and R$^{11}$ is pyrazolyl, triazolyl or tetrazolyl, each optionally substituted with 1 or 2 independently chosen C$_{1-4}$ alkyl (e.g., methyl or ethyl). In any of these embodiments, the other of R$^{10}$ and R$^{11}$ can be hydrogen or an optionally substituted alkyl (e.g., a C$_{1-4}$ alkyl such as methyl or ethyl). Other suitable R$^{10}$ and R$^{11}$ are described herein.

In some embodiments, R$^1$ can be COOR$^{12}$ or CONR$^{13}$R$^{14}$, wherein R$^{12}$, R$^{13}$ and R$^{14}$ are defined herein. For example, in some embodiments, R$^1$ is COOR$^{12}$, and R$^{12}$ can be hydrogen or an optionally substituted alkyl. In some embodiments, R$^{12}$ can be hydrogen or an optionally substituted C$_{1-6}$ alkyl, such as a C$_{1-4}$ alkyl optionally substituted with one or more (e.g., 1-3) substituents independently chosen from halogen and C$_{1-4}$ alkyl. In some embodiments, R$^1$ is CONR$^{13}$R$^{14}$, and R$^{13}$ and R$^{14}$ are each independently hydrogen or an optionally substituted alkyl. In some embodiments, R$^{13}$ and R$^{14}$ are each independently hydrogen or an optionally substituted C$_{1-6}$ alkyl, such as a C$_{1-4}$ alkyl optionally substituted with one or more (e.g., 1-3) substituents independently chosen from halogen and C$_{1-4}$ alkyl.

In some embodiments, R$^1$ can be S(O)$_n$R$^{15}$, wherein n and R$^{15}$ are defined herein. In some embodiments, n is 0. In some embodiments, n is 1. In some embodiments, n is 2. In some embodiments, R$^{15}$ is an optionally substituted alkyl. In some embodiments, R$^{15}$ is an optionally substituted C$_{1-6}$ alkyl, such as a C$_{1-4}$ alkyl optionally substituted with one or more (e.g., 1-3) substituents independently chosen from halogen and C$_{1-4}$ alkyl. In some embodiments, R$^{15}$ is an optionally substituted cycloalkyl. In some embodiments, R$^{15}$ is an optionally substituted C$_{3-6}$ cycloalkyl, such as a C$_{3-6}$ cycloalkyl optionally substituted with one or more (e.g., 1-3) substituents independently chosen from halogen and C$_{1-4}$ alkyl. In some embodiments, R$^{15}$ is NR$^{10}$R$^{11}$, suitable groups for R$^{10}$ and R$^{11}$ are described herein.

In some embodiments, R$^1$ can be OR6, wherein R$^1$6 is defined herein. In some embodiments, R$^1$6 is H. In some preferred embodiments, R$^1$6 is an optionally substituted alkyl (e.g., an optionally substituted C$_{1-6}$ alkyl) or an optionally substituted cycloalkyl (e.g., an optionally substituted C$_{3-6}$ cycloalkyl), thus R$^1$ is an optionally substituted alkoxy or cycloalkoxy as described herein. Other suitable R$^1$6 is described herein.

Suitable R$^3$ for compounds of Formula I (e.g., compounds of Formula I-1, Formula Ia, Formula Ib, or Formula Ic) are described herein. In some embodiments, $R^3$ is an optionally substituted aryl, for example, an optionally substituted $C_{6-10}$aryl. In some embodiments, $R^3$ is a $C_{6-10}$aryl optionally substituted with one or more (e.g., 1-3) substituents independently chosen from halogen, hydroxyl, cyano, optionally substituted $C_{1-4}$ alkyl, optionally substituted $C_{1-4}$ alkoxy, optionally substituted $C_{3-6}$ cycloalkyl, and optionally substituted $C_{3-6}$ cycloalkoxy. In some embodiments, $R^3$ can be an optionally substituted phenyl. In some embodiments, $R^3$ can be an optionally substituted bicyclic aryl. For example, in some preferred embodiments, $R^3$ is an optionally substituted naphthyl. In some embodiments, $R^3$ is a naphthyl optionally substituted with 1-3 substituents independently chosen from halogen, hydroxyl, cyano, $C_{1-4}$ alkyl, $C_{1-4}$ alkoxy, $C_{3-6}$ cycloalkyl, and $C_{3-6}$ cycloalkoxy, wherein each of the alkyl, alkoxy, cycloalkyl, and cycloalkoxy is optionally substituted with one to three substituents independently chosen from halogen (e.g., F) and $C_{1-4}$ alkyl. In some embodiments, $R^3$ is a naphthyl optionally substituted with 1-3 substituents independently chosen from halogen, hydroxyl, cyano, $C_{1-4}$ alkyl optionally substituted with 1-3 halogens, $C_{1-4}$ alkoxy optionally substituted with 1-3 halogens, $C_{3-6}$ cycloalkyl optionally substituted with 1-3 halogens, and $C_{3-6}$ cycloalkoxy optionally substituted with 1-3 halogens. In some embodiments, $R^3$ is a naphthyl optionally substituted with 1-3 substituents independently chosen from fluoro, chloro, hydroxyl, methyl, ethyl, trifluoromethyl, trifluoromethoxy, methoxy, ethoxy, and cyclopropyl.

In some embodiments, $R^3$ can also be an optionally substituted heteroaryl. For example, in some embodiments, $R^3$ is an optionally substituted 8-10 membered bicyclic heteroaryl. In some embodiments, $R^3$ is a 8-10 membered bicyclic heteroaryl optionally substituted with one or more (e.g., 1-3) substituents independently chosen from halogen, cyano, optionally substituted $C_{1-4}$ alkyl, optionally substituted $C_{1-4}$ alkoxy, optionally substituted $C_{3-6}$ cycloalkyl, and optionally substituted $C_{3-6}$ cycloalkoxy. In some embodiments, $R^3$ is an optionally substituted benzimidazolyl, pyrrolopyridinyl, pyrazolopyridinyl, indazolyl, indolyl, quinolynyl or isoquinolynyl. In some embodiments, $R^3$ is benzimidazolyl, pyrrolopyridinyl, pyrazolopyridinyl, indazolyl, indolyl, quinolynyl or isoquinolynyl each optionally substituted with 1-3 substituents independently chosen from halogen, hydroxyl, cyano, $C_{1-4}$ alkyl, $C_{1-4}$ alkoxy, $C_{3-6}$ cycloalkyl, and $C_{3-6}$ cycloalkoxy, wherein each of the alkyl, alkoxy, cycloalkyl, and cycloalkoxy is optionally substituted with one to three substituents independently chosen from halogen (e.g., F) and $C_{1-4}$ alkyl. In some embodiments, $R^3$ is benzimidazolyl, pyrrolopyridinyl, pyrazolopyridinyl, indazolyl, indolyl, quinolynyl or isoquinolynyl, each optionally substituted with 1-3 substituents independently chosen from halogen, hydroxyl, cyano, $C_{1-4}$ alkyl optionally substituted with 1-3 halogens, $C_{1-4}$ alkoxy optionally substituted with 1-3 halogens, $C_{3-6}$ cycloalkyl optionally substituted with 1-3 halogens, and $C_{3-6}$ cycloalkoxy optionally substituted with 1-3 halogens. In some embodiments, $R^3$ is benzimidazolyl, pyrrolopyridinyl, pyrazolopyridinyl, indazolyl, indolyl, quinolynyl or isoquinolynyl, each optionally substituted with 1-3 substituents independently chosen from fluoro, chloro, hydroxyl, methyl, ethyl, trifluoromethyl, trifluoromethoxy, methoxy, ethoxy, and cyclopropyl. Preferably, substitutions of the heteroaryls herein do not result in a halogen, cyano, or oxygen atom (e.g., from a hydroxyl, alkoxy or cycloalkoxy group) directly attach to a ring heteroatom, such as a ring nitrogen atom, of the heteroaryls. Also, those skilled in the art would understand that when a compound has a hydroxyl group attached to a carbon next to a nitrogen ring atom, the compound may exist predominantly in one or more tautomeric forms. For example, a 2-hydroxyl substituted 1-methyl-benzimidazole may exist predominantly in Form B as shown below

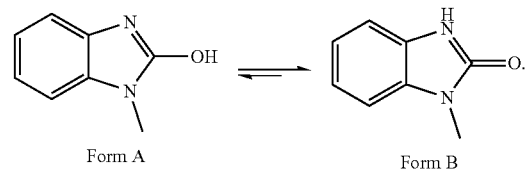

Form A            Form B

Thus, as used herein, a heteroaryl substituted with a hydroxyl group should be understood as encompassing all tautomeric forms when possible, e.g., Forms A and B above.

Various positions of the bicyclic aryls or heteroaryls suitable for $R^3$ can be used to attach to the spirolactone core, for example, a position that is not immediately adjacent to the distal ring. For example, both 1- and 2-naphthyl are suitable $R^3$ groups. In some embodiments, $R^3$ is preferably 2-naphthyl. Similarly, quinolinyl can have seven different attach points at one of positions 2-8

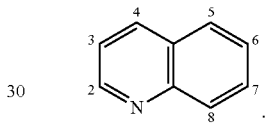

In some embodiments, $R^3$ is preferably 2-, 3-, 6-, or 7-quinolinyl (positions not immediately adjacent to the distal ring). In some embodiments, $R^3$ is 4-, 5-, or 8-quinolinyl.

In any of the embodiments described herein, $R^3$ can be optionally substituted naphthyl, quinolinyl, benzimidazolyl, pyrrolopyridinyl, indolyl, or indazolyl:

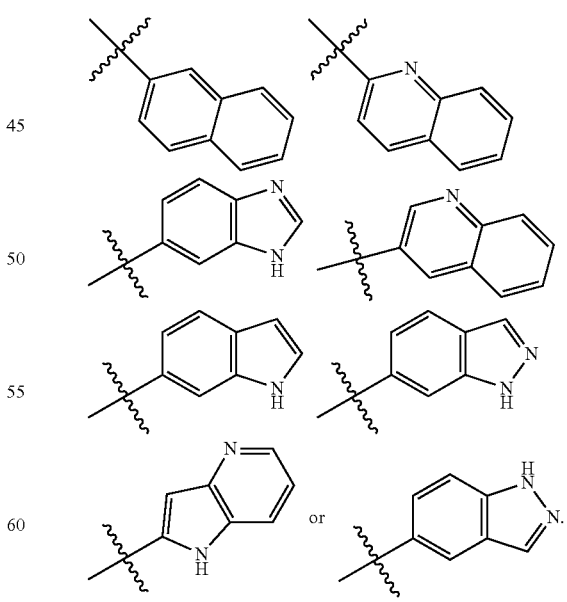

In some embodiments, the naphthyl, quinolinyl, benzimidazolyl, pyrrolopyridinyl, indolyl, or indazolyl is optionally substituted with one or more (e.g., 1-3) substituents independently chosen from halogen, cyano, hydroxyl, $C_{1-4}$ alkyl, $C_{1-4}$ alkoxy, $C_{3-6}$ cycloalkyl, and $C_{3-6}$ cycloalkoxy, wherein each of the alkyl, alkoxy, cycloalkyl, and cycloalkoxy is optionally substituted with one or more (e.g., 1-3) substituents independently chosen from halogen (e.g., F) and $C_{1-4}$ alkyl. In some embodiments, the naphthyl, quinolinyl, benzimidazolyl, pyrrolopyridinyl, indolyl, or indazolyl is optionally substituted with one or more (e.g., 1-3) substituents independently chosen from halogen, cyano, hydroxyl, $C_{1-4}$ alkyl optionally substituted with 1-3 halogens, $C_{1-4}$ alkoxy optionally substituted with 1-3 halogens, $C_{3-6}$ cycloalkyl optionally substituted with 1-3 halogens, and $C_{3-6}$ cycloalkoxy optionally substituted with 1-3 halogens. In some embodiments, the naphthyl, quinolinyl, benzimidazolyl, pyrrolopyridinyl, indolyl, or indazolyl is optionally substituted with one or more (e.g., 1-3) substituents independently chosen from fluoro, chloro, hydroxyl, methyl, trifluoromethyl, ethyl, methoxy, trifluoromethoxy, ethoxy, and cyclopropyl. Preferably, substitutions of the benzimidazolyl, pyrrolopyridinyl, indolyl, or indazolyl herein do not result in a halogen, cyano, or oxygen atom (e.g., from a hydroxyl, alkoxy or cycloalkoxy group) directly attach to a ring nitrogen atom.

In any of the embodiments described herein, $R^3$ can be optionally substituted naphthyl or quinolynyl:

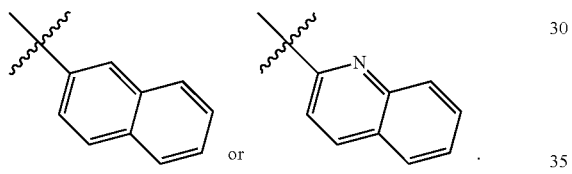

In some embodiments, the naphthyl or quinolynyl is optionally substituted with 1-3 substituents independently chosen from halogen, cyano, $C_{1-4}$ alkyl, $C_{1-4}$ alkoxy, $C_{3-6}$ cycloalkyl, and $C_{3-6}$ cycloalkoxy, wherein each of the alkyl, alkoxy, cycloalkyl, and cycloalkoxy is optionally substituted with one to three substituents independently chosen from halogen (e.g., F) and $C_{1-4}$ alkyl. In some embodiments, the naphthyl or quinolynyl is optionally substituted with 1-3 substituents independently chosen from halogen, cyano, $C_{1-4}$ alkyl optionally substituted with 1-3 halogens, $C_{1-4}$ alkoxy optionally substituted with 1-3 halogens, $C_{3-6}$ cycloalkyl optionally substituted with 1-3 halogens, and $C_{3-6}$ cycloalkoxy optionally substituted with 1-3 halogens. In some embodiments, the naphthyl or quinolynyl is optionally substituted with 1-3 substituents independently chosen from fluoro, chloro, hydroxyl, methyl, trifluoromethyl, ethyl, methoxy, trifluoromethoxy, ethoxy, and cyclopropyl.

In some embodiments, $R^3$ can be

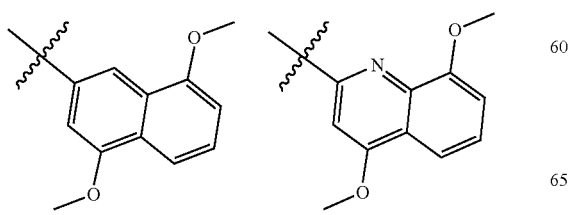

-continued

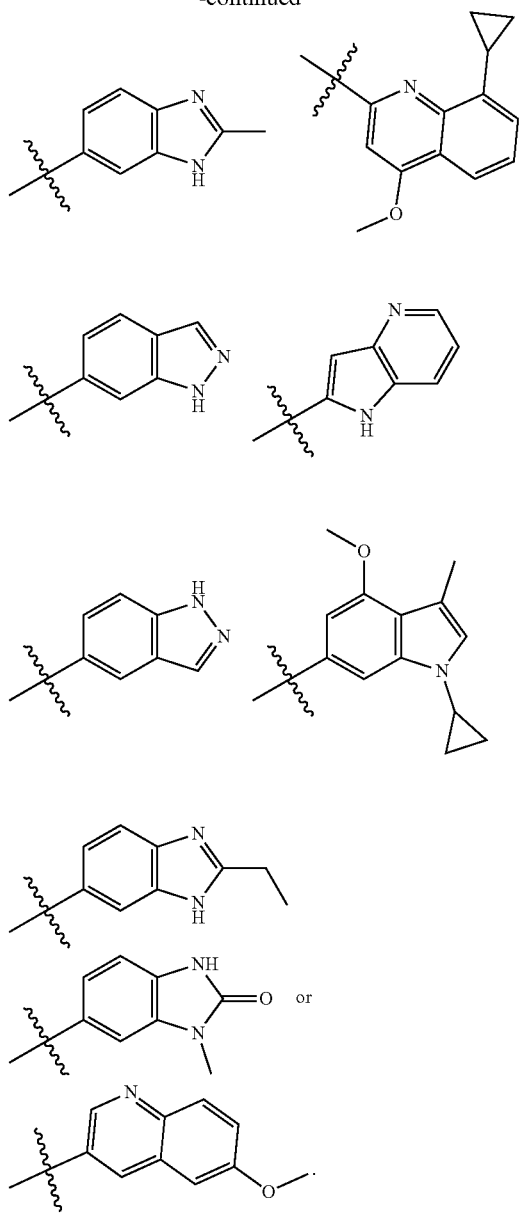

In any of the embodiments described herein, $R^3$ can be

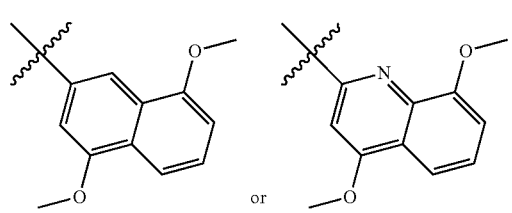

Exemplary Spirolactone Compounds

Certain embodiments of the present disclosure are directed to some exemplary spirolactone compounds.

In some embodiments, the present disclosure provides a compound of Formula II-1 to Formula II-3, or a pharmaceutically acceptable salt thereof:

Formula II-1

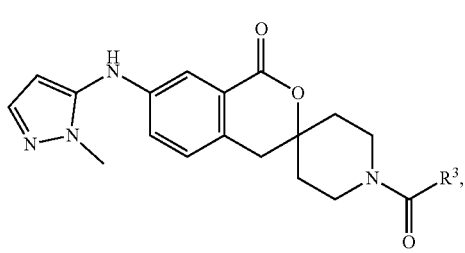

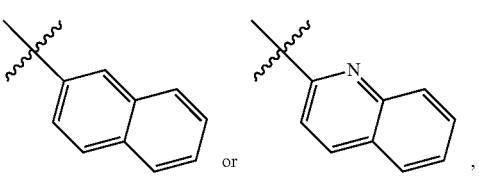 [SMILES: *c1ccc2ccccc2c1 ; *c1ccc2ccccc2n1]

or , each optionally substituted with 1-3 substituents independently chosen from fluoro, chloro, hydroxyl, methyl, trifluoromethyl, ethyl, methoxy, trifluoromethoxy, ethoxy, and cyclopropyl.

In some embodiments, the present disclosure provides a compound of Formula III-1 or Formula III-2, or a pharmaceutically acceptable salt thereof:

Formula II-2

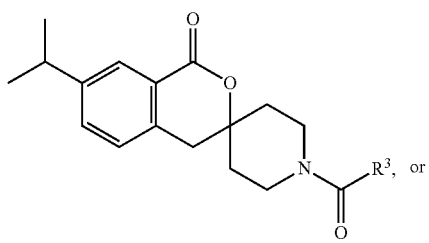

Formula III-1

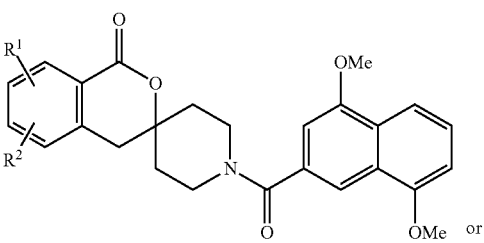

or

Formula II-3

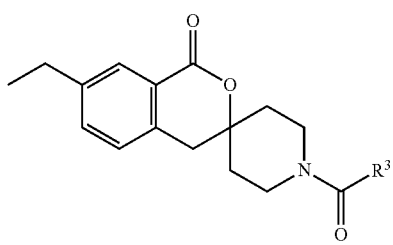

Formula III-2

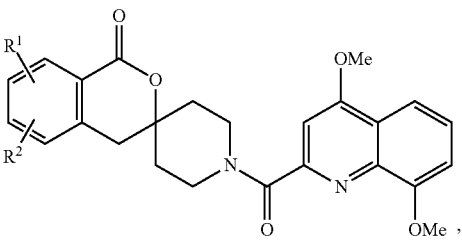

wherein R³ can be any of those defined herein. For example, in some preferred embodiments, R³ is an optionally substituted naphthyl. In some embodiments, R³ is a naphthyl optionally substituted with 1-3 substituents independently chosen from halogen, cyano, $C_{1-4}$ alkyl optionally substituted with 1-3 halogens, $C_{1-4}$ alkoxy optionally substituted with 1-3 halogens, $C_{3-6}$ cycloalkyl optionally substituted with 1-3 halogens, and $C_{3-6}$ cycloalkoxy optionally substituted with 1-3 halogens. In some embodiments, R³ is a naphthyl optionally substituted with 1-3 substituents independently chosen from fluoro, chloro, hydroxyl, methyl, ethyl, trifluoromethyl, trifluoromethoxy, methoxy, ethoxy, and cyclopropyl. In some preferred embodiments, R³ is an optionally substituted quinolynyl. In some embodiments, R³ is a quinolynyl optionally substituted with 1-3 substituents independently chosen from halogen, cyano, $C_{1-4}$ alkyl optionally substituted with 1-3 halogens, $C_{1-4}$ alkoxy optionally substituted with 1-3 halogens, $C_{3-6}$ cycloalkyl optionally substituted with 1-3 halogens, and $C_{3-6}$ cycloalkoxy optionally substituted with 1-3 halogens. In some embodiments, R³ is a quinolynyl optionally substituted with 1-3 substituents independently chosen from fluoro, chloro, hydroxyl, methyl, ethyl, trifluoromethyl, trifluoromethoxy, methoxy, ethoxy, and cyclopropyl.

In some embodiments, R³ in Formula TT-1 to Formula TT-3 can be wherein R¹ and R² can be any of those defined herein. In some embodiments, R² in Formula III-1 or Formula III-2 is hydrogen.

In some embodiments, the present disclosure provides a compound of Formula III-3 to Formula III-6, or a pharmaceutically acceptable salt thereof:

Formula III-3

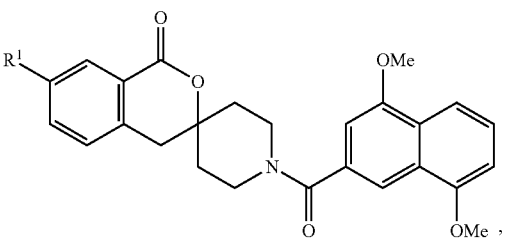

-continued

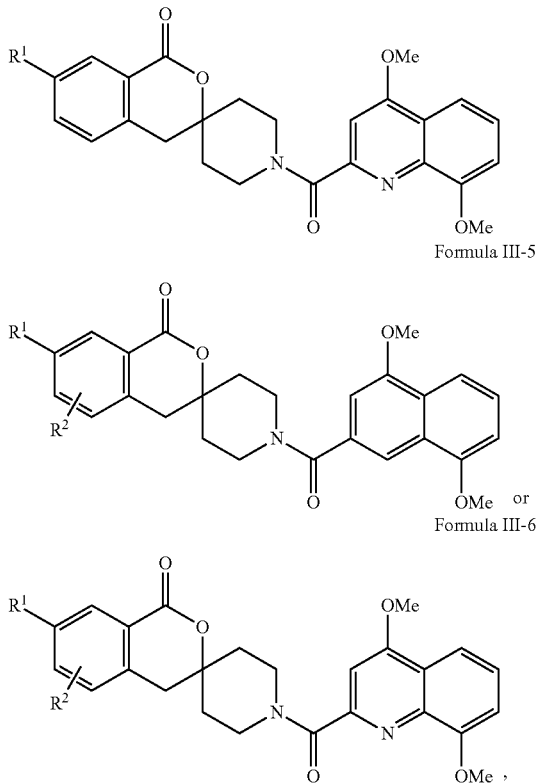

Formula III-4

Formula III-5

Formula III-6 wherein $R^1$ and $R^2$ can be any of those defined herein as suitable.

In some embodiments, $R^1$ in any of Formula III-1 to Formula III-6 can be an optionally substituted $C_{1-4}$ alkyl, for example, methyl, ethyl, isopropyl, or tert-butyl. In some embodiments, $R^1$ in any of Formula III-1 to Formula III-6 can be an optionally substituted $C_{1-4}$ alkoxy, for example, methoxy, trifluoromethoxy, ethoxy or isopropoxy. In some embodiments, $R^1$ in any of Formula III-1 to Formula III-6 can be $NR^{10}R^{11}$. In some embodiments, one of $R^{10}$ and $R^{11}$ is an optionally substituted 5 or 6 membered heteroaryl. In some embodiments, one of $R^{10}$ and $R^{11}$ is a 5-membered heteroaryl having 2-4 ring nitrogen atoms, which is optionally substituted with 1 or 2 substituents independently chosen from halogen, cyano and $C_{1-4}$ alkyl. In some embodiments, one of $R^{10}$ and $R^{11}$ is a pyrazolyl, triazolyl or tetrazolyl, each optionally substituted with a $C_{1-4}$ alkyl. In any of these embodiments, the other of $R^{10}$ and $R^{11}$ can be hydrogen or $C_{1-4}$ alkyl (e.g., methyl). For example, in some embodiments, one of $R^{10}$ and $R^{11}$ is

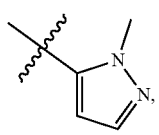 [SMILES: *c1ccnn1C]

and the other of $R^{10}$ and $R^{11}$ is hydrogen or methyl. In some embodiments, $R^2$ in any of Formula III-1, Formula III-2, Formula III-4 and Formula III-6 can be hydrogen. Other suitable $R^1$ and $R^2$ are described herein.

In some embodiments, the present disclosure also provides any of the compounds of Examples 1-22, or a salt (e.g., pharmaceutically acceptable salt) thereof. For example, in some embodiments, the present disclosure also provides:

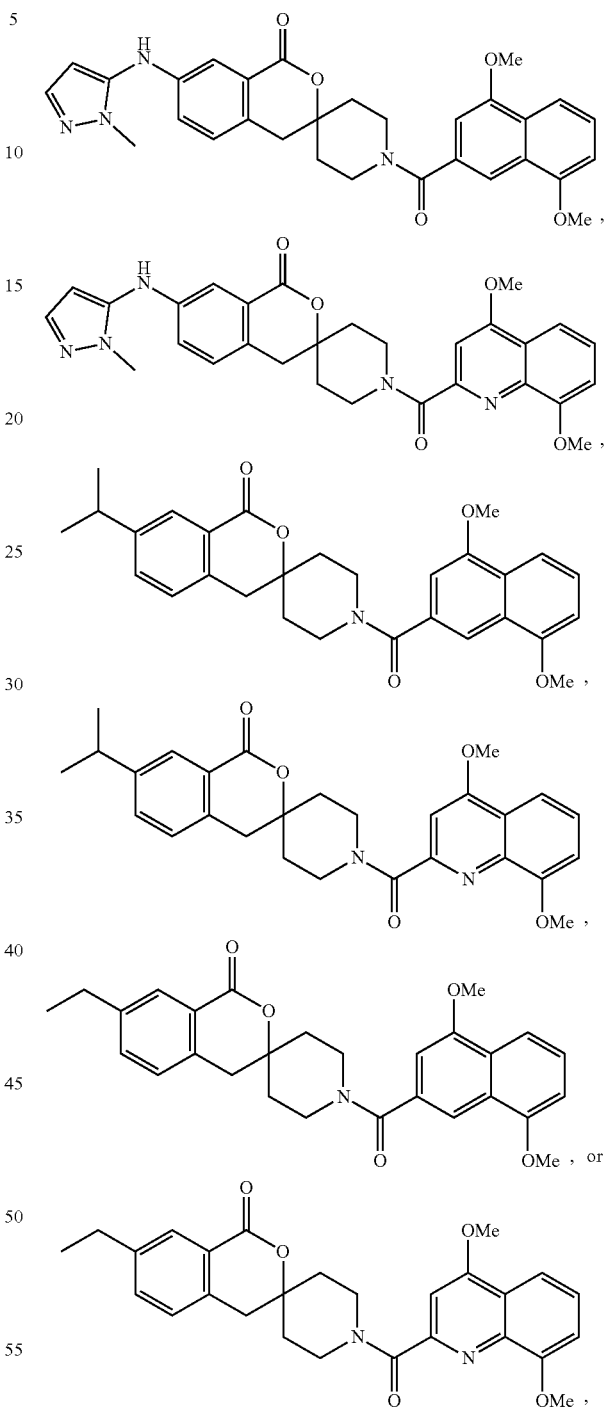

or a pharmaceutically acceptable salt thereof.

Method of Synthesis

Certain embodiments of the present disclosure are directed to methods of synthesizing the spirolactone compounds described herein.

In some embodiments, the present disclosure provides a method of synthesizing a compound of Formula I,

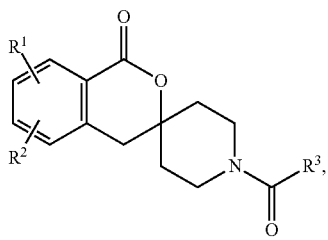

Formula I wherein $R^1$, $R^2$, and $R^3$ are as defined herein. In some embodiments, the method comprises reacting a compound of Formula S-1, or a salt thereof, with an acid of Formula S-2, or an activated form thereof (e.g., acyl chloride, anhydride) to form a compound of Formula I,

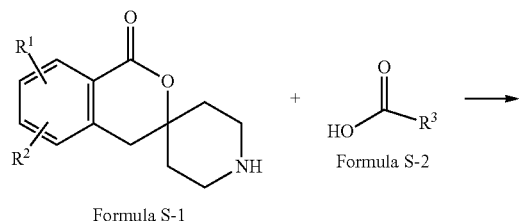

Formula S-1     Formula S-2

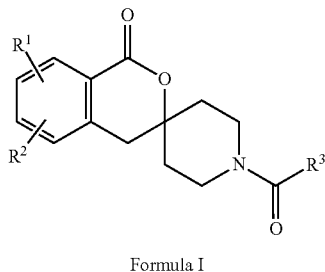

Formula I wherein $R^1$, $R^2$, and $R^3$ are as defined herein. Suitable reagents and conditions for this transformation are known in the art and exemplified in the Examples section, e.g., using HATU ((1-[Bis(dimethylamino)methylene]-1H-1,2,3-triazolo[4,5-b]pyridinium 3-oxide hexafluorophosphate)) and diisopropyl amine.

In some embodiments, the method comprises reacting a compound of Formula S-3 with $R^1G^2$ or another agent to form a compound of Formula I,

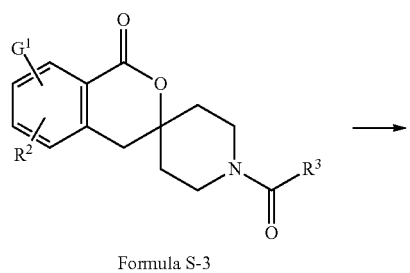

Formula S-3

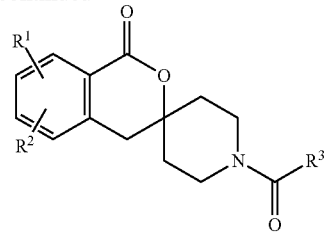

Formula I wherein $G^1$ is halo (preferably Br or I), CN, or $NH_2$, and $R^1$, $R^2$, and $R^3$ are as defined herein, wherein $R^1G^2$ is a reagent capable of reacting with Formula S-3 to form Formula I under suitable conditions. For example, in some embodiments, $G^1$ is halo, $R^1G^2$ can be an organozinc reagent, organoboron reagent, organotin reagent, which can react with the compound of Formula S-3, for example, under palladium or copper catalyzed coupling reaction conditions to form the compound of Formula I. In some embodiments, $R^1G^2$ is an amino compound with $G^2$ being H, and $G^1$ is halo, and $R^1G^2$ can react with the compound of Formula S-3, for example, under palladium or copper catalyzed coupling reaction conditions to form the compound of Formula I. In some embodiments, $R^2$ is H. In some embodiments, the compound of Formula S-3 is Formula S-3a, wherein $G^1$ and $R^3$ are defined herein, for example, in some embodiments of Formula S-3a, $G^1$ is halo (e.g., Br or I),

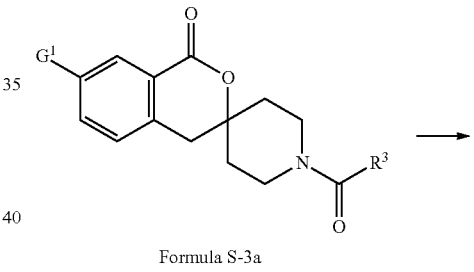

Formula S-3a

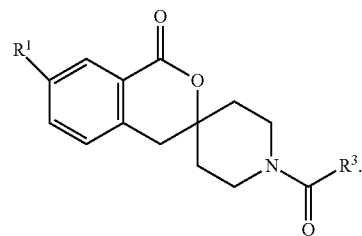

Formula Ia

In some embodiments, $R^1G^2$ is

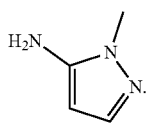

In some embodiments, $R^1G^2$ is an organoboron agent, an organotin agent, or an organometallic agent such as organozinc agent, where $G^2$ is boronic acid or ester, trisubstituted Sn, or a metal ion such as Zn, and in some embodiments, $R^1$ can be an optionally substituted aryl or optionally substituted heteroaryl (e.g., 5- or 6-membered heteroaryl such as 2-, 3-, or 4-pyridinyl). Suitable coupling reaction conditions are known in the art and are exemplified in the Examples section. In some embodiments, where $G^1$ is CN, the compound of Formula S-3 or S-3a can react with another agent, such as an azide to form a tetrazole as R group in Formula I or Ia.

Compounds of Formula S-1 can be readily accessible by those skilled in the art in view of the present disclosure. For example, certain compounds of Formula S-1 can be prepared by following Scheme 1:

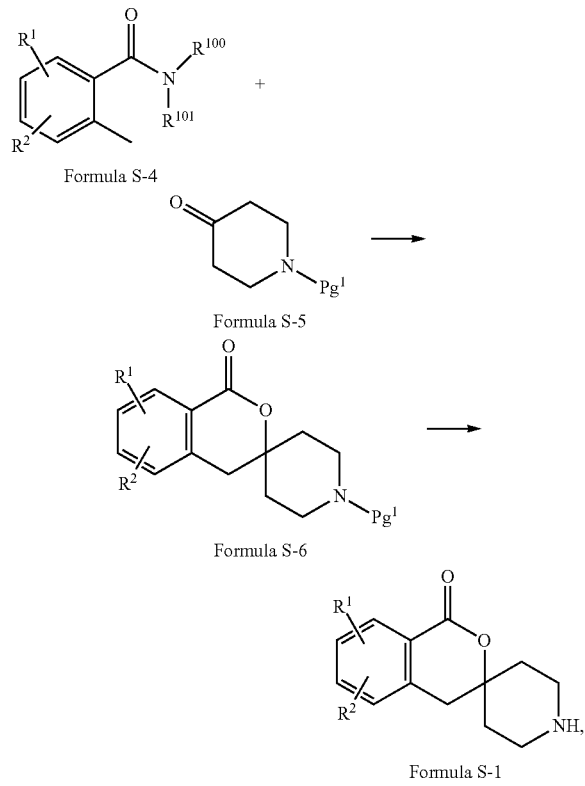

wherein $Pg^1$ is a nitrogen protecting group, such as benzyl, $R^{100}$ and $R^{101}$ are independently hydrogen or $C_{1-4}$ alkyl (e.g., methyl), and $R^1$ and $R^2$ are defined herein. In some embodiments, both $R^{100}$ and $R^{101}$ are hydrogen. In some embodiments, one of $R^{100}$ and $R^{101}$ is hydrogen and the other of $R^{100}$ and $R^{101}$ is a $C_{1-4}$ alkyl (e.g., methyl). Thus, the compound of Formula S-4 can, for example, be treated with a strong base such as n-BuLi, which then react with the compound of Formula S-5. After acidic treatment (e.g., 50% acetic acid and concentrated $H_2SO_4$) under suitable conditions, e.g., reflux for a few hours, the spirocyclic compound of Formula S-6 can be obtained. See e.g., Yamato M. et al. "Synthesis and Structure-Activity Relationship of Spiro [isochromanpiperidine] Analogues for Inhibition of Histamine Release," J. Med. Chem. 24:194-198 (1981), the content of which is hereby incorporated by reference in its entirety. The compound of Formula S-1 can be obtained by deptotection of the compound of Formula S-6. For example, when $Pg^1$ is benzyl, a hydrogenation reaction converts the compound of Formula S-6 into the compound of Formula S-1. Other suitable nitrogen protecting groups are known in the art, for example, as described in "Protective Groups in Organic Synthesis", 4th ed. P. G. M. Wuts; T. W. Greene, John Wiley, 2007, and references cited therein.

In some embodiments, the present disclosure provides methods for preparing compound B3 and compounds of Formula S-la, or salts thereof, for example, by following Scheme 2:

wherein $G^1$ is a halogen, e.g., Br or I, or cyano. In some embodiments, the piperidine nitrogen in compounds of B1, B2, B3, and Formula S-la can be protected with a nitrogen protecting group such as benzyl, Boc, etc. Other suitable nitrogen protecting groups include those known in the art, for example, as described in "Protective Groups in Organic Synthesis", 4th ed. P. G. M. Wuts; T. W. Greene, John Wiley, 2007, and references cited therein. For example, compound B1, or a salt thereof, which can be obtained by methods described in Scheme 1, can undergo a nitration reaction (e.g., with $HNO_3$) to form compound B2, or a salt thereof, which (or an N-protected derivative thereof) can then be reduced (e.g., hydrogenation with Pd/C) to form compound B3, or a salt thereof, or an N-protected derivative thereof. The compound B3, or a salt thereof, or an N-protected derivative thereof, can then undergo a halogenation reaction to convert the amine group into a halogen (e.g., Br, or I), for example, under a typical Sandmeyer condition (e.g., diazotization followed by reaction with CuBr, CuCN or CuI). Compound B3 or compounds of Formula S-la can react with an acid of Formula S-2, or an activated form thereof (e.g., acyl chloride, anhydride) to form certain compounds of Formula S-3a.

As will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", 4th ed. P. G. M. Wuts; T. W. Greene, John Wiley, 2007, and references cited therein. The reagents for the reactions described herein are generally known compounds or can be prepared by known procedures or obvious modifications thereof. For example, many of the reagents are available from commercial suppliers such as Aldrich Chemical Co. (Milwaukee, Wisconsin, USA), Sigma (St. Louis, Missouri, USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, 7th Edition), and Larock's Comprehensive Organic Transformations (Wiley-VCH, 1999).

Pharmaceutical Compositions

Certain embodiments are directed to a pharmaceutical composition comprising one or more of the spirolactone compounds of the present disclosure.

The pharmaceutical composition can optionally contain a pharmaceutically acceptable excipient. In some embodiments, the pharmaceutical composition comprises a spirolactone compound of the present disclosure and a pharmaceutically acceptable excipient. Pharmaceutically acceptable excipients are known in the art. Non-limiting suitable excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

The pharmaceutical composition can include any one or more of the spirolactone compounds of the present disclosure. For example, in some embodiments, the pharmaceutical composition comprises a compound of any of Formula I, Formula I-1, Formula Ia, Formula Ib, Formula Ic, Formula II-1 to 11-3, and Formula III-1 to III-6, or any of Examples 1-22, or a pharmaceutically acceptable salt thereof. In any of the embodiments described herein, the pharmaceutical composition comprises any of the compounds of Examples 1-22, or a pharmaceutically acceptable salt thereof. For example, in some embodiments, the pharmaceutical composition can comprise a compound of

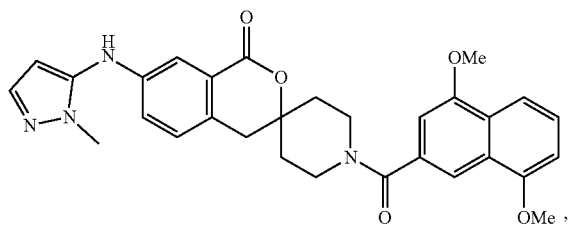

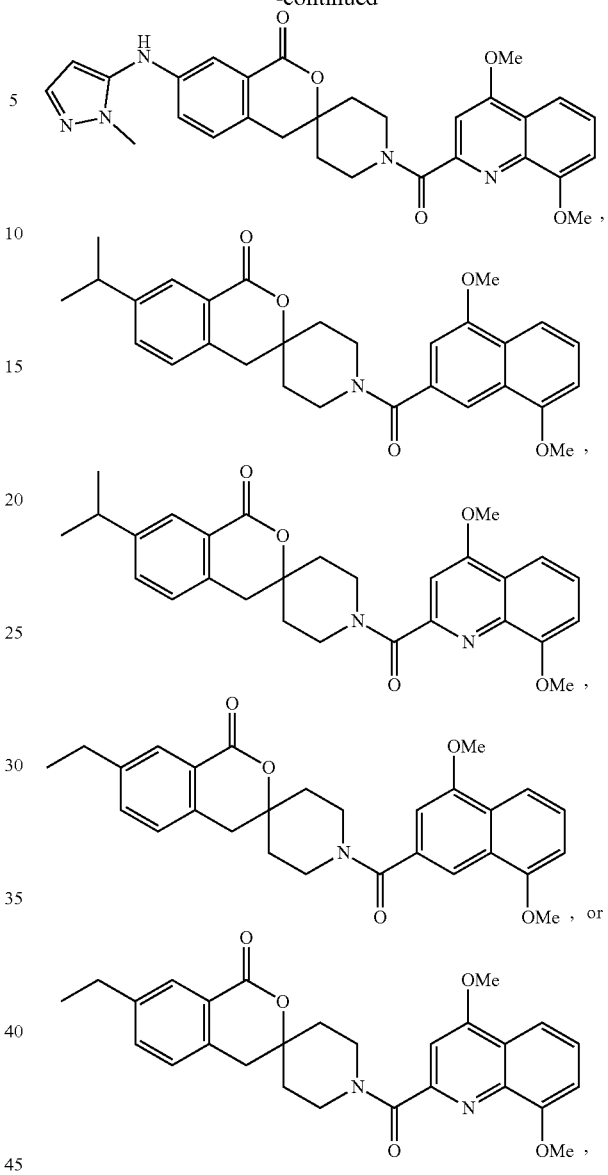

or a pharmaceutically acceptable salt thereof.

The pharmaceutical composition can also be formulated for delivery via different routes, such as oral, parenteral, inhalation, topical, etc.

In some embodiments, the pharmaceutical composition is formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion. Excipients for the preparation of compositions for oral administration are known in the art. Non-limiting suitable excipients include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof.

In some embodiments, the pharmaceutical composition is formulated for parenteral administration (such as intravenous injection or infusion). The parenteral formulations can be, for example, an aqueous solution, a suspension, or an emulsion. Excipients for the preparation of parenteral formulations are known in the art. Non-limiting suitable excipients include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof.

In some embodiments, the pharmaceutical composition is formulated for inhalation. The inhalable formulations can be, for example, formulated as a nasal spray, dry powder, or an aerosol administrable through a metered-dose inhaler. Excipients for preparing formulations for inhalation are known in the art. Non-limiting suitable excipients include, for example, lactose, talc, silicic acid, aluminum hydroxide, calcium silicates and polyamide powder, and mixtures of these substances. Sprays can additionally contain propellants, such as chlorofluorohydrocarbons and volatile unsubstituted hydrocarbons, such as butane and propane.

In some embodiments, the pharmaceutical composition is formulated for topical administration. The topical formulations can be, for example, in the form of a topical solution, lotion, shampoo, transdermal spray, topical film, foam, powder, paste, sponge, transdermal patch, tincture, tape, cream, gel, or ointment. Excipients for preparing topical formulations are known in the art. Non-limiting suitable excipients include, for example, animal and vegetable fats, oils, waxes, paraffins, starch, tragacanth, cellulose derivatives, polyethylene glycols, silicones, bentonites, silicic acid, talc and zinc oxide, and mixtures thereof.

For example, the topical formulations described herein can have one or more "lipophilic solvent(s)" that acts as a carrier into the pilosebaceous unit. A lipophilic solvent useful in the invention can be miscible with water and/or lower chain (e.g., $C_{1-6}$) alcohols. In some embodiments, the lipophilic solvent can be a glycol, e.g., propylene glycol. In some embodiments, the lipophilic solvent can be a polyethylene glycol, e.g., with average molecular weight (e.g., $M_n$ or $M_w$) ranging from 200 to 20000 Dalton. In some embodiments, the lipophilic solvent is a glycol ether, e.g., diethylene glycol monoethyl ether (transcutol).

The topical formulations described herein can also have one or more "filler(s)". Non-limiting useful fillers include water and lower (e.g., $C_{1-6}$) alcohols, including ethanol, 2-propanol and n-propanol. In some embodiments, the filler is water, ethanol and/or 2-propanol.

The topical formulations described herein can also have one or more "humectant(s)" used to provide a moistening effect. Non-limiting useful humectants include glycerin, polyhydric alcohols and silicone oils. In some embodiments, the topic formulation comprises one or more humectants chosen from glycerin, propylene glycol and cyclomethicone.

The topical formulations described herein can also have a gelling agent that increases the viscosity of the final formulation. In some embodiments, the gelling agent can also act as an emulsifying agent. Non-limiting useful gelling agents include classes of celluloses, acrylate polymers and acrylate copolymers, for example, hydroxypropyl cellulose, hydroxymethyl cellulose, Pluronic PF127 polymer, carbomer 980, carbomer 1342 and carbomer 940. In some embodiments, the topic formulation comprises one or more gelling agents chosen from hydroxypropyl cellulose (Klucel® EF, GF and/or HF), Pluronic PF127, carbomer 980 and carbomer 1342 (Pemulen® TR-1, TR-2 and/or Carbopol® ETD 2020).

The topical formulations described herein can also have one or more anti-oxidants, radical scavengers, and/or stabilizing agents. Non-limiting useful examples include butylatedhydroxytoluene, butylatedhydroxyanisole, ascorbyl palmitate, citric acid, vitamin E, vitamin E acetate, vitamin E-TPGS, ascorbic acid, tocophersolan and propyl gallate.

The topical formulations described herein can also have one or more preservatives that exhibit anti-bacterial and/or anti-fungal properties. Non-limiting useful examples include diazolidinyl urea, methylparaben, propylparaben, tetrasodium EDTA, and ethylparaben.

The topical formulations described herein can also have one or more chelating agents. Non-limiting examples for use herein include EDTA, disodium edeate, dipotassium edeate, cyclodextrin, trisodium edetate, tetrasodium edetate, citric acid, sodium citrate, gluconic acid and potassium gluconate.

Various amounts of active ingredients and excipients are suitable for the topical formulations described herein. For example, in some embodiments, the topical formulation can include a spirolactone of the present disclosure in the amount of about 0.001 to about 5% (e.g., about 0.01 to about 1%, about 0.01% to about 0.5%) by weight of the total weight of the formulation. In some embodiments, the topical formulation can include the following ingredients (in weight percentage of the total weight of the formulation):

| Ingredients | % by weight (Typical Range) | % by weight (Preferred Range) | % by weight (More preferred Range) |
|---|---|---|---|
| Filler (e.g., Water) | about 45-75% | about 50-70% | about 55-65% (e.g., about 60%, 61%) |
| Lipophilic Solvent (e.g., Diethylene Glycol Monoethyl Ether) | about 15-45% | about 20-40% | about 25-35% (e.g., about 31%, 32%) |
| Humectant (e.g., Glycerin) | about 1-15% | about 3-12% | about 4-8% (e.g., about 6%) |
| Gelling agent (e.g., Carbopol 980) | about 1-10% | about 1-8% | about 1-5% (e.g., about 3%) |
| Active Ingredient (e.g., Compound Example 6) | about 0.001-5% | about 0.01-1% | about 0.01-0.5% (e.g., about 0.1% or about 0.05%) |

The pharmaceutical composition can include various amounts of the spirolactone compounds of the present disclosure, depending on various factors such as the intended use and potency of the compound. For example, in some embodiments, the pharmaceutical composition can comprise a spirolactone compound of the present disclosure in an amount effective for inhibiting ACC1 and/or ACC2 activities in a cell, which is in vitro, in vivo, or ex vivo. In some embodiments, the amount is effective to achieve about 10%, about 20%, about 50%, about 70%, about 90%, about 99% inhibition of the ACC1 and/or ACC2 activities, compared to a control, or any ranges between the recited values.

In some embodiments, the pharmaceutical composition can comprise the spirolactone compound of the present disclosure in an amount, when administered to a subject (e.g., a human) in need thereof, effective to inhibit one or more activities in the subject. In some embodiments, the one or more activities are chosen from acetyl-CoA carboxylases ACC1 and/or ACC2 activities, lipogenesis, proliferation of cells (e.g., adipocytes, melanocytes, keratinocytes, squamous cells, Merkel cells, Langerhans cells, or skin stem cells) in epidermis, dermis, and/or hypodermis, proliferation of human sebocytes, proliferation of human keratinocytes, differentiation of fibroblast to adipocytes in cutaneous and/or subcutaneous layers, sebum production, inflammation, and combinations thereof. In some embodiments, the pharmaceutical composition can comprise the spirolactone compound of the present disclosure in an amount, when administered to a subject (e.g., a human) in need thereof, (a) effective to inhibit acetyl-CoA carboxylases ACC1 and/or ACC2 activities in a cell (e.g., a sebocyte, adipocyte) of the subject; (b) effective to inhibit lipogenesis (e.g., lipogenesis of sebocytes, lipogenesis of adipocytes, etc.) in the subject; (c) effective to inhibit proliferation of cells, such as adipocytes, melanocytes, keratinocytes, squamous cells, Merkel cells, Langerhans cells, or skin stem cells, in epidermis, dermis, and/or hypodermis in the subject; (d) effective to inhibit proliferation of human sebocytes in the subject; (e) effective to inhibit proliferation of human keratinocytes in the subject; (f) effective to inhibit differentiation of fibroblast to adipocytes in cutaneous and/or subcutaneous layers in the subject; (g) effective to inhibit sebum production in the subject; (h) effective to inhibit inflammation in the subject, or any combinations thereof. In some embodiments, the subject is characterized as having a disease or disorder chosen from acne, seborrhea, sebaceous hyperplasia, seborrheic keratosis, sebaceous adenoma, sebaceous cyst, actinic keratosis, sebaceous carcinoma, squamous cell carcinoma, melanoma, phymatous rosacea, fibrofolliculomas in Birt-Hogg-Dube syndrome, and combinations thereof. In some embodiments, the subject is characterized as having NASH.

In some embodiments, the pharmaceutical composition comprises a therapeutically effective amount of a spirolactone compound of the present disclosure. In some embodiments, the pharmaceutical composition comprises a therapeutically effective amount of the spirolactone compound of the present disclosure and a pharmaceutically acceptable excipient. As used herein, a therapeutically effective amount of a spirolactone compound of the present disclosure is an amount effective to treat a disease or disorder as described herein, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

The pharmaceutical composition can be used for treating various diseases or disorders. Non-limiting diseases or disorders suitable for such treatment include skin diseases (such as diseases or disorders associated with aberrant sebocyte and/or keratinocyte activity), non-alcoholic fatty liver diseases or disorders, metabolic diseases or disorders, and proliferative diseases such as cancer. Non-limiting suitable diseases or disorders associated with aberrant sebocyte and/or keratinocyte activity include, for example, acne, seborrhea, sebaceous hyperplasia, seborrheic keratosis, sebaceous adenoma, sebaceous cyst, actinic keratosis, sebaceous carcinoma, squamous cell carcinoma, melanoma, phymatous rosacea, fibrofolliculomas in Birt-Hogg-Dube syndrome, and a combination thereof. Non-limiting suitable non-alcoholic fatty liver diseases or disorders include, for example, non-alcoholic steatohepatitis (NASH). Non-limiting suitable metabolic diseases or disorders include, for example, obesity and/or diabetes.

The pharmaceutical composition can also include one or more active agents in addition to the spirolactone compounds of the present disclosure. The spirolactone compound of the present disclosure and the one or more active agents can be present in a single dosage form (e.g., in a single pill, tablet, capsule, topic ointment, gel, paste, cream, etc.) or in separate dosage forms. For example, the spirolactone compound of the present disclosure can be in an oral or topical formulation, whereas the one or more active agents can be in the same formulation or a different oral or topical formulation. When in different dosage forms, the spirolactone compound of the present disclosure and one or more active agents can be included in a kit.

Various active agents can be combined with the spirolactone compound of the present disclosure in the pharmaceutical composition. For example, in some embodiments, the one or more active agents are suitable for treating diseases or disorders associated with aberrant sebocyte and/or keratinocyte activity, such as acne. Non-limiting useful examples include antibiotics (e.g., clindamycin, erythromycin, metronidazole, sulfacetamide, or tetracyclines such as doxycycline and minocycline), retinoids (e.g., adapalene, isotretinoin, retinol, tazarotene, or tretinoin), and combinations thereof. In some embodiments, the one or more active agents are present in an amount effective for treating a disease or disorder associated with aberrant sebocyte and/or keratinocyte activity such as acne.

In some embodiments, the one or more active agents are suitable for treating metabolic diseases or non-alcoholic fatty liver diseases. Non-limiting useful examples of such agents include angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacyl glycerol O-acyltransferase 1 (DGAT1) inhibitors, dipeptidyl peptidase IV (DPPIV) inhibitors, farnesoid X receptor (FXR) agonists, galectin-3 inhibitors, glucagon-like peptide 1 (GLP1) agonists, glutathione precursors, hepatitis C virus NS3 protease inhibitors, HMG CoA reductase inhibitors, 11β-hydroxysteroid dehydrogenase (11β-HSD1) inhibitors, IL-1β antagonists, IL-6 antagonists, IL-10 agonists, IL-17 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPAR-alpha agonists, PPAR-gamma agonists, PPAR-delta agonists, Rho associated protein kinase 2 (ROCK2) inhibitors, sodium glucose transporter-2 (SGLT2) inhibitors, stearoyl CoA desaturase-1 inhibitors, thyroid hormone receptor R agonists, tumor necrosis factor alpha (TNF-alpha) ligand inhibitors, transglutaminase inhibitors, transglutaminase inhibitor precursors, and combinations thereof. In some specific embodiments, the one or more active agents can be chosen from acetylsalicylic acid, alipogene tiparvovec, aramchol, atorvastatin, BLX-1002, cenicriviroc, cobiprostone, colesevelam, emricasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, PX-102, remogliflozin etabonate, SHP-626, solithromycin, tipelukast, TRX-318, ursodeoxycholic acid, VBY-376, and combinations thereof. In some embodiments, the one or more active agents are present in a therapeutically effective amount for treating a non-alcoholic fatty liver disease (e.g., NASH). In some embodiments, the one or more active agents are present in a therapeutically effective amount for treating a metabolic disease (e.g., obesity and/or diabetes).

Method of Treatment

The spirolactone compounds of the present disclosure are useful for inhibiting ACC1 and/or ACC2 activities in a cell and for treating diseases or disorders associated with ACC1 and/or ACC2 activities (e.g., a metabolic disease, a disease associated with aberrant sebum production, or a non-alcoholic fatty liver disease).

In some embodiments, the present disclosure provides a method of inhibiting ACC1 and/or ACC2 activities in a cell. In some embodiments, the method comprises contacting the cell with an effective amount of a spirolactone compound of the present disclosure or a pharmaceutical composition described herein. In some embodiments, the cell can be in vitro (e.g., a human cell line), in vivo (e.g., a human cell in a human subject), or ex vivo (a human cell from a human subject). In vivo inhibition of ACC1 and/or ACC2 activities can be detected, or presumed if administered systemically and the blood concentration (or administered locally and the localized concentration) of the respective compound is at about or above its respective $IC_{50}$ value (after taking into account of protein binding).

In some embodiments, inhibition of ACC1 and/or ACC2 activities can also lead to inhibition of malonyl-CoA production in a cell, lipogenesis, proliferation of cells, differentiation of fibroblast to adipocytes, sebum production, and/or inflammation, which is implicated in diseases or disorders such as diseases or disorders associated with aberrant sebocyte and/or keratinocyte activity (e.g., acne, and others as described herein), metabolic diseases (e.g., obesity, diabetes, and others as described herein), non-alcohol fatty liver disease (e.g., NASH), and cancer.

Thus, in some embodiments, the present disclosure provides a method of inhibiting lipogenesis in a cell. In some embodiments, the method comprises contacting the cell (e.g., a human cell) with an effective amount of a spirolactone compound of the present disclosure or a pharmaceutical composition described herein. In some embodiments, the cell is a sebocyte, adipocyte, or a hepatocyte.

In some embodiments, the present disclosure provides a method of inhibiting proliferation of cells. In some embodiments, the method comprises contacting the cells (e.g., human cells) with an effective amount of a spirolactone compound of the present disclosure or a pharmaceutical composition described herein. In some embodiments, the cells are adipocytes, melanocytes, keratinocytes, squamous cells, Merkel cells, Langerhans cells, and/or skin stem cells. In some embodiments, the cells are adipocytes, melanocytes, keratinocytes, squamous cells, Merkel cells, Langerhans cells, and/or skin stem cells in epidermis, dermis, and/or hypodermis. In some embodiments, the cells are human sebocytes. In some embodiments, the cells are human keratinocytes.

In some embodiments, the present disclosure provides a method of inhibiting differentiation of fibroblast (e.g., human fibroblast) to adipocytes. In some embodiments, the method comprises contacting the fibroblast with an effective amount of a spirolactone compound of the present disclosure or a pharmaceutical composition described herein. In some embodiments, the method inhibits the differentiation of fibroblast to adipocytes in cutaneous and/or subcutaneous layers.

In some embodiments, the present disclosure provides a method of inhibiting sebum production. In some embodiments, the method comprises contacting a sebocyte (e.g., a human sebocyte) with an effective amount of a spirolactone compound of the present disclosure or a pharmaceutical composition described herein.

In some embodiments, the present disclosure also provides a method of inhibiting ACC1 and/or ACC2 activities and one or more (e.g., 1, 2, 3, 4, 5, 6, or all) activities in a subject (e.g., a human subject) in need thereof, wherein the one or more activities are chosen from (a) lipogenesis (e.g., lipogenesis of sebocytes, lipogenesis of adipocytes, lipogenesis of hepaocytes, etc.) in the subject; (b) proliferation of cells, such as adipocytes, melanocytes, keratinocytes, squamous cells, Merkel cells, Langerhans cells, or skin stem cells, in epidermis, dermis, and/or hypodermis in the subject; (c) proliferation of human sebocytes in the subject; (d) proliferation of human keratinocytes in the subject; (e) differentiation of fibroblast to adipocytes in cutaneous and/or subcutaneous layers in the subject; (f) sebum production in the subject; (g) inflammation in the subject, and combinations thereof, the method comprises administering to the subject an effective amount of a spirolactone compound of the present disclosure or a pharmaceutical composition described herein. In some embodiments, the subject is characterized as having a disease or disorder chosen from acne, seborrhea, sebaceous hyperplasia, seborrheic keratosis, sebaceous adenoma, sebaceous cyst, actinic keratosis, sebaceous carcinoma, squamous cell carcinoma, melanoma, phymatous rosacea, fibrofolliculomas in Birt-Hogg-Dube syndrome, and combinations thereof.

In some embodiments, the present disclosure also provides a method of treating a disease or disorder associated with ACC1 and/or ACC2 in a subject in need thereof. In some embodiments, the method comprises administering to the subject a therapeutically effective amount of a spirolactone compound of the present disclosure or a pharmaceutical composition described herein. Various diseases or disorders are associated with undesired or aberrant (e.g., hyperactive) ACC1 and/or ACC2 activities and can be treated by the methods described herein.

Method of Treating Skin Diseases

Skin is the largest organ of human body that provides the interface between the external environment and the host. Lipids play an essential role in the formation and maintenance of both the permeability and antimicrobial barriers of skin. The normal function of skin is maintained by the hydrophobic extracellular lipid matrix in the stratum corneum composed primarily of ceramides, cholesterol, and free fatty acids, which prevents loss of water and electrolytes in the body. Sebaceous gland is the organ producing and secreting sebum into the follicular duct, which reaches the skin's surface to maintain the normal function of the skin as barriers.

Acne vulgaris (acne) is a common dermatological condition affecting many people. Acne is a chronic inflammatory dermatosis notable for open or closed comedones (blackheads and whiteheads) and inflammatory lesions, including papules, pustules, or nodules (also known as cysts). Zaenglein, A. et al., J. Am. Acad. Dermatol, 74:945-73 (2016). Key pathogenic factors that play an important role in the development of acne are follicular hyperkeratinization, microbial colonization with *Propionibacterium acnes*, sebum production, and complex inflammatory mechanisms involving both innate and acquired immunity. Acne can have different severities, such as mild, moderate, and severe. The severity of the condition is affected by multiple factors including seasonal and psychological influences.

A wide array of therapies for treating acne such as moderate to severe acne is available. See e.g., Zaenglein, A. et al., J. Am. Acad. Dermatol, 74:945-73 (2016). These therapies include, for example, (1) antibiotics (oral or topical), such as tetracycline, doxycycline, minocycline, trimethoprim/sulfamethoxazole (TMP/SMX), trimethoprim, erythromycin, clindamycin, azelaic acid, dapsone, azithromycin, amoxicillin, and cephalexin; (2) hormonal agents, such as combined oral contraceptives with an estrogen and a progestin, for example, ethinyl estradiol/norgestimate, ethinyl estradiol/norethindrone acetate/ferrous fumarate, ethinyl estradiol/drospirenone, and ethinyl estradiol/drospirenone/levomefolate; (3) oral retinoid, such as oral isotretinoin, (Accutane®, 13-cis-retinoic acid); (4) topical treatment, such as benzoyl peroxide (BP), salicylic acid, antibiotics, combination of antibiotics with BP, retinoids (e.g., tretinoin, adapalene, tazarotene), retinoid with BP, retinoid with antibiotic, azelaic acid, and sulfone agents (e.g., dapsone) etc.; and (5) others, such as spironolactone, flutamide, intralesional corticosteroid (triamcinolone acetonide), glycolic acid peels, salicylic acid peels, and resorcinol and salicylic acid. However, there are significant deficiencies in the currently available therapies for acne. Dermatological therapies are not fully effective against acne such as mild to moderate acne and many of the agents employed in these therapies produce skin irritation or have other side effects. See e.g., Zaenglein, A. et al., J. Am. Acad. Dermatol, 74:945-73 (2016). For example, Accutane was removed from the U.S. market in 2009 among lawsuits for potential inflammatory bowel disease side effects.

Reducing sebum production as a means to treat acne has also been described, with results indicating that acne could significantly improve with a non-retinoid that inhibits sebum production. See, e.g., U.S. Pat. No. 8,884,034 to Daynard, T. et al. (2014), quoting Zouboulis, C. C. et al., "Zileuton, an oral 5-lipoxygenase inhibitor, directly reduces sebum production", Dermatology (2005), Vol. 210, pp. 36-38; and Zouboulis, C. C. et al., "A new concept for acne therapy: a pilot study with zileuton, an oral 5-lipoxygenase inhibitor", Arch. Dermatol. (2003), Vol. 139, pp. 668-670.

Sebaceous gland is filled with mature sebocytes, which is mainly occupied by lipid droplets in cytosol and undergoes holocrine secretion. To maintain the normal function of sebaceous gland, mature sebocytes is constantly regenerated from epidermal stem cells. Overactivity of sebocytes, including proliferation, differentiation, and production of sebum can cause different skin diseases including acne, seborrhea, sebaceous hyperplasia, seborrheic keratosis, sebaceous adenoma, sebaceous cyst, actinic keratosis, sebaceous carcinoma, squamous cell carcinoma, melanoma, phymatous rosacea, and fibrofolliculomas in Birt-Hogg-Dub6 syndrome, etc.

Although lipid metabolism is active in the skin, expression level and enzymatic activity of ACC in the skin, especially in sebaceous gland is not fully elucidated. It was unknown whether inhibiting ACC1 and/or ACC2 would interfere with the development and progression of the skin diseases mentioned above. US 2016/0220557 discloses ACC inhibitors for treating acne. Recently, a phase 1 acne trial with PF-06423264 was terminated as showing no meaningful pharmacodynamics response. Further, olumacostat glasaretil, although showing positive phase II data, did not meet its primary endpoints in a phase III study. Although it was proposed that olumacostat glasaretil acts as a prodrug of (5-(tetradecyloxy)-2-furancarboxylic acid, a purported ACC inhibitor, the observed effect of olumacostat glasaretil may not be due to ACC inhibition.

The above notwithstanding, the present inventors have found that ACC proteins are abundantly and specifically expressed in sebaceous gland in human skin. This result first shows the localization of ACC proteins in human skin structure and provides evidence suggesting that administering ACC inhibitors to sebaceous gland, e.g., through topical administration of ACC inhibitors, can suppress lipid accumulation and progression of diseases related to overproduction of lipids in sebacytes by inhibiting ACCs in sebaceous gland. Thus, in some embodiments, the spirolactone compounds of the present disclosure can also be used for treating diseases or disorders associated with aberrant sebocyte and/or keratinocyte activities, e.g., through topical administration. As shown in the Examples section, exemplary representative spirolactone compounds of the present disclosure are inhibitors of ACC1 and/or ACC2. Further, exemplary representative spirolactone compounds of the present disclosure were shown to inhibit sebocytes activities such as lipogenesis of sebocytes.

Accordingly, in some embodiments, the present disclosure provides a method of treating a disease or disorder associated with aberrant sebocyte and/or keratinocyte activity in a subject in need thereof. In some embodiments, the method comprises administering to the subject in need thereof a therapeutically effective amount of a spirolactone compound of the present disclosure or a pharmaceutical composition described herein. Non-limiting suitable diseases or disorders associated with aberrant sebocyte and/or keratinocyte activity include, for example, acne, seborrhea, sebaceous hyperplasia, seborrheic keratosis, sebaceous adenoma, sebaceous cyst, actinic keratosis, sebaceous carcinoma, squamous cell carcinoma, melanoma, phymatous rosacea, fibrofolliculomas in Birt-Hogg-Dube syndrome, and a combination thereof. Various routes of administration are suitable, for example, orally or topically. The method can use the spirolactone compound of the present disclosure as the active agent or use it in combination with another therapy. In some embodiments, the spirolactone compound of the present disclosure is the only active agent administered to the subject for treating the disease or disorder associated with aberrant sebocyte and/or keratinocyte activity. In some embodiments, the method is a combination therapy and further comprises treating the subject with one or more additional therapies effective for the treatment of the disease or disorder associated with aberrant sebocyte and/or keratinocyte activity. When used in a combination therapy, the spirolactone compound of the present disclosure can be administered to the subject concurrently with, prior to, or subsequent to the one or more additional therapies. The spirolactone compound of the present disclosure and the one or more additional therapies can be administered to the subject through the same or different routes. For example, in some embodiments, the spirolactone compound of the present disclosure can be administered topically, whereas the one or more additional therapies (e.g., additional active agents) can be administered orally.

In some specific embodiments, the present disclosure provides a method of treating acne in a subject in need thereof. In some embodiments, the method comprises administering (e.g., topically) to the subject in need thereof a therapeutically effective amount of a spirolactone compounds of the present disclosure or a pharmaceutical composition described herein. In some embodiments, the method is a combination therapy and further comprises treating the subject with an additional therapy for acne. Any of the known therapies for treating acne can be part of the combination therapy, some of which are exemplified herein. For example, in some embodiments, the method further comprises administering to the subject an antibiotic, either topically or systemically, a retinoid, either topically or systemically, or a combination thereof. In some embodiments, the antibiotic is clindamycin, erythromycin, metronidazole, sulfacetamide, a tetracycline such as doxycycline and minocycline, or a combination thereof. In some embodiments, the retinoid is adapalene, isotretinoin, retinol, tazarotene, tretinoin, or a combination thereof. Other suitable antibiotics and retinoids are known in the art and exemplified herein.

Method of Treating Other Diseases

Inhibitions of ACC1 and/or ACC2 activities have also been found to be associated with and/or useful for treating various metabolic diseases, non-alcoholic fatty liver diseases, and/or cancer. See e.g., U.S. Pat. No. 8,288,405 and Griffith et al., Journal of medicinal chemistry 57:10512-10526(2014) (obesity, diabetes); Harriman et al., Proceedings of the National Academy of Sciences of the United States of America 113:E1796-1805(2016) (nonalcoholic steatohepatitis (NASH), and Svensson et al., Nature medicine 22, 1108-1119(2016) (cancer).

Accordingly, certain embodiments of the present disclosure are directed to the use of the spirolactone compounds of the present disclosure or pharmaceutical composition described herein, for the treatment of metabolic diseases, non-alcoholic fatty liver diseases, and/or cancer. Various routes of administration are suitable, for example, orally or topically. The method can use the spirolactone compound of the present disclosure as the active agent or use it in combination with another therapy. In some embodiments, the spirolactone compound of the present disclosure is the only active agent administered to the subject for treating the metabolic diseases, non-alcoholic fatty liver diseases, and/or cancer. In some embodiments, the method is a combination therapy and further comprises treating the subject with one or more additional therapies effective for the treatment of the metabolic diseases, non-alcoholic fatty liver diseases, and/or cancer. When used in a combination therapy, the spirolactone compound of the present disclosure can be administered to the subject concurrently with, prior to, or subsequent to the one or more additional therapies. The spirolactone compound of the present disclosure and the one or more additional therapies can be administered to the subject through the same or different routes. For example, in some embodiments, the spirolactone compound of the present disclosure can be administered topically, whereas the one or more additional therapies (e.g., active agents) can be administered orally.

In some specific embodiments, the present disclosure provides a method of treating obesity and/or obesity-related disorders (e.g., overweight, weight gain, or weight maintenance) in a subject (e.g., human subject) in need thereof. Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998). In some embodiments, the method comprises administering (e.g., orally) to the subject in need thereof a therapeutically effective amount of a spirolactone compounds of the present disclosure or a pharmaceutical composition described herein.

In some embodiments, the present disclosure also provides a method of treating diabetes and/or diabetes-related disorders in a subject (e.g., human subject) in need thereof, such as Type 1 (insulin-dependent diabetes mellitus, also referred to as "IDDM") and Type 2 (noninsulin-dependent diabetes mellitus, also referred to as "NIDDM") diabetes etc. In some embodiments, the method comprises administering (e.g., orally) to the subject in need thereof a therapeutically effective amount of a spirolactone compounds of the present disclosure or a pharmaceutical composition described herein.

In some embodiments, the present disclosure also provides a method of treating a non-alcoholic fatty liver disease in a subject (e.g., human subject) in need thereof, for example, NASH. In some embodiments, the method comprises administering (e.g., orally) to the subject in need thereof a therapeutically effective amount of a spirolactone compound of the present disclosure (e.g., a compound of Formula Ic, or Examples 14-22) or a pharmaceutical composition described herein.

In some embodiments, the methods of treating obesity, obesity-related disorders, diabetes, diabetes-related disorders, and/or non-alcoholic fatty liver diseases can be a combination therapy. For example, the methods can include administering to the subject one or more additional active agents in a therapeutically effective amount for treating the respective disease or disorder. Non-limiting useful agents for the combination therapy include angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacyl glycerol O-acyltransferase 1 (DGAT1) inhibitors, dipeptidyl peptidase IV (DPPIV) inhibitors, farnesoid X receptor (FXR) agonists, galectin-3 inhibitors, glucagon-like peptide 1 (GLP1) agonists, glutathione precursors, hepatitis C virus NS3 protease inhibitors, HMG CoA reductase inhibitors, 11β-hydroxysteroid dehydrogenase (11β-HSD1) inhibitors, IL-1β antagonists, IL-6 antagonists, IL-10 agonists, IL-17 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPAR-alpha agonists, PPAR-gamma agonists, PPAR-delta agonists, Rho associated protein kinase 2 (ROCK2) inhibitors, sodium glucose transporter-2 (SGLT2) inhibitors, stearoyl CoA desaturase-1 inhibitors, thyroid hormone receptor R agonists, tumor necrosis factor alpha (TNF-alpha) ligand inhibitors, transglutaminase inhibitors, transglutaminase inhibitor precursors, and combinations thereof. For example, in some embodiments, the one or more additional agents can be chosen from acetylsalicylic acid, alipogene tiparvovec, aramchol, atorvastatin, BLX-1002, ceniciriviroc, cobiprostone, colesevelam, emricasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, PX-102, remogliflozin etabonate, SHP-626, solithromycin, tipelukast, TRX-318, ursodeoxycholic acid, VBY-376, and combinations thereof.

In some embodiments, the present disclosure also provides a method of treating cancer.

Exemplary Embodiments

The present disclosure also provides the following exemplary embodiments E1-E52.

1. A compound of Formula I, or a pharmaceutically acceptable salt thereof,

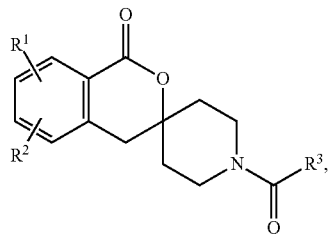

Formula I wherein:
R$^1$ and R$^2$ are each independently hydrogen, halogen, cyano, an optionally substituted C$_{1-6}$ alkyl, an optionally substituted C$_{3-6}$ cycloalkyl, an optionally substituted C$_{2-6}$ alkenyl, an optionally substituted C$_{2-6}$ alkynyl, an optionally substituted C$_{6-10}$ aryl, an optionally substituted 5-10 membered heteroaryl, an optionally substituted 4-6 membered heterocyclyl, NR$^{10}$R$^{11}$, COOR$^{12}$, CONR$^{13}$R$^{14}$, CN, S(O)$_n$R$^{15}$, or OR$^{16}$; wherein
R$^{10}$ and R$^{11}$ are each independently hydrogen, an optionally substituted C$_{1-6}$ alkyl, an optionally substituted C$_{3-6}$ cycloalkyl, an optionally substituted C$_{1-6}$ alkanoyl, an optionally substituted C$_{3-6}$ cycloalkanoyl, an optionally substituted C$_{6-10}$ aryl, an optionally substituted 5-10 membered heteroaryl, an optionally substituted 4-6 membered heterocyclyl, COOR$^{12}$, or CONR$^{13}$R$^{14}$.
R$^{12}$, R$^{13}$ and R$^{14}$ are each independently hydrogen or an optionally substituted C$_{1-6}$ alkyl;
n is 0, 1, or 2;
R$^{15}$ is an optionally substituted C$_{1-6}$ alkyl, an optionally substituted C$_{3-6}$ cycloalkyl, or NR$^{10}$R$^{11}$;
R$^{16}$ is hydrogen, an optionally substituted C$_{1-6}$ alkyl, an optionally substituted C$_{3-6}$ cycloalkyl, an optionally substituted C$_{1-6}$ alkanoyl, an optionally substituted C$_{3-6}$ cycloalkanoyl, an optionally substituted C$_{6-10}$ aryl, an optionally substituted 5-10 membered heteroaryl, an optionally substituted 4-6 membered heterocyclyl or CONR$^{13}$R$^{14}$;
and R$^3$ is an optionally substituted C$_{6-10}$ aryl or optionally substituted 5-10 membered heteroaryl,
provided that when R and R$^2$ are both hydrogen, then R$^3$ is not an optionally substituted phenyl.

2. The compound of E1, or pharmaceutically acceptable salt thereof, wherein R$^1$ is halogen, an optionally substituted C$_{1-6}$ alkyl, an optionally substituted C$_{1-6}$ alkoxy, an optionally substituted C$_{3-6}$ cycloalkyl, or an optionally substituted C$_{3-6}$ cycloalkoxy.

3. The compound of E1 or 2, or pharmaceutically acceptable salt thereof, wherein R$^1$ is C$_1$–4 alkyl, C$_{1-4}$ alkoxy, C$_{3-6}$ cycloalkyl, or C$_{3-6}$ cycloalkoxy, each optionally substituted with 1-3 substituents independently chosen from halogen and C$_{1-4}$ alkyl.

4. The compound of any one of E1-3, or pharmaceutically acceptable salt thereof, wherein R$^1$ is C$_{1-4}$ alkyl or C$_{1-4}$ alkoxy, each optionally substituted with 1-3 fluorines.

5. The compound of E1, or pharmaceutically acceptable salt thereof, wherein R$^1$ is a 5-10 membered heteroaryl optionally substituted with 1 or 2 substituents independently chosen from halogen, cyano, optionally substituted C$_{1-4}$ alkyl, optionally substituted C$_{1-4}$ alkoxy, optionally substituted C$_{3-6}$ cycloalkyl, and optionally substituted C$_{3-6}$ cycloalkoxy.

6. The compound of E1, or pharmaceutically acceptable salt thereof, wherein R$^1$ is a 4-6 membered heterocyclyl optionally substituted with 1 or 2 substituents independently chosen from halogen, oxo, optionally substituted C$_{1-4}$ alkyl, optionally substituted C$_{1-4}$ alkoxy, optionally substituted C$_{3-6}$ cycloalkyl, and optionally substituted C$_{3-6}$ cycloalkoxy.

7. The compound of E1, or pharmaceutically acceptable salt thereof, wherein R$^1$ is NR$^{10}$R$^{11}$.

8. The compound of E7, or pharmaceutically acceptable salt thereof, wherein one of R$^{10}$ and R$^{11}$ is an optionally substituted phenyl or optionally substituted 5 or 6 membered heteroaryl.

9. The compound of E7, or pharmaceutically acceptable salt thereof, wherein one of R$^{10}$ and R$^{11}$ is a 5-membered heteroaryl optionally substituted with 1 or 2 substituents independently chosen from halogen, cyano and C$_{1-4}$ alkyl.

10. The compound of E7, or pharmaceutically acceptable salt thereof, wherein one of R$^{10}$ and R$^{11}$ is a 5-membered heteroaryl having 2-4 ring nitrogen atoms, which is optionally substituted with 1 or 2 substituents independently chosen from halogen, cyano and C$_{1-4}$ alkyl.

11. The compound of E7, or pharmaceutically acceptable salt thereof, wherein one of R$^{10}$ and R$^{11}$ is a pyrazolyl, triazolyl or tetrazolyl, each optionally substituted with 1 or 2 independently chosen C$_{1-4}$ alkyl.

12. The compound of any one of E1-11, or pharmaceutically acceptable salt thereof, wherein R$^2$ is H.

13. The compound of any one of E1-12, or pharmaceutically acceptable salt thereof, wherein R$^3$ is a C$_{6-10}$ aryl optionally substituted with 1-3 substituents independently chosen from halogen, optionally substituted C$_{1-4}$ alkyl, optionally substituted C$_{1-4}$ alkoxy, optionally substituted C$_{3-6}$ cycloalkyl, and optionally substituted C$_{3-6}$ cycloalkoxy.

14. The compound of any one of E1-12, or pharmaceutically acceptable salt thereof, wherein R$^3$ is an optionally substituted 8-10 membered bicyclic heteroaryl.

15. The compound of any one of E1-12, or pharmaceutically acceptable salt thereof, wherein R$^3$ is a naphthyl or quinolinyl, each optionally substituted with 1-3 substituents independently chosen from halogen, cyano, C$_{1-4}$ alkyl optionally substituted with 1-3 halogens, C$_{1-4}$ alkoxy optionally substituted with 1-3 halogens, C$_{3-6}$ cycloalkyl optionally substituted with 1-3 halogens, and C$_{3-6}$ cycloalkoxy optionally substituted with 1-3 halogens.

16. The compound of any one of E1-12, or pharmaceutically acceptable salt thereof, wherein R$^3$ is a naphthyl or quinolinyl, each optionally substituted with 1-3 substituents independently chosen from fluoro, chloro, hydroxyl, methyl, ethyl, trifluoromethyl, trifluoromethoxy, methoxy, ethoxy, and cyclopropyl.

17. A compound of Formula Ia, or a pharmaceutically acceptable salt thereof,

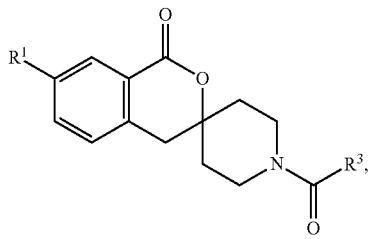

Formula Ia

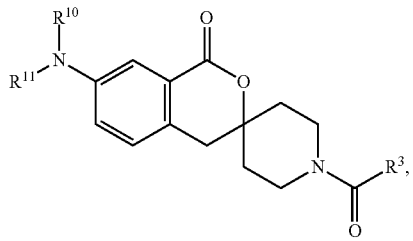

Formula Ib wherein:
- $R^1$ is hydrogen, halogen, cyano, an optionally substituted $C_{1-6}$ alkyl, an optionally substituted $C_{3-6}$ cycloalkyl, an optionally substituted $C_{2-6}$ alkenyl, an optionally substituted $C_{2-6}$ alkynyl, an optionally substituted $C_{6-10}$ aryl, an optionally substituted 5-10 membered heteroaryl, an optionally substituted 4-6 membered heterocyclyl, $NR^{10}R^{11}$, $COOR^{12}$, $CONR^{13}R^{14}$, CN, $S(O)_n R$, or $OR^{16}$;

wherein
$R^{10}$ and $R^{11}$ are each independently hydrogen, an optionally substituted $C_{1-6}$ alkyl, an optionally substituted $C_{3-6}$ cycloalkyl, an optionally substituted $C_{1-6}$ alkanoyl, an optionally substituted $C_{3-6}$ cycloalkanoyl, an optionally substituted $C_{6-10}$ aryl, an optionally substituted 5-10 membered heteroaryl, an optionally substituted 4-6 membered heterocyclyl, $COOR^{12}$, or $CONR^{13}R^14$.

$R^{12}$, $R^{13}$ and $R^{14}$ are each independently hydrogen or an optionally substituted $C_{1-6}$ alkyl;

n is 0, 1, or 2;

$R^{15}$ is an optionally substituted $C_{1-6}$ alkyl, an optionally substituted $C_{3-6}$ cycloalkyl, or $NR^{10}R^{11}$;

$R^{16}$ is hydrogen, an optionally substituted $C_{1-6}$ alkyl, an optionally substituted $C_{3-6}$ cycloalkyl, an optionally substituted $C_{1-6}$ alkanoyl, an optionally substituted $C_{3-6}$ cycloalkanoyl, an optionally substituted $C_{6-10}$ aryl, an optionally substituted 5-10 membered heteroaryl, an optionally substituted 4-6 membered heterocyclyl or $CONR^{13}R^{14}$;

and $R^3$ is an optionally substituted $C_{6-10}$ aryl or optionally substituted 5 to 10 membered heteroaryl, provided that when $R^1$ is hydrogen, then $R^3$ is not an optionally substituted phenyl.

18. The compound of E17, or pharmaceutically acceptable salt thereof, wherein $R^1$ is an optionally substituted $C_{1-4}$ alkyl.

19. The compound of E17 or 18, or pharmaceutically acceptable salt thereof, wherein $R^1$ is methyl, ethyl, isopropyl, or tert-butyl.

20. The compound of E17, or pharmaceutically acceptable salt thereof, wherein $R^1$ is an optionally substituted $C_{1-4}$ alkoxy.

21. The compound of E20, or pharmaceutically acceptable salt thereof, wherein $R^1$ is methoxy, trifluoromethoxy, ethoxy or isopropoxy.

22. The compound of E17 having Formula Ib, or pharmaceutically acceptable salt thereof, wherein one of $R^{10}$ and $R^{11}$ is an optionally substituted phenyl or optionally substituted 5 or 6 membered heteroaryl.

23. The compound of E22, or pharmaceutically acceptable salt thereof, wherein one of $R^{10}$ and $R^{11}$ is an optionally substituted 5 or 6 membered heteroaryl.

24. The compound of E22, or pharmaceutically acceptable salt thereof, wherein one of $R^{10}$ and $R^{11}$ is a 5-membered heteroaryl having 2-4 ring nitrogen atoms, which is optionally substituted with 1 or 2 substituent chosen from halogen, cyano and $C_{1-4}$ alkyl.

25. The compound of E22, or pharmaceutically acceptable salt thereof, wherein one of $R^{10}$ and $R^{11}$ is a pyrazolyl, triazolyl or tetrazolyl, each optionally substituted with a $C_{1-4}$ alkyl.

26. The compound of E22, or pharmaceutically acceptable salt thereof, wherein one of $R^{10}$ and $R^{11}$ is

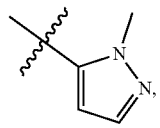

and the other of $R^{10}$ and $R^{11}$ is hydrogen or methyl.

27. The compound of any one of E17-26, or pharmaceutically acceptable salt thereof, wherein $R^3$ is a $C_{6-10}$ aryl optionally substituted with 1-3 substituents independently chosen from halogen, cyano, optionally substituted $C_{1-4}$ alkyl, optionally substituted $C_{1-4}$ alkoxy, optionally substituted $C_{3-6}$ cycloalkyl, and optionally substituted $C_{3-6}$ cycloalkoxy.

28. The compound of any one of E17-26, or pharmaceutically acceptable salt thereof, wherein $R^3$ is an optionally substituted 8-10 membered bicyclic heteroaryl.

29. The compound of any one of E17-26, or pharmaceutically acceptable salt thereof, wherein $R^3$ is a naphthyl or quinolinyl optionally substituted with 1-3 substituents independently chosen from halogen, cyano, $C_{1-4}$ alkyl optionally substituted with 1-3 halogens, $C_{1-4}$ alkoxy optionally substituted with 1-3 halogens, $C_{3-6}$ cycloalkyl optionally substituted with 1-3 halogens, and $C_{3-6}$ cycloalkoxy optionally substituted with 1-3 halogens.

30. The compound of any one of E17-26, or pharmaceutically acceptable salt thereof, wherein $R^3$ is

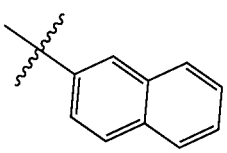 or 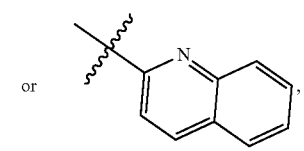, each optionally substituted with 1-3 substituents independently chosen from fluoro, chloro, hydroxyl, methyl, trifluoromethyl, ethyl, methoxy, trifluoromethoxy, ethoxy, and cyclopropyl.

31. The compound of any one of E17-26, or pharmaceutically acceptable salt thereof, wherein $R^3$ is

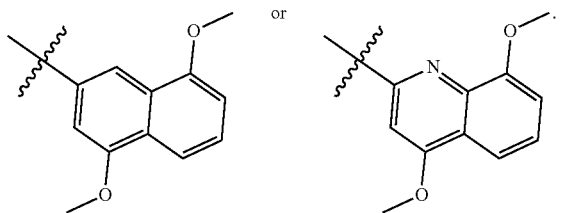 [SMILES: *c1cc(OC)c2cccc(OC)c2c1 ; *c1cc(OC)c2cccc(OC)c2n1]

32. The compound of any one of E17-26, or pharmaceutically acceptable salt thereof, wherein the compound is chosen from:

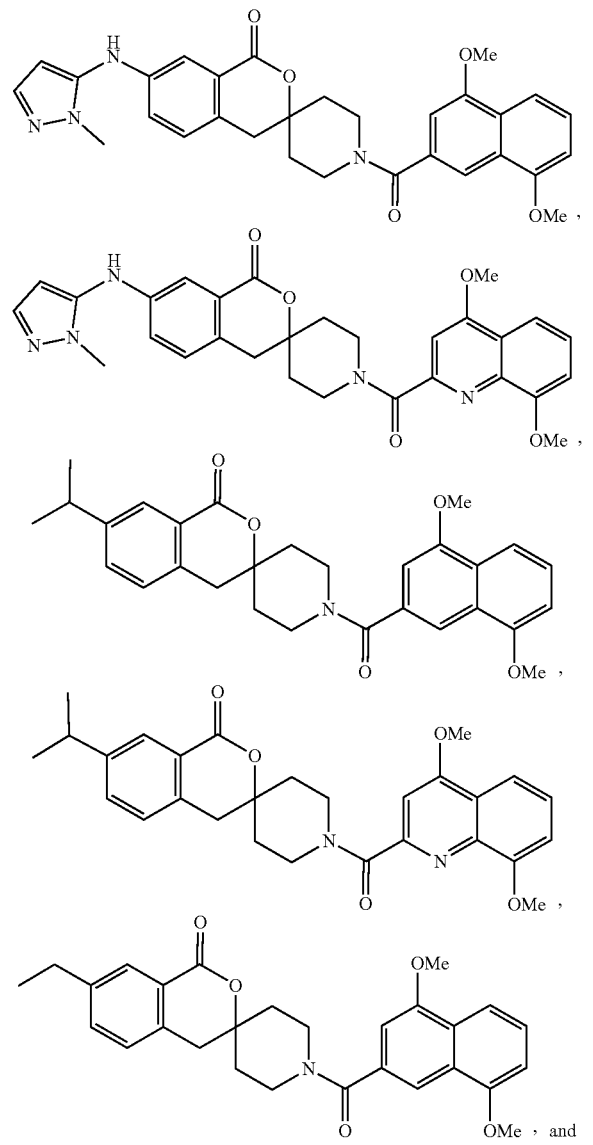

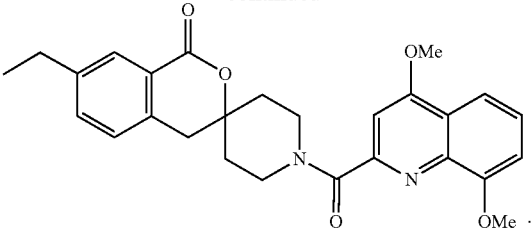

33. A pharmaceutical composition comprising a compound of any one of E1-32, or a pharmaceutically acceptable salt thereof, and a pharmaceutically acceptable excipient.

34. The pharmaceutical composition of E33, formulated for intravenous injection or infusion, oral administration, inhalation, or topical administration.

35. The pharmaceutical composition of E33 or 34, formulated in the form of a topical solution, lotion, shampoo, transdermal spray, topical film, foam, powder, paste, sponge, transdermal patch, tincture, tape, cream, gel, or ointment.

36. The pharmaceutical composition of any one of E33-35, comprising an amount of the compound of any one of E1-32, or pharmaceutically acceptable salt thereof, effective for inhibiting one or more activities in a human in need thereof, wherein the one or more activities are chosen from acetyl-CoA carboxylases ACC1 and/or ACC2 activities, lipogenesis, proliferation of cells (e.g., adipocytes, melanocytes, keratinocytes, squamous cells, Merkel cells, Langerhans cells, or skin stem cells) in epidermis, dermis, and/or hypodermis, proliferation of human sebocytes, proliferation of human keratinocytes, differentiation of fibroblast to adipocytes in cutaneous and/or subcutaneous layers, sebum production, inflammation, and combinations thereof.

37. A method of inhibiting one or more activities in a subject in need thereof, wherein the one or more activities are chosen from acetyl-CoA carboxylases (ACC1 and/or ACC2) activities, malonyl-CoA production, lipogenesis, proliferation of sebocytes, proliferation of keratinocytes, proliferation of cells (e.g., adipocytes, melanocytes, keratinocytes, squamous cells, Merkel cells, Langerhans cells, and skin stem cells) in epidermis, dermis, and/or hypodermis, differentiation of fibroblast to adipocytes in cutaneous and/or subcutaneous layers, inflammation, and combinations thereof, the method comprising administering to the subject a therapeutically effective amount of a compound of any one of E1-32, or a pharmaceutically acceptable salt thereof, or a pharmaceutical composition of any one of E33-36.

38. The method of E37, wherein the compound of any one of E1-32, or pharmaceutically acceptable salt thereof, or pharmaceutical composition of any one of E33-36 is administered to the subject topically.

39. A method of treating a disease or disorder associated with aberrant sebocyte and/or keratinocyte activity in a subject in need thereof, the method comprising administering to the subject a therapeutically effective amount of a compound of any one of E1-32, or a pharmaceutically acceptable salt thereof, or a pharmaceutical composition of any one of E33-36.

40. The method of E39, wherein the disease or disorder is acne, seborrhea, sebaceous hyperplasia, seborrheic keratosis, actinic keratosis, sebaceous adenoma, sebaceous cyst, sebaceous carcinoma, squamous cell carcinoma, melanoma, phymatous rosacea, fibrofolliculomas in Birt-Hogg-Dube syndrome, or a combination thereof.

41. The method of E39 or 40, wherein the disease or disorder is acne.
42. The method of any one of E39-41, wherein the compound of any one of E1-32, or pharmaceutically acceptable salt thereof, or pharmaceutical composition of any one of E33-36 is administered to the subject topically.
43. The method of any one of E39-42, further comprising treating the subject with one or more additional therapies effective for the treatment of the disease or disorder associated with aberrant sebocyte and/or keratinocyte activity.
44. The method of any one of E39-42, further comprising administering to the subject an antibiotic (e.g., clindamycin, erythromycin, metronidazole, sulfacetamide, or tetracyclines such as doxycycline and minocycline) or retinoid (e.g., adapalene, isotretinoin, retinol, tazarotene, or tretinoin) in a therapeutically effective amount for treating acne and/or inflammation.
45. A method for treating non-alcoholic fatty liver disease (e.g., non-alcoholic steatohepatitis (NASH)) in a subject in need thereof, the method comprises administering to the subject a therapeutically effective amount of a compound of any one of E1-32, or a pharmaceutically acceptable salt thereof, or a pharmaceutical composition of any one of E33-36.
46. The method of E45, further comprising administering to the subject one or more additional agents in a therapeutically effective amount for treating the non-alcoholic fatty liver disease.
47. The method of E46, wherein the one or more additional agents are chosen from angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacyl glycerol O-acyltransferase 1 (DGAT1) inhibitors, dipeptidyl peptidase IV (DPPIV) inhibitors, farnesoid X receptor (FXR) agonists, galectin-3 inhibitors, glucagon-like peptide 1 (GLP1) agonists, glutathione precursors, hepatitis C virus NS3 protease inhibitors, HMG CoA reductase inhibitors, 11β-hydroxysteroid dehydrogenase (11β-HSD1) inhibitors, IL-1β antagonists, IL-6 antagonists, IL-10 agonists, IL-17 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPAR-alpha agonists, PPAR-gamma agonists, PPAR-delta agonists, Rho associated protein kinase 2 (ROCK2) inhibitors, sodium glucose transporter-2 (SGLT2) inhibitors, stearoyl CoA desaturase-1 inhibitors, thyroid hormone receptor R agonists, tumor necrosis factor alpha (TNF-alpha) ligand inhibitors, transglutaminase inhibitors, transglutaminase inhibitor precursors, and combinations thereof.
48. The method of any one of E46-47, wherein the one or more additional agents are chosen from acetylsalicylic acid, alipogene tiparvovec, aramchol, atorvastatin, BLX-1002, cenicriviroc, cobiprostone, colesevelam, emricasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, PX-102, remogliflozin etabonate, SHP-626, solithromycin, tipelukast, TRX-318, ursodeoxycholic acid, VBY-376, and combinations thereof.
49. A method for treating obesity and/or diabetes in a subject in need thereof, the method comprises administering to the subject a therapeutically effective amount of a compound of any one of E1-32, or a pharmaceutically acceptable salt thereof, or a pharmaceutical composition of any one of E33-36.
50. The method of E49, further comprising administering to the subject one or more additional agents in a therapeutically effective amount for treating obesity and/or diabetes.
51. The method of E50, wherein the one or more additional agents are chosen from angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacyl glycerol O-acyltransferase 1 (DGAT1) inhibitors, dipeptidyl peptidase IV (DPPIV) inhibitors, farnesoid X receptor (FXR) agonists, galectin-3 inhibitors, glucagon-like peptide 1 (GLP1) agonists, glutathione precursors, hepatitis C virus NS3 protease inhibitors, HMG CoA reductase inhibitors, 11θ-hydroxysteroid dehydrogenase (11θ-HSD1) inhibitors, IL-1β antagonists, IL-6 antagonists, IL-10 agonists, IL-17 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPAR-alpha agonists, PPAR-gamma agonists, PPAR-delta agonists, Rho associated protein kinase 2 (ROCK2) inhibitors, sodium glucose transporter-2 (SGLT2) inhibitors, stearoyl CoA desaturase-1 inhibitors, thyroid hormone receptor R agonists, tumor necrosis factor alpha (TNF-alpha) ligand inhibitors, transglutaminase inhibitors, transglutaminase inhibitor precursors, and combinations thereof.
52. The method of any one of E50-51, wherein the one or more additional agents are chosen from acetylsalicylic acid, alipogene tiparvovec, aramchol, atorvastatin, BLX-1002, cenicriviroc, cobiprostone, colesevelam, emricasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, PX-102, remogliflozin etabonate, SHP-626, solithromycin, tipelukast, TRX-318, ursodeoxycholic acid, VBY-376, and combinations thereof.

Definitions

It is meant to be understood that proper valences are maintained for all moieties and combinations thereof.

It is also meant to be understood that a specific embodiment of a variable moiety herein may be the same or different as another specific embodiment having the same identifier.

Suitable groups for $R^1$, $R^2$, and $R^3$ in compounds of Formula I (e.g., Formula I-1, Formula Ia, Formula Ib, Formula Ic, Formula II-1 to Formula II-3, or Formula III-1 to Formula III-6) are independently selected. The described embodiments of the present invention may be combined. Such combination is contemplated and within the scope of the present invention. For example, it is contemplated that embodiments for any of $R^1$, $R^2$, and $R^3$ can be combined with embodiments defined for any other of $R^1$, $R^2$, and $R^3$.

The symbol, ⌇ whether utilized as a bond or displayed perpendicular to (or otherwise crossing) a bond, indicates the point at which the displayed moiety is attached to the remainder of the molecule.

As used herein, the term "spirolactone compound(s) of the present disclosure" refers to any of the compounds described herein according to Formula I (e.g., Formula I-1, Formula Ia, Formula Ib, Formula Ic, Formula II-1 to Formula II-3, or Formula III-1 to Formula III-6, or any of Examples 1-22), isotopically labeled compound(s) thereof, possible stereoisomers thereof (including diastereoisomers, enantiomers, and racemic mixtures), tautomers thereof, conformational isomers thereof, and/or pharmaceutically acceptable salts thereof (e.g., acid addition salt such as HCl salt or base addition salt such as Na salt). Hydrates and solvates of the spirolactone compounds of the present disclosure are considered compositions of the present disclosure, wherein the compound(s) is in association with water or solvent, respectively.

As used herein, the phrase "administration" of a compound, "administering" a compound, or other variants thereof means providing the compound or a prodrug of the compound to the individual in need of treatment.

As used herein, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is a straight chain $C_{1-10}$ alkyl group. In another embodiment, the alkyl group is a branched chain $C_{3-10}$ alkyl group. In another embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. In another embodiment, the alkyl group is a branched chain $C_{3-4}$ alkyl group. In another embodiment, the alkyl group is a straight or branched chain $C_{3-4}$ alkyl group. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

As used herein, the term "optionally substituted alkyl" as used by itself or as part of another group means that the alkyl as defined above is either unsubstituted or substituted with one or more (e.g., one, two, or three) substituents each independently chosen from, e.g., halo (e.g., F), oxo, nitro, cyano, $OR^a$, $CO_2R^a$, $OCO_2R^a$, $OSO_2NR^bR^c$, $SO_3R^a$, $OSO_3R^a$, $OS(O)_nR^c$, $NR^bR^c$, $C(=O)NR^bR^c$, $OC(=O)NR^bR^c$, $SO_2NR^bR^c$, $OC(=O)R^d$, $C(=O)R^d$, $S(O)_nR^c$, $C(=NR^f)NR^bR^c$, alkyl, cycloalkyl, alkenyl, alkynyl, aryl, heteroaryl, and heterocyclyl, wherein each alkyl, cycloalkyl, alkenyl, alkynyl, aryl, heteroaryl, and heterocyclyl is further optionally substituted with 1-5 $R^1$, wherein n is 0, 1, or 2, and $R^a$, $R^b$, $R^c$, $R^d$, $R^e$, $R^f$ and $R^g$ are defined herein. In one embodiment, the optionally substituted alkyl is substituted with three substituents, e.g., three fluorines. In one embodiment, the optionally substituted alkyl is substituted with one substituent. In one embodiment, the optionally substituted alkyl is substituted with two substituents.

As used herein, each of $R^a$, $R^d$ and $R^e$ at each occurrence is independently selected from hydrogen, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^g$ groups.

As used herein, each of $R^b$, $R^e$ and $R^f$ at each occurrence is independently selected from hydrogen, nitro, cyano, $OR^{aa}$, $CO_2R^{aa}$, $SO_3R^{aa}$, $NR^{bb}R^{cc}$, $C(=O)NR^{bb}R^{cc}$, $SO_2NR^{bb}R^{cc}$, $OC(=O)R^{dd}$, $C(=O)R^{dd}$, $S(O)_nR^{cc}$, $C(=NR^{ff})NR^{bb}R^{cc}$, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or $R^b$ and $R^c$, or $R^f$ and one of $R^b$ and $R^c$, are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^g$ groups, wherein n is 0, 1, or 2, and $R^a$, $R^{bb}$, $R^{cc}$, $R^{dd}$, $R^{ee}$ and $R^f$ are defined herein. In some embodiments, at least one of $R^b$ and $R^c$ is chosen from hydrogen, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^g$ groups. In some embodiments, both $R^b$ and $R^c$ are independently chosen from hydrogen, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, wherein each alkyl, alkenyl, alkynyl, carbocyclyl, aryl, and heteroaryl is independently substituted with 0, 1, 2, 3, 4, or 5 $R^g$ groups.

As used herein, $R^g$ at each occurrence is independently selected from halo (e.g., F), nitro, cyano, $OR^{aa}$, $CO_2R^{aa}$, $NR^{bb}R^{cc}$, $C(=O)NR^{bb}R^{cc}$, $SO_2NR^{bb}R^{cc}$, $NR^{bb}(SO_2NR^{bb}R^{cc})$, $OSO_2NR^{bb}R^{cc}$, $NR^{bb}(SO_3R^{aa})$, $SO_3R^{aa}$, $OSO_3R^{aa}$, $NR^{bb}(S(O)_nR^{ee})$, $OSO)_nR^{ee})$, $OC(=O)R^{dd}$, $OCO_2R^{aa}$, $NR^{bb}CO_2R^{aa}$, $OC(=O)NR^{bb}R^{cc}$, $NR^{bb}(C(=O)R^{dd})$, $C(=O)R^{dd}$, $S(O)_nR^{ee}$, $C(=NR^{ff})NR^{bb}R^{cc}$, —$NR^{hh}$—$C(=O)NR^{bb}R^{cc}$, —$NR^{hh}$—$C(=NR^{ff})NR^{bb}R^{cc}$, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 3-10 membered heterocyclyl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{gg}$ substituents can be joined to form =O or =S, wherein n is 0, 1, or 2, and $R^{aa}$, $R^{bb}$, $R^{cc}$, $R^{dd}$, $R^{ee}$, $R^f$, $R^{gg}$ and $R^{hh}$ are defined herein.

As used herein, each of $R^{aa}$, $R^{bb}$, $R^{cc}$, $R^{dd}$, $R^{ee}$, $R^{ff}$ and $R^{hh}$ at each occurrence is independently selected from hydrogen, $C_{1-6}$ alkyl, $C_{1-6}$ haloalkyl, $C_{2-6}$ alkenyl, $C_{2-6}$ alkynyl, $C_{3-6}$ cycloalkyl, 4-6 membered heterocyclyl, $C_{6-10}$ aryl, and 5-10 membered heteroaryl, or $R^{bb}$ and $R^{cc}$, $R^f$ and $R^{hh}$, $R^{ff}$ and one of $R^{bb}$ and $R^{cc}$, or $R^{hh}$ and one of $R^{bb}$ and $R^{cc}$, are joined to form a 4-6 membered heterocyclyl or 5-10 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups.

As used herein, $R^{gg}$ at each occurrence is independently selected from halo (e.g., F), nitro, cyano, hydroxy, $NH_2$, $N(H)(C_{1-6}$ alkyl), $N(C_{1-6}$ alkyl)($C_{1-6}$ alkyl), $N(H)(C_{3-6}$ cycloalkyl), $N(C_{1-6}$ alkyl)($C_{3-6}$ cycloalkyl), $N(C_{3-6}$ cycloalkyl)($C_{3-6}$ cycloalkyl), 0-$C_{1-6}$ alkyl, $C_{1-6}$ alkyl, $C_{1-6}$ haloalkyl, 0-$C_{1-6}$ haloalkyl, $C_{3-6}$ cycloalkyl optionally substituted with 1-5 substituents independently selected from halogen, $C_{1-4}$ alkyl, and $C_{3-6}$ cycloalkyl, 0-$C_{3-6}$ cycloalkyl optionally substituted with 1-5 substituents independently selected from halogen, $C_{1-4}$ alkyl, and $C_{3-6}$ cycloalkyl, 4-6 membered heterocyclyl optionally substituted with 1-3 substituents independently selected from halogen, oxo, $C_{1-4}$ alkyl, and $C_{3-6}$ cycloalkyl, $C_{6-10}$ aryl optionally substituted with 1-5 substituents independently selected from halogen, cyano, $C_{1-4}$ alkyl, and $C_{3-6}$ cycloalkyl, and 5-10 membered heteroaryl optionally substituted with 1-5 substituents independently selected from halogen, cyano, $C_{1-4}$ alkyl, and $C_{3-6}$ cycloalkyl, or two geminal $R^{gg}$ substituents can be joined to form =O or =S.

As used herein, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is a $C_{3-8}$ cycloalkyl group. In another embodiment, the cycloalkyl group is a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclopentenyl, and cyclohexenyl.

As used herein, the term "optionally substituted cycloalkyl" as used by itself or as part of another group means that the cycloalkyl as defined above is either unsubstituted or substituted with one or more (e.g., one, two, or three) substituents each independently chosen from, e.g., halo (e.g., F), oxo, nitro, cyano, $OR^a$, $CO_2R^a$, $OCO_2R^a$, $OSO_2NR^bR^c$, $SO_3R^a$, $OSO_3R^a$, $OS(O)_nR^{aa}$, $NR^bR^c$, $C(=O)NR^bR^c$, $OC(=O)NR^bR^c$, $SO_2NR^bR^c$, $OC(=O)R^d$, $C(=O)R^d$, $S(O)_nR^c$, $C(=NR^f)NR^bR^c$, alkyl, cycloalkyl, alkenyl, alkynyl, aryl, heteroaryl, and heterocyclyl, wherein each alkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein. In one embodiment, the optionally substituted cycloalkyl is substituted with three substituents. In one embodiment, the optionally substituted cycloalkyl is substituted with two substituents. In another embodiment, the optionally substituted cycloalkyl is substituted with one substituent.

As used herein, the term "alkenyl" as used by itself or as part of another group refers to an alkyl group as defined above containing one, two or three carbon-to-carbon double bonds. In one embodiment, the alkenyl group is a $C_{2-6}$ alkenyl group. In another embodiment, the alkenyl group is a $C_{24}$ alkenyl group. Non-limiting exemplary alkenyl groups include ethenyl, propenyl, isopropenyl, butenyl, sec-butenyl, pentenyl, and hexenyl.

As used herein, the term "optionally substituted alkenyl" as used herein by itself or as part of another group means the alkenyl as defined above is either unsubstituted or substituted with one or more (e.g., one, two, or three) substituents each independently chosen from, e.g., halo (e.g., F), oxo, nitro, cyano, $OR^a$, $CO_2R^a$, $OCO_2R^a$, $OSO_2NR^bR^c$, $SO_3R^a$, $OSO_3R^a$, $OS(O)_nR^c$, $NR^bR^c$, $C(=O)NR^bR^c$, $OC(=O)NR^bR^c$, $SO_2NR^bR^c$, $OC(=O)R^d$, $C(=O)R^d$, $S(O)_nR^c$, $C(=NR^f)NR^bR^e$, alkyl, cycloalkyl, alkenyl, alkynyl, aryl, heteroaryl, and heterocyclyl, wherein each alkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein.

As used herein, the term "alkynyl" as used by itself or as part of another group refers to an alkyl group as defined above containing one to three carbon-to-carbon triple bonds. In one embodiment, the alkynyl has one carbon-carbon triple bond. In one embodiment, the alkynyl group is a $C_{2-6}$ alkynyl group. In another embodiment, the alkynyl group is a $C_{24}$ alkynyl group. Non-limiting exemplary alkynyl groups include ethynyl, propynyl, butynyl, 2-butynyl, pentynyl, and hexynyl groups.

As used herein, the term "optionally substituted alkynyl" as used herein by itself or as part of another group means the alkynyl as defined above is either unsubstituted or substituted with one or more (e.g., one, two, or three) substituents each independently chosen from, e.g., halo (e.g., F), oxo, nitro, cyano, $OR^a$, $CO_2R^a$, $OCO_2R^a$, $OSO_2NR^bR^c$, $SO_3R^a$, $OSO_3R^a$, $OS(O)_nR^c$, $NR^bR^c$, $C(=O)NR^bR^c$, $OC(=O)NR^bR^c$, $SO_2NR^bR^c$, $OC(=O)R^d$, $C(=O)R^d$, $S(O)_nR^c$, $C(=NR^f)NR^bR$, alkyl, cycloalkyl, alkenyl, alkynyl, aryl, heteroaryl, and heterocyclyl, wherein each alkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein.

As used herein, the term "haloalkyl" as used by itself or as part of another group refers to an alkyl substituted with one or more fluorine, chlorine, bromine and/or iodine atoms. In preferred embodiments, the haloalkyl is an alkyl group substituted with one, two, or three fluorine atoms. In one embodiment, the haloalkyl group is a $C_{1-10}$ haloalkyl group. In one embodiment, the haloalkyl group is a $C_{1-6}$ haloalkyl group. In one embodiment, the haloalkyl group is a $C_{1-4}$ haloalkyl group.

As used herein, the term "optionally substituted haloalkyl" as used by itself or as part of another group refers to an optionally substituted alkyl substituted with one or more fluorine, chlorine, bromine and/or iodine atoms.

As used herein, the term "alkoxy" as used by itself or as part of another group refers to a radical of the formula $OR^{a1}$, wherein $R^{a1}$ is an alkyl. As used herein, the term "optionally substituted alkoxy" refers to a radical of the formula $OR^{a1}$, wherein $R^{a1}$ is an optionally substituted alkyl.

As used herein, the term "cycloalkoxy" as used by itself or as part of another group refers to a radical of the formula OR a, wherein $R^{a1}$ is a cycloalkyl. As used herein, the term "optionally substituted cycloalkoxy" refers to a radical of the formula $OR^{a1}$, wherein $R^{a1}$ is an optionally substituted cycloalkyl.

As used herein, the term "aryl" as used by itself or as part of another group refers to a monocyclic, bicyclic or tricyclic aromatic ring system having from six to fourteen carbon atoms (i.e., $C_{6-14}$ aryl). In one embodiment, the aryl group is a $C_{6-12}$ aryl. In one embodiment, the aryl group is chosen from phenyl and naphthyl. In one embodiment, the aryl group is naphthyl.

As used herein, the term "optionally substituted aryl" as used by itself or as part of another group means that the aryl as defined above is either unsubstituted or substituted with one to five substituents each independently chosen from, e.g., halo (e.g., F), nitro, cyano, $OR^a$, $CO_2R^a$, $OCO_2R^a$, $OSO_2NR^bR^c$, $SO_3a$, $OSO_3R^a$, $OS(O)_nR^c$, $NR^bR^c$, $C(=O)NR^bR^c$, $OC(=O)NR^bR^c$, $SO_2NR^bR^c$, $OC(=O)R^d$, $C(=O)R^d$, $S(O)_nR^e$, $C(=NR^f)NR^bR^c$, alkyl, cycloalkyl, alkenyl, alkynyl, aryl, heteroaryl, and heterocyclyl, wherein each alkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein; or two of the substituents are joined to form an optionally substituted cycloalkyl or optionally substituted heterocyclyl ring fused to the aryl.

As used herein, the term "heteroaryl" or "heteroaromatic" refers to monocyclic, bicyclic or tricyclic aromatic ring systems having 5 to 14 ring atoms (i.e., a 5- to 14-membered heteroaryl) and 1, 2, 3, or 4 heteroatoms independently chosen from oxygen, nitrogen and sulfur. In one embodiment, the heteroaryl has three heteroatoms, e.g., three nitrogen atoms. In another embodiment, the heteroaryl has two heteroatoms, e.g., two nitrogen atoms, one nitrogen and one oxygen, or one nitrogen and one sulfur. In another embodiment, the heteroaryl has one heteroatom, e.g., one nitrogen. In one embodiment, the heteroaryl has 5 ring atoms, e.g., pyrazolyl. In another embodiment, the heteroaryl has 6 ring atoms, e.g., pyridyl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, O-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). In one embodiment, the heteroaryl is a bicyclic heteroaryl having 8 to 10 ring atoms, e.g., a bicyclic heteroaryl having 1, 2, or 3 nitrogen ring atoms, such as quinolyl. As used herein, the term "heteroaryl" is also meant to include possible N-oxides.

As used herein, the term "optionally substituted heteroaryl" as used by itself or as part of another group means that the heteroaryl as defined above is either unsubstituted or substituted with one or more (e.g., 1, 2, 3, 4, or 5) substituents each independently chosen from, e.g., halo (e.g., F), nitro, cyano, $OR^a$, $CO_2R^a$, $OCO_2R^a$, $OSO_2NR^bR^c$, $SO_3R^a$, $OSO_3R^a$, $OS(O)_nR^e$, $NR^bR^c$, $C(=O)NR^bR^c$, $OC(=O)NR^bR^c$, $SO_2NR^bR^c$, $OC(=O)R^d$, $C(=O)R^d$, $S(O)_nR^e$, $C(=NR^f)NR^bR^c$, alkyl, cycloalkyl, alkenyl, alkynyl, aryl, heteroaryl, and heterocyclyl, wherein each alkyl, cycloalkyl, alkenyl, alkynyl, aryl, heteroaryl, and heterocyclyl is further optionally substituted with 1-5 $R^1$, wherein n is 0, 1, or 2, and $R^a$, $R^b$, $R^c$, $R^d$, $R^e$, $R^f$ and $R^1$ are defined herein; or two of the substituents are joined to form an optionally substituted cycloalkyl or optionally substituted heterocyclyl ring fused to the heteroaryl.

As used herein, the term "heterocycle" or "heterocyclyl" as used by itself or as part of another group refers to saturated and partially unsaturated (e.g., containing one or two double bonds) cyclic groups containing one, two, or three rings having from three to fourteen ring members (i.e., a 3- to 14-membered heterocycle) and at least one heteroatom. Each heteroatom is independently selected from the group consisting of oxygen, sulfur, including sulfoxide and sulfone, and/or nitrogen atoms, which can be quaternized. The term "heterocyclyl" is meant to include cyclic ureido groups such as imidazolidinyl-2-one, cyclic amide groups such as β-lactam, γ-lactam, δ-lactam and ε-lactam, and cyclic carbamate groups such as oxazolidinyl-2-one. In one embodiment, the heterocyclyl group is a 4-, 5-, 6-, 7- or 8-membered cyclic group containing one ring and one or two oxygen and/or nitrogen atoms. In one embodiment, the heterocyclyl group is a 5- or 6-membered cyclic group containing one ring and one or two nitrogen atoms. In one embodiment, the heterocyclyl group is an 8-, 9-, 10-, 11-, or 12-membered cyclic group containing two rings and one or two nitrogen atoms. The heterocyclyl can be optionally linked to the rest of the molecule through a carbon or nitrogen atom.

As used herein, the term "optionally substituted heterocyclyl" as used herein by itself or part of another group means the heterocyclyl as defined above is either unsubstituted or substituted with one or more (e.g., 1, 2, 3, 4, or 5) substituents each independently chosen from, e.g., halo (e.g., F), oxo, nitro, cyano, $OR^a$, $CO_2R^a$, $OCO_2R^a$, $OSO_2NR^bR^c$, $SO_3R^a$, $OSO_3R^a$, $OS(O)_nR^e$, $NR^bR^c$, $C(=O)NR^bR^c$, $OC(=O)NR^bR^c$, $SO_2NR^bR^c$, $OC(=O)R^d$, $C(=O)R^d$, $S(O)_nR^e$, $C(=NR^f)NR^bR^c$, alkyl, cycloalkyl, alkenyl, alkynyl, aryl, heteroaryl, and heterocyclyl, wherein each alkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein; or two of the substituents are joined to form an optionally substituted aryl or optionally substituted heteroaryl ring fused to the heterocyclyl. Substitution may occur on any available carbon or nitrogen atom, and may form a spirocycle.

As used herein, the term "alkanoyl" as used by itself or as part of another group refers to a radical of the formula $C(=O)—R^{d1}$, wherein $R^{d1}$ is an alkyl group. As used herein, the term "optionally substituted alkanoyl" as used by itself or as part of another group refers to $C(=O)—R^{d1}$, wherein $R^{d1}$ is an optionally substituted alkyl group.

As used herein, the term "cycloalkanoyl" as used by itself or as part of another group refers to a radical of the formula $C(=O)R^{d1}$, wherein $R^{d1}$ is a cycloalkyl group. As used herein, the term "optionally substituted cycloalkanoyl" as used by itself or as part of another group refers to $C(=O)R^{d1}$, wherein $R^{d1}$ is an optionally substituted cycloalkyl group.

As used herein, the term "salt" includes both internal salt and external salt. In some embodiments, the salt is an internal salt, i.e., containing a zwitterion structure. In some embodiments, the salt is an external salt. In some embodiments, the external salt is a pharmaceutically acceptable salt having a suitable counter ion. Suitable counterions for pharmaceutical use are known in the art.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

The term "inhibition", "inhibiting", "inhibit," or "inhibitor" refer to the ability of a compound to reduce, slow, halt or prevent activity of a particular biological process (e.g., activity of ACC enzyme in a cell relative to vehicle).

The term "subject" (alternatively referred to herein as "patient") as used herein, refers to an animal, preferably a mammal, most preferably a human, who has been the object of treatment, observation or experiment.

EXAMPLES

The various starting materials, intermediates, and compounds of the preferred embodiments can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses. In NMR spectroscopy, some signals may be characterized as singlets if the fine splitting is not fully resolved. Exemplary embodiments of steps for performing the synthesis of products described herein are described in greater detail infra.

Example 1. Synthesis of 1'-(4,8-dimethoxy-2-naphthoyl)-7-isopropylspiro[isochroman-3,4'-piperidin]-1-one

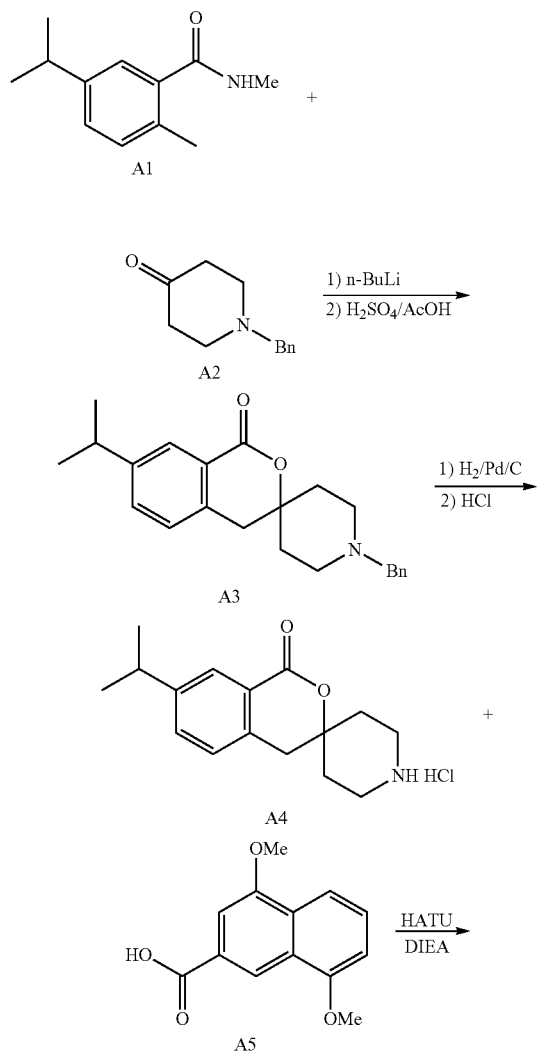

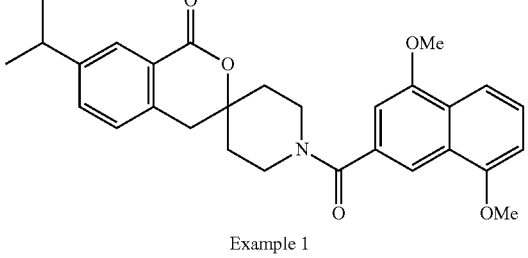

Example 1

Compound A4, 7-Isopropyl-1-oxospiro[isochroman-3,4'-piperidin]-1'-ium chloride (31 mg, 0.106 mmole), which was prepared from compounds A1 and A2 following procedures similar to those reported in the literature, (See e.g., Yamato M. et al. "Synthesis and Structure-Activity Relationship of Spiro[isochromanpiperidine] Analogues for Inhibition of Histamine Release," J. Med. Chem. 24:194-198 (1981), 4,8-dimethoxy-2-naphthoic acid (26 mg, 0.107 mmole), DIEA (45 µL, 0.265 mmole), and HATU (47 mg, 0.125 mmole) were mixed in DMF (0.75 mL) and left at room temperature for 4 hr. The reaction was diluted with ethyl acetate (5 mL) and washed with 0.1 N HCl (2X), saturated NaHCO$_3$(2X), and brine. The crude product after evaporation of the organic solvent was chromatographed on TLC eluting with ethyl acetate/dichlormethane (1:10). The product band was collected and washed with ethyl acetate to give Example 1 as a white powder after drying in vacuo (45 mg). NMR (CDCl$_3$) δ: 7.99 (d, 1H); 7.89 (s, 1H); 7.84 (d, 1H); 7.45 (m, 2H); 7.19 (d, 1H); 6.91 (s, 1H); 6.90 (d, 1H); 4.4-4.6 (br, 1H); 4.04 (s, 3H); 4.00 (s, 3H); 3.45-3.9 (br, 3H); 3.06 (S, 2H); 2.98 (pent, 1H); 1.55-2.15 (br, 4H); 1.29 (d, 6H).

Example 2. Synthesis of 1'-(4,8-dimethoxyquinoline-2-carbonyl)-7-isopropylspiro[isochroman-3,4'-piperidin]-1-one

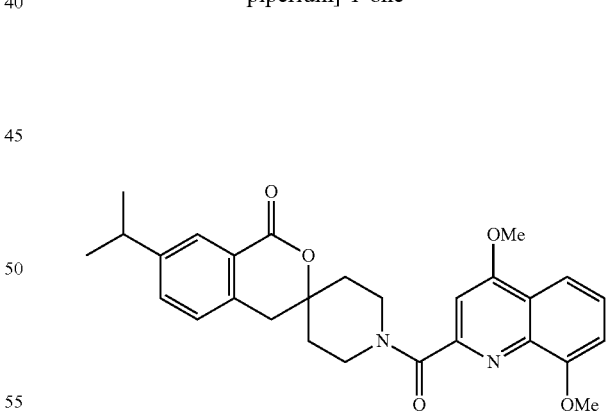

Example 2 was prepared in a similar procedure as Example 1, using 7-isopropyl-1-oxospiro[isochroman-3,4'-piperidin]-1'-ium chloride and 4,8-dimethoxyquinoline-2-carboxylic acid. Preparatory TLC was eluted with MeOH/ethyl acetate (1:10). NMR (CDCl$_3$) δ: 7.99 (d, 1H); 7.80 (d, 1H); 7.50 (t, 1H); 7.45 (dd, 1H); 7.20 (d, 1H); 7.19 (s, 1H); 7.11 (d, 1H); 4.56 (br d, 1H); 4.15 (br, 1H); 4.12 (s, 3H); 4.06 (s, 3H); 3.69 (br t, 1H); 3.48 (br t, 1H); 3.08 (s, 2H); 2.98 (pent, 1H); 2.11-2.14 (m, 2H); 1.97-2.00 (m, 2H); 1.29 (d, 6H).

Example 3. Synthesis of 1'-(4,8-dimethoxy-2-naphthoyl)-7-ethylspiro[isochroman-3,4'-piperidin]-1-one

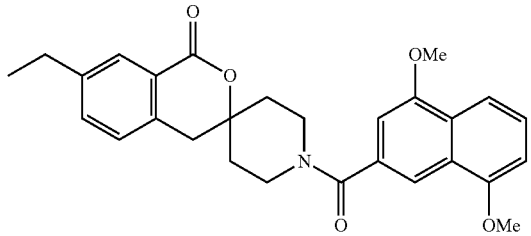 [SMILES: CCc1ccc2c(c1)C(=O)OC1(CCN(C(=O)c3cc(OC)c4cccc(OC)c4c3)CC1)C2]

Example 3 was prepared in a similar procedure as Example 1, using 7-ethyl-1-oxospiro[isochroman-3,4'-piperidin]-1'-ium chloride and 4,8-dimethoxy-2-naphthoic acid. Preparatory TLC was eluted with ethyl acetate/dichloromethane (1:1). NMR (CDCl$_3$) δ: 7.96 (br s, 1H); 7.89 (br s, 1H); 7.84 (d, 1H); 7.46 (d, 1H); 7.42 (t, 1H); 7.18 (d, 1H); 6.91 (s, 1H); 6.905 (d, 1H); 4.4-4.7 (br, 1H); 4.04 (s, 3H); 4.01 (s, 3H); 3.45-3.95 (br, 3H); 3.06 (s, 2H); 2.71 (q, 2H); 1.5-2.2 (br, 4H); 1.28 (t, 3H).

Example 4. Synthesis of 1'-(4,8-dimethoxyquinoline-2-carbonyl)-7-ethylspiro[isochroman-3,4'-piperidin]-1-one

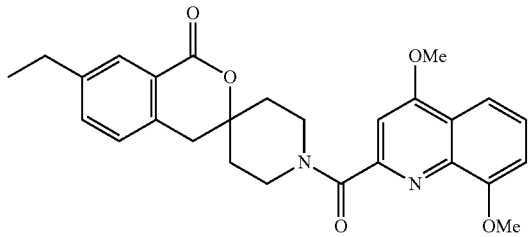

Example 4 was prepared in a similar procedure as Example 1, using 7-ethyl-1-oxospiro[isochroman-3,4'-piperidin]-1'-ium chloride and 4,8-dimethoxyquinoline-2-carboxylic acid. Preparatory TLC was eluted with MeOH/ethyl acetate/(1:10). NMR (CDCl$_3$) δ: 7.96 (br s, 1H); 7.80 (d, 1H); 7.51 (t, 1H); 7.42 (dd, 1H); 7.20 (d, 1H); 7.19 (s, 1H); 7.11 (d, 1H); 4.55-4.58 (m, 1H); 4.05-4.15 (m, 1H); 4.12 (s, 3H); 4.06 (s, 3H); 3.68 (m, 1H); 3.48 (m, 1H); 3.08 (s, 2H); 2.72 (q, 2H); 2.1-2.2 (m, 2H); 1.9-2.0 (m, 2H); 1.28 (t, 3H).

Example 5. Synthesis of 1'-(4,8-dimethoxy-2-naphthoyl)-7-((1-methyl-1H-pyrazol-5-yl)amino)spiro[isochroman-3,4'-piperidin]-1-one

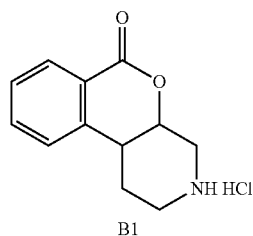 HNO$_3$ →

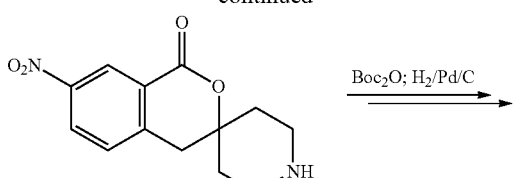 Boc$_2$O; H$_2$/Pd/C →

B2

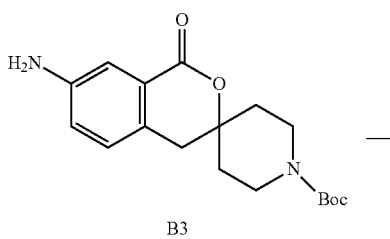

B3

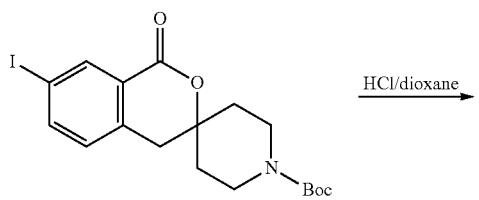 HCl/dioxane →

B4

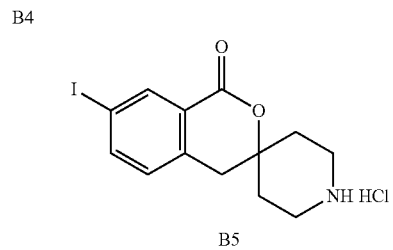

B5

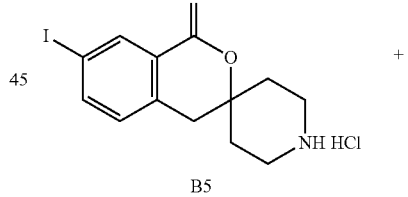 +

B5

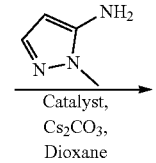

B6

B7 Catalyst, Cs$_2$CO$_3$, Dioxane →

53
-continued

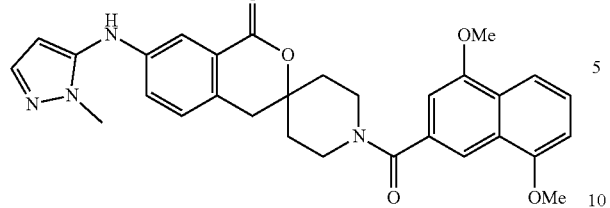

Example 5

Step 1. tert-Butyl 7-nitro-1-oxospiro[isochroman-3,4'-piperidine]-1'-carboxylate

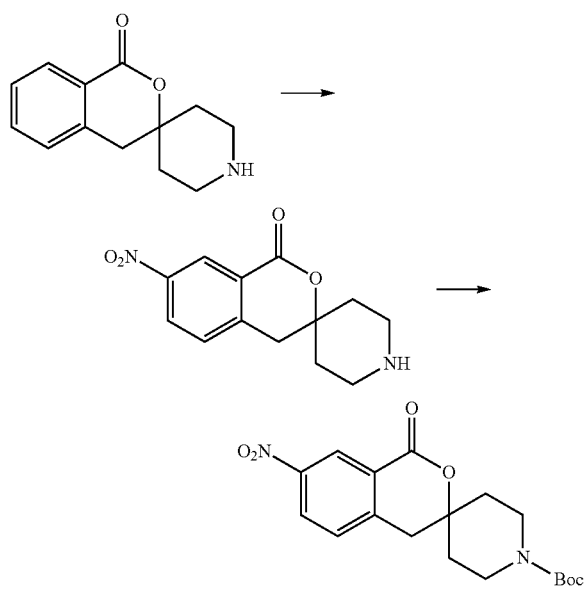

Spiro [isochroman-3,4'-piperidin]-1-one hydrochloride (25.3g), available by using literature reported method (See e.g., Yamato M. et al. "Synthesis and Structure-Activity Relationship of Spiro[isochromanpiperidine] Analogues for Inhibition of Histamine Release," J. Med. Chem. 24:194-198 (1981), was mixed with $H_2SO_4$ (60 mL) at 0° C., and followed by a solution of $KNO_3$ (12g) in $H_2SO_4$ (50 mL) below 0° C. The reaction was poured into ice water one hour later, and the pH was adjusted to 10 by addition of $Na_2CO_3$. The mixture was treated with $Boc_2O$ and extracted with EA (200 mL), the EA phase was separated and evaporated to give tert-butyl 7-nitro-1-oxospiro[isochroman-3,4'-piperidine]-1'-carboxylate (20g) as a light yellow solid.

Step 2. tert-Butyl 7-amino-1-oxospiro[isochroman-3,4'-piperidine]-1'-carboxylate

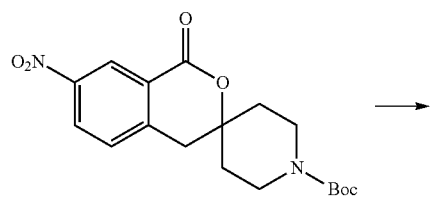

54
-continued

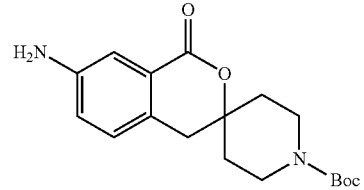

A mixture of tert-butyl 7-nitro-1-oxospiro[isochroman-3,4'-piperidine]-1'-carboxylate (20.3g) and Pd/C(1 g) in MeOH (150 mL) was treated with $H_2$ (50 psi) for 3h. The reaction mixture was filtered and the filtrate was evaporated to give tert-butyl 7-amino-1-oxospiro[isochroman-3,4'-piperidine]-1'-carboxylate (15g) as a light yellow solid.

Step 3. tert-Butyl 7-iodo-1-oxospiro[isochroman-3,4'-piperidine]-1'-carboxylate)

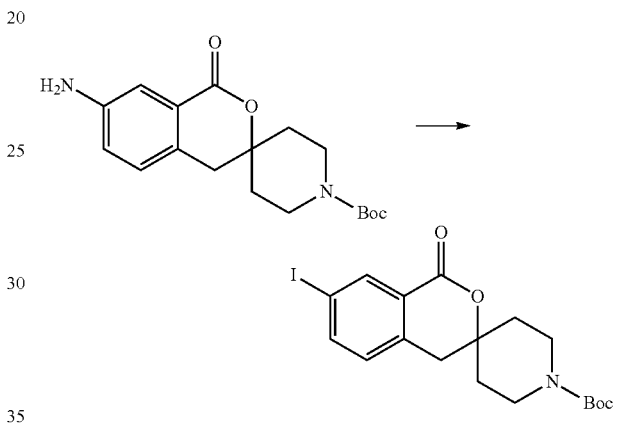

To a mixture of tert-butyl 7-amino-1-oxospiro[isochroman-3,4'-piperidine]-1'-carboxylate (2.6g), NaI (2.6g), $I_2$ (1.3 g) and CuI (0.5g) in acetonitrile (20 mL) was added, t-butylnitrile (2.4g) at 50° C. dropwise. One hour later, the reaction mixture was poured into a $Na_2S_2O_3$ solution and extracted with MTBE (30 mL), the organic phase was dried and passed through a silica pad, evaporated to give tert-butyl 7-iodo-1-oxospiro[isochroman-3,4'-piperidine]-1'-carboxylate as a light yellow oil (2.2g). NMR (CDCl$_3$) δ: 8.44 (s, 1H); 7.89 (d, 1H); 7.01 (d, 1H); 3.9 (br, 2H); 3.3 (br, 2H); 2.98 (s, 2H); 1.94 (br, 2H); 1.65 (br, 2H); 1.49 (s, 9H).

Step 4. Preparation of compound B5 (7-iodo-1-oxospiro [isochroman-3,4'-piperidin]-1'-ium chloride).

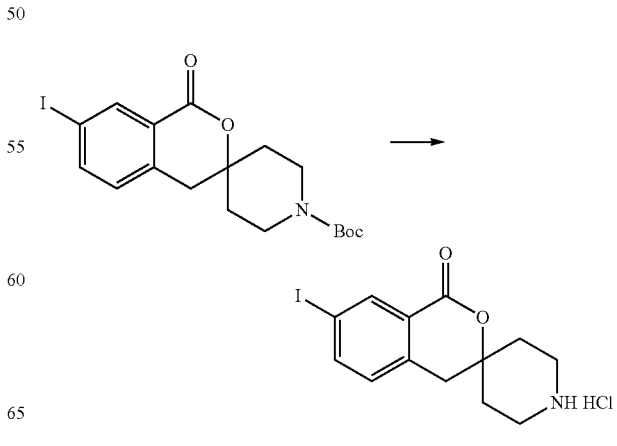

tert-Butyl 7-iodo-1-oxospiro[isochroman-3,4'-piperidine]-1'-carboxylate (500 mg) was treated with 4 N HCl/dioxane (5 mL) for a few minutes. The excess reagent and solvent was removed by rotavap and the residue dried in vacuo to give B5 as a white solid. Analytical HPLC indicated complete disappearance of the starting material, with one dominant product peak. This material was used without further purification.

Step 5. Preparation of compound B7 (1'-(4,8-dimethoxy-2-naphthoyl)-7-iodospiro [isochroman-3,4'-piperidin]-1-one).

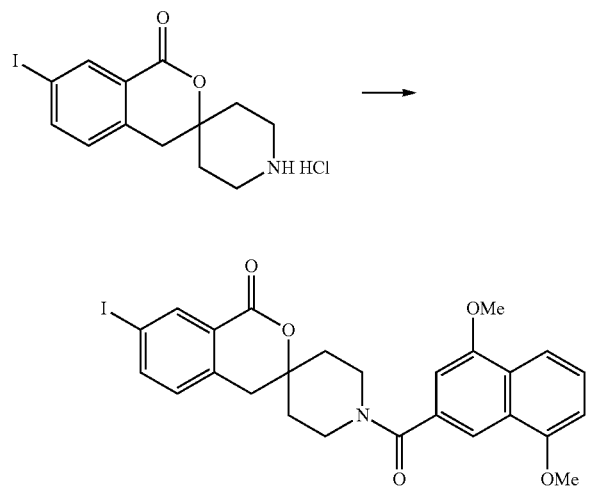

7-Iodo-1-oxospiro[isochroman-3,4'-piperidin]-1'-ium chloride (48 mg, 0.126 mmole), 4,8-dimethoxy-2-naphthoic acid (31 mg, 1.07 eq.) was coupled in the same procedure as for Example 1. The crude product was used without purification in the next step.

Step 6. Preparation of Example 5.

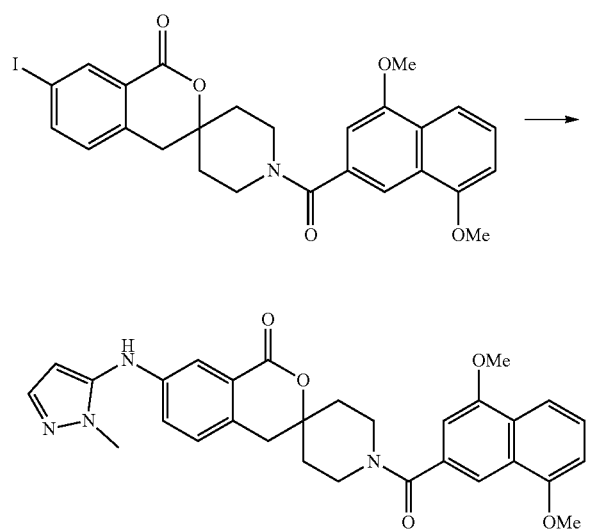

Compound B7, 1'-(4,8-dimethoxy-2-naphthoyl)-7-iodospiro[isochroman-3,4'-piperidin]-1-one (~78 mg, 0.13 mmol), was mixed with 1-methyl-1H-pyrazol-5-amine (15 mg, 1.07 eq.), $Cs_2CO_3$ (60 mg, 1.3 eq.), BrettPhose Pd G1 Methyl t-Butyl Ether Adduct (Aldrich, 8 mg, 0.07 eq.) in DMF (1.5 mL) and heated to 90-100C for 4 hr. The reaction mixture was filtered, and crude product after evaporation was loaded onto Preparatory TLC plate (2 plates) and eluted with MeOH/ethyl acetate (1:10) to give Example 5 as white powder after drying. NMR ($CDCl_3$) δ: 7.90 (s, 1H); 7.84 (d, 1H); 7.57 (m, 2H); 7.47 (t, 1H); 7.17 (d, 1H); 7.07 (d, 1H); 6.86 (d, 1H); 6.85 (s, 1H); 6.20 (br s, 1H): 6.1 (br s, 1H); 4.51 (m, 1H); 4.0-4.1 (br, 1H); 4.07 (s, 3H); 4.05 (s, 3H); 3.6-3.9 (br, 2H); 3.85 (s, 3H); 3.02 (s, 2H); 2.2 (br, 1H); 1.7-2.16 (br, 3H).

Example 6. Synthesis of 1'-(4,8-dimethoxyquinoline-2-carbonyl)-7-((1-methyl-1H-pyrazol-5-yl)amino)spiro[isochroman-3,4'-piperidin]-1-one

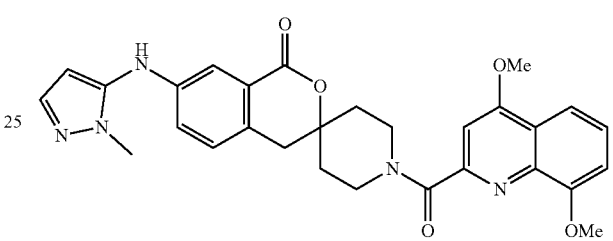

Example 6 was prepared using the same procedure as Example 5, substituting 4,8-dimethoxy-2-naphthoic acid with 4,8-dimethoxyquinoline-2-carboxylic acid. NMR ($CDCl_3$) δ: 7.80 (d, 1H); 7.5 (m, 3H); 7.19 (s, 1H); 7.12 (s, 1H); 7.12 (t, 1H); 6.95 (dd, 1H); 6.11 (d, 1H); 5.74 (br, 1H); 4.52-4.59 (m, 1H); 4.05-4.15 (m, 1H); 4.12 (s, 3H); 4.04 (s, 3H); 3.77 (s, 3H); 3.60-3.72 (m, 1H); 3.39-3.50 (m, 1H); 3.04 (s, 2H); 1.9-2.15 (m, 4H).

Example 7. Synthesis of 7-isopropyl-1'-(2-methyl-1H-benzo[d]imidazole-6-carbonyl)spiro[isochroman-3,4'-piperidin]-1-one

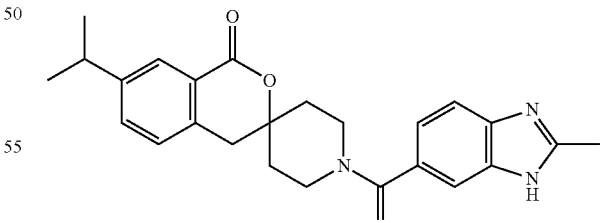

Example 7 was prepared using the same procedure as Example 1, substituting 4,8-dimethoxy-2-naphthoic acid with 2-methyl-1H-benzo[d]imidazole-6-carboxylic acid. NMR ($CDCl_3$) δ: 8.00 (s, 1H); 7.52 (s, 1H); 7.46 (d, 1H); 7.44 (d, 1H); 7.24 (d, 1H); 7.20 (d, 1H); 4.52 (br, 1H); 3.7 (br, 1H); 3.5 (br, 2H); 3.05 (s, 2H); 2.99 (hep, 1H); 2.54 (s, 3H); 1.6-2.2 (br, 4H); 1.28 (d, 6H).

Example 8. Synthesis of 1'-(1H-indazole-5-carbonyl)-7-isopropylspiro[isochroman-3,4'-piperidin]-1-one

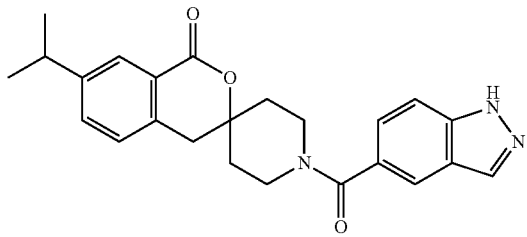 [SMILES: CC(C)c1ccc2c(c1)C(=O)OC1(CCN(C(=O)c3ccc4[nH]ncc4c3)CC1)C2]

Example 8 was prepared using the same procedure as Example 1, substituting 4,8-dimethoxy-2-naphthoic acid with 1H-indazole-5-carboxylic acid. NMR (CDCl$_3$) δ: 8.13 (s, 1H); 7.99 (s, 1H); 7.88 (s, 1H); 7.5 (d, 1H); 7.48 (d, 1H); 7.45 (d, 1H); 7.19 (d, 1H); 4.55 (br, 1H); 3.4-3.7 (br, 3H); 3.04 (s, 2H); 2.99 (hept, 1H); 1.9-2.1 (br, 2H); 1.7-1.8 (br, 2H); 1.29 (d, 6H).

Example 9. Synthesis of 7-isopropyl-1'-(1H-pyrrolo[3,2-b]pyridine-2-carbonyl)-spiro[isochroman-3,4'-piperidin]-1-one

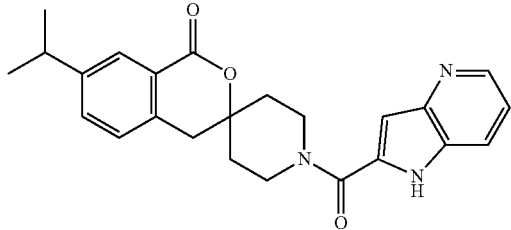 [SMILES: CC(C)c1ccc2c(c1)C(=O)OC1(CCN(C(=O)c3cc4ncccc4[nH]3)CC1)C2]

Example 9 was prepared using the same procedure as Example 1, substituting 4,8-dimethoxy-2-naphthoic acid with 1H-pyrrolo[3,2-b]pyridine-2-carboxylic acid. NMR (CDCl$_3$) δ: 9.89 (s, 1H); 8.54 (d, 1H); 8.02 (s, 1H); 7.76 (d, 1H); 7.47 (d, 1H); 7.21 (d, 1H); 7.20 (dd, 1H); 6.99 (s, 1H); 4.59 (br, 2H); 3.4-4.0 (br, 2H); 3.08 (s, 2H); 3.00 (hept, 1H); 2.16 (br, 2H); 1.83 (br, 2H); 1.30 (d, 6H).

Example 10. Synthesis of 1'-(1H-indazole-6-carbonyl)-7-isopropylspiro-[isochroman-3,4'-piperidin]-1-one

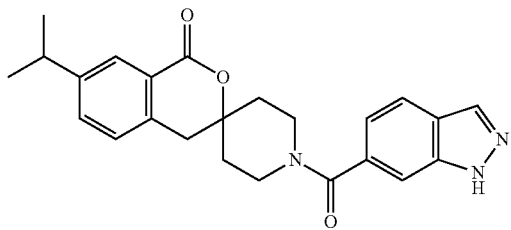 [SMILES: CC(C)c1ccc2c(c1)C(=O)OC1(CCN(C(=O)c3ccc4cn[nH]c4c3)CC1)C2]

Example 10 was prepared using the same procedure as Example 1, substituting 4,8-dimethoxy-2-naphthoic acid with 1H-indazole-6-carboxylic acid. NMR (CDCl$_3$) δ: 10.76 (s, 1H); 8.13 (s, 1H); 7.99 (s, 1H); 7.80 (d, 1H); 7.62 (s, 1H); 7.45 (d, 1H); 7.20 (d, 1H); 7.19 (d, 1H); 4.6 (br, 1H); 3.64 (br, 2H); 3.46 (br, 1H); 3.03 (s, 2H); 3.0 (hept, 1H); 1.6-2.2 (m, 4H); 1.29 (d, 6H).

Example 11. Synthesis of 7-isopropyl-1'-(6-methoxyquinoline-3-carbonyl)spiro [isochroman-3,4'-piperidin]-1-one

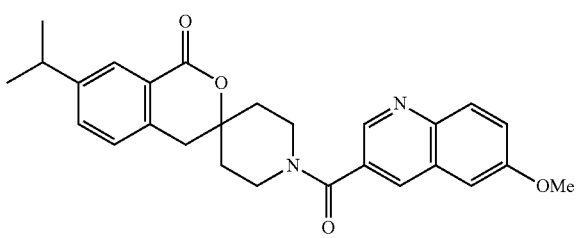 [SMILES: COc1ccc2ncc(C(=O)N3CCC4(CC3)Cc3ccc(C(C)C)cc3C(=O)O4)cc2c1]

Example 11 was prepared using the same procedure as Example 1, substituting 4,8-dimethoxy-2-naphthoic acid with 6-methoxyquinoline-3-carboxylic acid. NMR (CDCl$_3$) δ: 8.81 (s, 1H); 8.15 (s, 1H); 8.03 (d, 1H); 7.99 (s, 1H); 7.46 (d, 1H); 7.45 (d, 1H); 7.20 (d, 1H); 7.10 (s, 1H); 4.6 (br, 1H); 3.98 (s, 3H); 3.7 (br, 2H); 3.5 (br, 1H); 3.05 (s, 2H); 2.99 (hept, 1H); 1.6-2.2 (br, 4H); 1.30 (d, 6H).

Example 12. Synthesis of 1'-(2-ethyl-1H-benzo[d]imidazole-6-carbonyl)-7-isopropylspiro[isochroman-3,4'-piperidin]-1-one

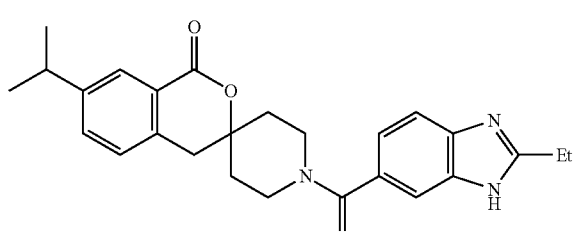

Example 12 was prepared using the same procedure as Example 1, substituting 4,8-dimethoxy-2-naphthoic acid with 2-ethyl-1H-benzo[d]imidazole-6-carboxylic acid. NMR (CDCl$_3$) δ: 7.99 (s, 1H); 7.55 (br, 1H); 7.48 (br, 1H); 7.46 (d, 1H); 7.24 (d, 1H); 7.19 (d, 1H); 4.55 (br, 1H); 3.7 (br, 1H); 3.5 (br, 2H); 3.04 (s, 2H); 2.99 (hept, 1H); 2.90 (q, 2H); 1.6-2.18 (br, 4H); 1.42 (t, 3H); 1.27 (d, 6H).

Example 13. Synthesis of 7-isopropyl-1'-(3-methyl-2-oxo-2,3-dihydro-1H-benzo [d]imidazole-5-carbonyl)spiro[isochroman-3,4'-piperidin]-1-one

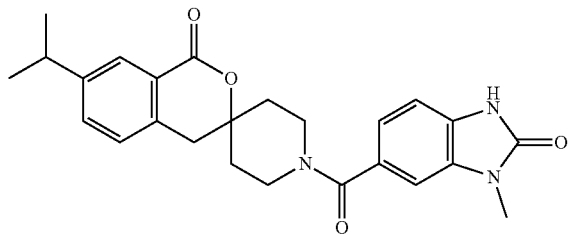 [SMILES: CC(C)c1ccc2c(c1)C(=O)OC1(CCN(C(=O)c3ccc4[nH]c(=O)n(C)c4c3)CC1)C2]

Example 13 was prepared using the same procedure as Example 1, substituting 4,8-dimethoxy-2-naphthoic acid with 3-methyl-2-oxo-2,3-dihydro-1H-benzo[d]imidazole-5-carboxylic acid. NMR (CDCl₃) δ: 9.19 (s, 1H); 8.0 (s, 1H); 7.45 (d, 1H); 7.05-7.2 (m, 4H); 4.53 (br, 1H); 3.58 (br, 3H); 3.46 (s, 3H); 3.06 (s, 2H); 2.99 (hept, 1H); 2.02 (br, 2H); 1.72 (br, 2H); 1.3 (d, 6H).

Example 14. Synthesis of methyl 5-(1'-(4,8-dimethoxyquinoline-2-carbonyl)-1-oxospiro[isochroman-3,4'-piperidin]-7-yl)nicotinate

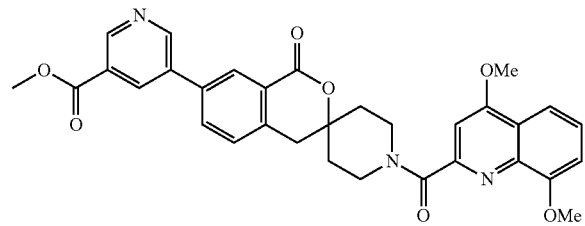 [SMILES: COC(=O)c1cncc(-c2ccc3c(c2)C(=O)OC2(CCN(C(=O)c4cc(OC)c5cccc(OC)c5n4)CC2)C3)c1]

Step 1. Preparation of tert-butyl 7-(5-(methoxycarbonyl) pyridin-3-yl)-1-oxospiro[isochroman-3,4'-piperidine]-1'-carboxylate.

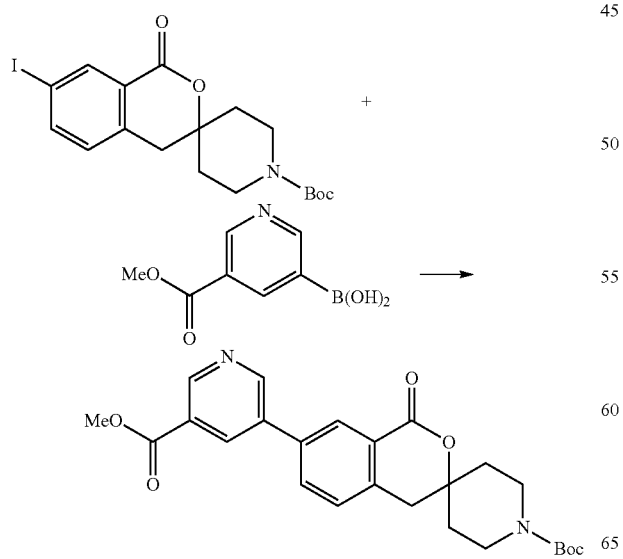

To a seal tube was added tert-butyl 7-iodo-1-oxospiro [isochroman-3,4'-piperidine]-1'-carboxylate (2.2 g, 4.96 mmol), 5-(methoxycarbonyl)pyridin-3-yl)boronic acid (2.0g, 11 mmol), NaHCO₃ (2.2 g, 26 mmol), Pd(PPh₃)₄(50 mg) in a mixture of solvents (toluene/water/methanol: 10 ml/1 ml/3 ml). This was heated for 2 hr at 90° C. After evaporation of the solvents, the residue was purified by silica column to give tert-butyl 7-(5-(methoxycarbonyl)pyridin-3-yl)-1-oxospiro[isochroman-3,4'-piperidine]-1'-carboxylate as white solid. NMR (CDCl3) δ: 9.26 (s, 1H); 9.07 (s, 1H); 8.55 (d, 1H); 8.42 (s, 1H); 7.86 (d, 1H); 7.42 (d, 1H); 4.03 (s, 3H); 3.85-3.98 (br, 2H); 3.3-3.44 (br, 2H); 3.11 (s, 2H); 1.95-2.04 (br, 2H); 1.65-1.76 (br, 2H); 1.44 (s, 9H).

Step 2. Methyl 5-(1-oxospiro[isochroman-3,4'-piperidin]-7-yl)nicotinate hydrochloride.

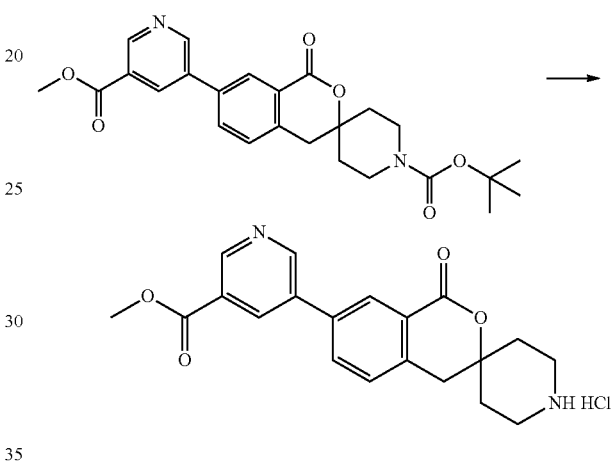

tert-Butyl 7-(5-(methoxycarbonyl)pyridin-3-yl)-1-oxospiro[isochroman-3,4'-piperidine]-1'-carboxylate (1.7g) was dissolved in ethyl acetate(15 mL) and treated with 4N HCl in EA(10 mL) at rt for a few minutes. The reaction was evaporated solvent to give methyl 5-(1-oxospiro[isochroman-3,4'-piperidin]-7-yl)nicotinate hydrochloride as a yellow solid (1.6 g).

Step 3. Methyl 5-(1'-(4,8-dimethoxyquinoline-2-carbonyl)-1-oxospiro[isochroman-3,4'-piperidin]-7-yl)nicotinate.

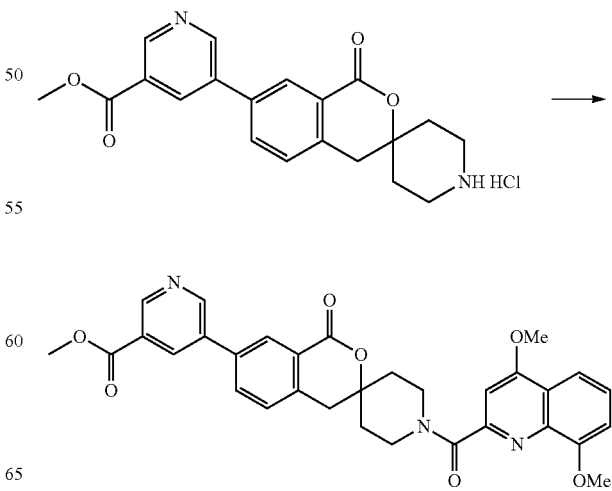

To a solution of 4,8-dimethoxyquinoline-2-carboxylic acid (0.233g) in DCM (10 mL) was added oxalyl chloride (1 mL, excess) at room temperature, and the resulting solution was stirred for 2 hr. Evaporation of solvent and excess reagent afforded the corresponding acid chloride as a solid.

The above solid was transferred to a mixture of methyl 5-(1-oxospiro[isochroman-3,4'-piperidin]-7-yl)nicotinate hydrochloride (0.4 g), triethylamine (2 mL) in DCM(10 mL) cooled at 0° C. The mixture was stirred for 30 min at room temperature, followed by addition of ice water. The aqueous layer was extracted with DCM(15 mL), and the combined organic phase was dried over MgSO4. The crude product after evaporation of solvent was purified by column purification to give methyl 5-(1'-(4,8-dimethoxyquinoline-2-carbonyl)-1-oxospiro[isochroman-3,4'-piperidin]-7-yl)nicotinate as an off-white solid. NMR (CDCl3) δ: 9.23 (s, 1H); 9.03 (s, 1H); 8.52 (s, 1H); 8.38 (s, 1H); 7.85 (d, 1H); 7.75 (d, 1H); 7.4-7.5 (m, 2H); 7.16 (s, 1H); 7.06 (d, 1H); 4.58 (br, 1H); 4.18 (br, 1H); 4.1 (s, 3H); 4.05 (s, 3H); 4.02 (s, 3H); 3.66 (br, 1H); 3.45 (br, 1H); 3.16 (s, 2H); 1.9-2.2 (br, 4H).

Example 15. Synthesis of 5-(1'-(4,8-dimethoxyquinoline-2-carbonyl)-1-oxospiro [isochroman-3,4'-piperidin]-7-yl)nicotinic acid

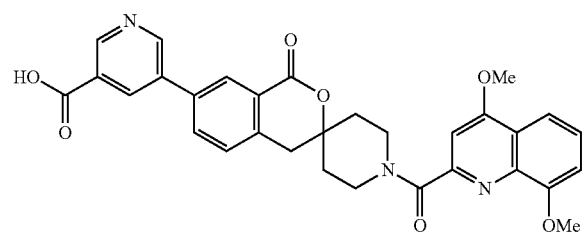 [SMILES: COc1cc(C(=O)N2CCC3(CC2)Cc2ccc(-c4cncc(C(=O)O)c4)cc2C(=O)O3)nc2c(OC)cccc12]

A solution of NaOH (2M, 0.5 mL) was added to a suspension of methyl 5-(1'-(4,8-dimethoxyquinoline-2-carbonyl)-1-oxospiro[isochroman-3,4'-piperidin]-7-yl)nicotinate (91 mg) in MeOH (5 mL). The mixture was heated to 50° C. for 30 min when all solid was dissolved. HPLC confirmed the complete conversion of starting material. The reaction mixture was neutralied with concentrated HCl (35%, 0.15 mL), and evaporated to dryness. The residue was treated again with 4N HCl/EA solution (2 mL) for 5 min. This mixture was evaporated under reduced pressure to dryness. The residue was taken up with MeOH/EA (1:1). The white solid was removed by filtration. Evaporation of solvent and lyophilization from acetonitrile/water afforded 5-(1'-(4,8-dimethoxyquinoline-2-carbonyl)-1-oxospiro[isochroman-3,4'-piperidin]-7-yl)nicotinic acid as white fluffy solid. NMR (DMSO-$d_6$) δ: 9.21 (d, 1H); 9.12 (d, 1H); 8.56 (t, 1H); 8.28 (d, 1H); 8.14 (dd, 1H); 7.76 (d, 1H); 7.63 (t, 1H); 7.62 (d, 1H); 7.41 (s, 1H); 7.40 (d, 1H); 4.28 (br, 1H); 4.17 (s, 3H); 4.02 (s, 3H); 3.3-3.6(br, 3H); 3.30 (s, 2H); 1.8-2.1 (br, 4H).

Example 16. Synthesis of 1-((ethoxycarbonyl)oxy) ethyl 5-(1'-(4,8-dimethoxy-quinoline-2-carbonyl)-1-oxospiro[isochroman-3,4'-piperidin]-7-yl)nicotinate

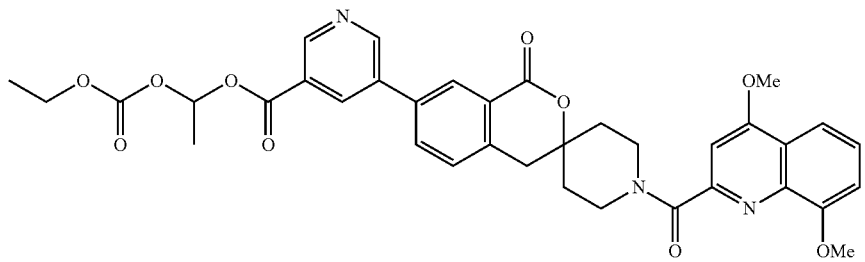 [SMILES: CCOC(=O)OC(C)OC(=O)c1cncc(-c2ccc3c(c2)C(=O)OC2(CCN(C(=O)c4cc(OC)c5cccc(OC)c5n4)CC2)C3)c1]

A suspension of 5-(1'-(4,8-dimethoxyquinoline-2-carbonyl)-1-oxospiro[isochroman-3,4'-piperidin]-7-yl)nicotinic acid (22 mg), 1-chloroethyl ethyl carbonate (30 μL), Cs$_2$CO$_3$ (126 mg), and KI (50 mg) in acetone (0.8 mL) was heated to 55° C. for 40 hr. PrepTLC (1:20 MeOH:EA) purification of the crude product afforded 1-((ethoxycarbonyl)oxy)ethyl 5-(1'-(4,8-dimethoxyquinoline-2-carbonyl)-1-oxospiro[isochroman-3,4'-piperidin]-7-yl)nicotinate as a fluffy solid after lyophilization. NMR (CDCl$_3$) δ: 9.27 (s, 1H); 9.07 (s, 1H); 8.53 (s, 1H); 8.40 (s, 1H); 7.86 (dd, 1H); 7.81 (d, 1H); 7.50 (t, 1H); 7.47 (d, 1H); 7.21 (s, 1H); 7.11 (d, 1H); 7.10 (q, 1H); 4.6(br, 1H); 4.29 (q, 2H); 4.2 (br, 1H); 4.12 (s, 3H); 4.05 (s, 3H); 3.7 (br, 1H); 3.5 (br, 1H); 3.21 (s, 2H); 1.9-2.2 (m, 4H); 1.74 (d, 3H); 1.36 (t, 3H).

Example 17. Synthesis of 2-(2-(2-methoxyethoxy)ethoxy)ethyl 5-(1'-(4,8-dimethoxyquinoline-2-carbonyl)-1-oxospiro[isochroman-3,4'-piperidin]-7-yl)nicotinate

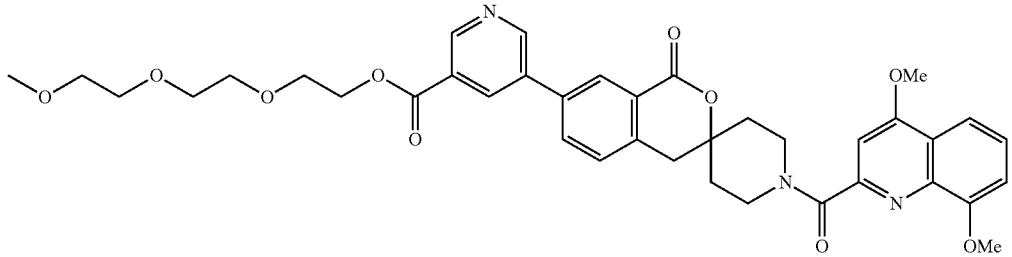 [SMILES: COCCOCCOCCOC(=O)c1cncc(-c2ccc3c(c2)C(=O)OC2(CCN(C(=O)c4cc(OC)c5cccc(OC)c5n4)CC2)C3)c1]

A suspension of 5-(1'-(4,8-dimethoxyquinoline-2-carbonyl)-1-oxospiro[isochroman-3,4'-piperidin]-7-yl)nicotinic acid (31 mg), 1-iodo-2-(2-(2-methoxyethoxy)ethoxy)ethane (75 µL), Cs$_2$CO$_3$ (136 mg), in acetone (1.0 mL) was heated to 55° C. for 18 hr. PrepTLC (1:10 MeOH:EA) purification of the crude product afforded 2-(2-(2-methoxyethoxy)ethoxy)ethyl 5-(1'-(4,8-dimethoxyquinoline-2-carbonyl)-1-oxospiro [isochroman-3,4'-piperidin]-7-yl)nicotinate as a fluffy solid after lyophilization. NMR (CDCl$_3$) δ: 9.28 (d, 1H); 9.06 (d, 1H); 8.56 (t, 1H); 8.41 (d, 1H); 7.87 (dd, 1H); 7.80 (d, 1H); 7.49 (t, 1H); 7.46 (d, 1H); 7.21 (s, 1H); 7.10 (d, 1H); 4.6 (br, 1H); 4.60 (t, 2H); 4.2 (br, 1H); 4.12 (s, 3H); 4.06 (s, 3H); 3.91 (t, 2H); 3.7 (m, 7H); 3.54 (t, 2H); 3.48 (br, 1H); 3.39 (s, 3H); 3.21 (s, 2H); 1.9-2.2 (m, 4H).

Example 18. Synthesis of 2-(2-methoxyethoxy)ethyl 5-(1'-(4,8-dimethoxy-quinoline-2-carbonyl)-1-oxospiro[isochroman-3,4'-piperidin]-7-yl)nicotinate

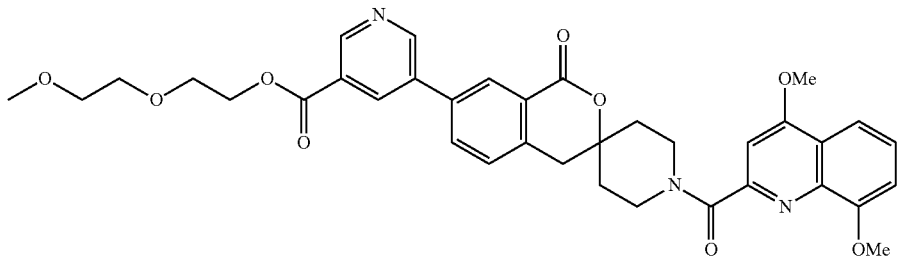 [SMILES: COCCOCCOC(=O)c1cncc(-c2ccc3c(c2)C(=O)OC2(CCN(C(=O)c4cc(OC)c5cccc(OC)c5n4)CC2)C3)c1]

A suspension of 5-(1'-(4,8-dimethoxyquinoline-2-carbonyl)-1-oxospiro[isochroman-3,4'-piperidin]-7-yl)nicotinic acid (28 mg, 0.05 mmol), 1-bromo-2-(2-methoxyethoxy)ethane (68 mg, 0.37 mmol), Cs$_2$CO$_3$ (140 mg, 0.43 mmol); KI (40 mg) was heated in acetone (0.8 mL) at 55 C for 24 hr. Solids were filtered off, and the filtrate was evaporated. The residue was dissolved in DCM (~1 mL) and loaded onto a prepTLC plate, eluting with MeOH:EA (3:20), to yield 2-(2-methoxyethoxy)ethyl 5-(1'-(4,8-dimethoxyquinoline-2-carbonyl)-1-oxospiro[isochroman-3,4'-piperidin]-7-yl)nicotinate as a white solid. NMR (CDCl$_3$) δ: 9.28 (d, 1H); 9.06 (d, 1H); 8.56 (t, 1H); 8.41 (d, 1H); 7.87 (dd, 1H); 7.80 (d, 1H); 7.49 (t, 1H); 7.46 (d, 1H); 7.21 (s, 1H); 7.10 (d, 1H); 4.6 (br, 1H); 4.60 (t, 2H); 4.2 (br, 1H); 4.12 (s, 3H); 4.06 (s, 3H); 3.91 (t, 2H); 3.74 (t, 2H); 3.5 (br, 1H); 3.61 (t, 2H); 3.48 (br, 1H); 3.41 (s, 3H); 3.20 (s, 2H); 1.9-2.2 (m, 4H).

Example 19. Synthesis of methyl 5-(1'-(8-cyclopropyl-4-methoxyquinoline-2-carbonyl)-1-oxospiro [isochroman-3,4'-piperidin]-7-yl)nicotinate

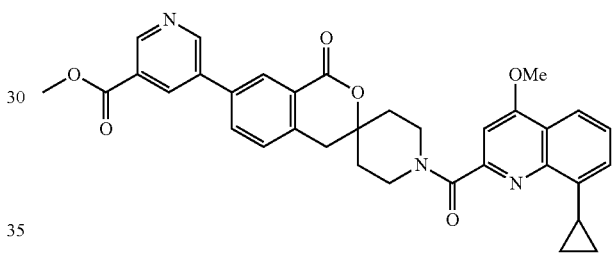

Example 19, methyl 5-(1'-(8-cyclopropyl-4-methoxyquinoline-2-carbonyl)-1-oxospiro [isochroman-3,4'-piperidin]-7-yl)nicotinate was prepared from methyl 5-(1-oxospiro [isochroman-3,4'-piperidin]-7-yl)nicotinate hydrochloride and 8-cyclopropyl-4-methoxyquinoline-2-carboxylic acid in the same way as Example 14. NMR (CDCl$_3$) δ: 9.26 (d, 1H); 9.08 (d, 1H); 8.56 (t, 1H); 8.42 (d, 1H); 8.04 (dd, 1H); 7.88 (dd, 1H); 7.48 (t, 1H); 7.46 (d, 1H); 7.22 (s, 1H); 7.20 (dd, 1H); 4.67 (br, 1H); 4.5 (br, 1H); 4.12 (s, 3H); 4.03 (s, 3H); 3.79 (m, 1H); 3.5 (m, 1H); 3.2 (s, 2H); 3.09 (m, 1H); 1.9-2.2 (m, 4H); 1.12 (br, 2H); 0.83 (br, 2H).

Example 20. Synthesis of 5-(1'-(8-cyclopropyl-4-methoxyquinoline-2-carbonyl)-1-oxospiro[isochroman-3,4'-piperidin]-7-yl)nicotinic acid

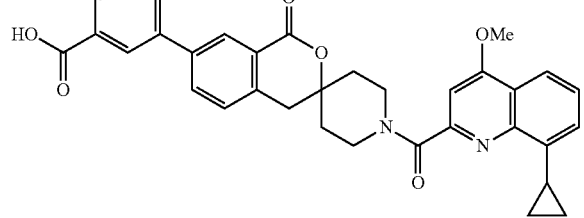

Example 20, 5-(1'-(8-cyclopropyl-4-methoxyquinoline-2-carbonyl)-1-oxospiro[isochroman-3,4'-piperidin]-7-yl)nicotinic acid was prepared from methyl 5-(1'-(8-cyclopropyl-4-methoxyquinoline-2-carbonyl)-1-oxospiro [isochroman-3,4'-piperidin]-7-yl)nicotinate in the same way as Example 15. NMR (DMSO-$d_6$) δ: 9.19 (s, 1H); 9.09 (s, 1H); 8.53 (s, 1H); 8.27 (s, 1H); 8.12 (d, 1H); 7.97 (d, 1H); 7.58 (d, 1H); 7.51 (t, 1H); 7.26 (d, 1H); 7.23 (s, 1H); 4.3 (br, 2H); 4.12 (s, 3H); 3.85 (br, 1H); 3.55 (br, 1H); 3.33 (s, 2H); 3.09 (m, 1H); 1.9 (m, 4H); 1.09 (m, 2H); 0.82 (m, 2H).

Example 21. Synthesis of methyl 5-(1'-(1-cyclopropyl-4-methoxy-3-methyl-1H-indole-6-carbonyl)-1-oxospiro[isochroman-3,4'-piperidin]-7-yl)nicotinate

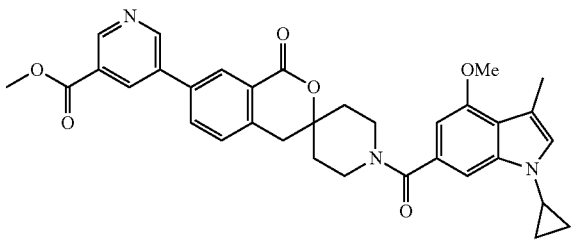 [SMILES: COC(=O)c1cncc(-c2ccc3c(c2)C(=O)OC2(CCN(C(=O)c4cc(OC)c5c(C)cn(C6CC6)c5c4)CC2)C3)c1]

Example 21, Methyl 5-(1'-(1-cyclopropyl-4-methoxy-3-methyl-1H-indole-6-carbonyl)-1-oxospiro[isochroman-3,4'-piperidin]-7-yl)nicotinate was prepared from methyl 5-(1-oxospiro[isochroman-3,4'-piperidin]-7-yl)nicotinate hydrochloride and 1-cyclopropyl-4-methoxy-3-methyl-1H-indole-6-carboxylic acid in the same way as Example 14. NMR (CDCl$_3$) δ: 9.24 (s, 1H); 9.04 (s, 1H); 8.54 (s, 1H); 8.40 (s, 1H); 7.85 (d, 1H); 7.42 (d, 1H); 7.22 (s, 1H); 6.82 (s, 1H); 6.50 (s, 1H); 4.02 (s, 3H); 3.90 (s, 3H); 3.6 (br, 4H); 3.23 (br, 1H); 3.14 (s, 2H); 2.42 (s, 3H); 1.6-2.1 (br, 4H); 1.0 (m, 4H).

Example 22. Synthesis of 5-(1'-(1-cyclopropyl-4-methoxy-3-methyl-1H-indole-6-carbonyl)-1-oxospiro[isochroman-3,4'-piperidin]-7-yl)nicotinic acid

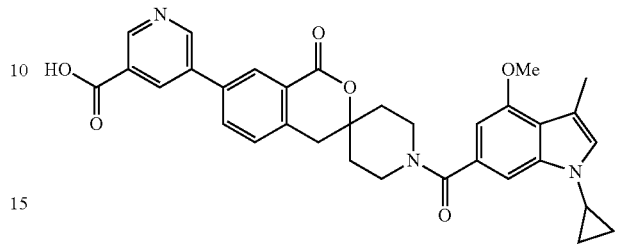

Example 22, 5-(1'-(1-cyclopropyl-4-methoxy-3-methyl-1H-indole-6-carbonyl)-1-oxospiro[isochroman-3,4'-piperidin]-7-yl)nicotinic acid was prepared from methyl 5-(1'-(1-cyclopropyl-4-methoxy-3-methyl-1H-indole-6-carbonyl)-1-oxospiro [isochroman-3,4'-piperidin]-7-yl)nicotinate in the same way as Example 15. NMR (DMSO-$d_6$) δ: 9.15 (s, 1H); 9.07 (s, 1H); 8.50 (s, 1H); 8.23 (s, 1H); 8.07 (d, 1H); 7.52 (d, 1H); 7.12 (s, 1H); 6.98 (s, 1H); 6.49 (s, 1H); 3.9 (br, 1H); 3.81 (s, 3H); 3.68 (br, 1H); 3.6 (br, 1H); 3.4 (br, 1H); 3.3 (br, 1H); 3.25 (s, 2H); 2.3 (s, 3H); 1.8 (br, 4H); 0.8-1.0 (m, 4H).

Formulation Example 1

Compounds of the present disclosure can be formulated into a topical formulation, such as lotions. Exemplary formulations are shown below:

| Formulation #1: (w/w %) | |
|---|---|
| Water | 60% |
| Diethylene Glycol Monoethyl Ether | 31% |
| Glycerin | 6% |
| Carbopol 980 | 3% |
| Active Ingredient (Example 6) | 0.1% or 0.05% |

| Formulation #2: (w/w %) | |
|---|---|
| Water | 61% |
| Diethylene Glycol Monoethyl Ether | 32% |
| Glycerin | 6% |
| Carbopol 980 | 3% |
| Active Ingredient (Example 6) | 0.1% or 0.05% |

Biological Example 1. Mouse ACC enzymatic activity assay

ACC protein was purified by taking advantage of the biotinylation in the carboxylase domain. Male C57BL/6J mice (Jackson Laboratory) at 8-12 weeks of age were euthanized by using CO$_2$ inhalation method and liver was immediately frozen on dry ice. To 100 mg liver was added 1 mL ice-cold tissue lysis buffer (20 mM Tris-HCl pH 7.5, 150 mM NaCl, 1 mM Na$_2$EDTA, 1 mM EGTA, 1% Triton, 2.5 mM sodium pyrophosphate, 1 mM 3-glycerophosphate, 1 mM Na$_3$VO$_4$, 1 μg/mL leupeptin, 1 tablet of protease inhibitor cocktail (Roche) per 10 mL lysis buffer) followed by homogenization on ice with Power Gen 125 homogenizer (Fisher Scientific). After 30 min incubation on ice, tissue lysate was passed through a 10 mL syringe with 18½ G needle for 10 times to shear DNA. The lysate was then subject to 17.5%-35% saturated ammonium sulfate precipitation by adding 880 mg ammonium sulfate powder (Sigma) to 10 mL liver lysate in 10 min with stirring on ice. Sample was centrifuged at 14,000 rpm (Eppendorf) at 4° C. for 10 min and supernatant was saved for further precipitation by adding 880 mg ammonium sulfate powder to 10 ml supernatant in 10 min with stirring on ice. Sample was centrifuged at 14,000 rpm at 4° C. for 10 min. Supernatant was discarded and pellet was dissolved in 10 mL sample buffer (100 mM Tris-HCl, pH 7.5, 1 mM EDTA, 0.1 mM DTT, 0.5 M NaCl, and 5% glycerol). The sample was then added with 1 mL of Strep Mag beads slurry (Genscript) and rotated at 4° C. for 1 hour. Supernatant was discarded and beads were washed with sample buffer for 3 times. Protein was then eluted by adding 10 mL of 2 mM biotin (Promega) prepared in sample buffer. The eluate was then dialyzed at 4° C. for 1 hour by using Slide-A-Lyzer™ Dialysis Cassettes 10K MWCO (Thermo Fisher Scientific) against 3 changes of 200 mL dialysis buffer (50 mM HEPES, pH 7.5, 0.1 mM DTT, 1.0 mM EDTA, and 10% glycerol). Total protein concentration was then quantitated by using BCA protein assay kit (Pierce).

For ACC enzymatic activity assay, 1 μL serial diluted compounds prepared in DMSO in duplicate were mixed with 8 μL dialyzed sample at 37° C. for 10 min. Ninety one L of reaction buffer (50 mM HEPES pH 7.5, 10 mM $MgCl_2$, 2.0 mM DTT, 0.5 mM acetyl-CoA, 4.0 mM ATP, 15 mM $^{13}C$-$NaHCO_3$, 0.75 mg/mL BSA, 0.5 mM sodium citrate) was added to the tube and mixed thoroughly. After incubation at 37° C. for 1 hour, 300 μl ice-cold quenching buffer (acetonitrile:methanol=1:1, 20 μM carbutamide as internal standard) was added to each tube and mixed well to terminate the reaction. Samples were centrifuged at 14,000 rpm for 10 min (Eppendorf) and supernatant was loaded onto LC-MS/MS for quantitation of malonyl-$^{13}C$-CoA (Gao et al., Journal of chromatography B, Analytical technologies in the biomedical and life sciences 853, 303-313 (2007)).

Biological Example 2. Human ACC Enzymatic Activity Assay

Human ACC enzymatic activity assays were performed by using purified human ACC1 and ACC2 proteins (BPS Bioscience). ACC1 and ACC2 proteins were diluted in 24.5 μL reaction buffer (50 mM HEPES pH 7.5, 10 mM $MgCl_2$, 2.0 mM DTT, 4.0 mM ATP, 15 mM $^{13}C$-$NaHCO_3$, 0.75 mg/mL BSA, 0.5 mM sodium citrate), and final concentrations of ACC1 and ACC2 were 0.4 μg/mL and 0.48 μg/mL. For each reaction, 0.5 μL of serial diluted compounds were prepared in DMSO in duplicate or triplicate and mixed with the above 24.5 μL reaction mixtures with ACC proteins at 37° C. for 10 min. Meanwhile, 25 μL of reaction buffer plus acetyl-CoA (final concentration: 5 μM) was prepared freshly and added to the above 25 μL mixture to initiate the reaction. After incubation at 37° C. for 1-2 hours, 100 μl ice-cold 10% TCA with malonyl-$^{13}C3$-CoA (final concentration: 40 nM, Sigma-Aldrich) was added to terminate the reaction. For LC-MS/MS analysis, 300 μL quenching buffer (acetonitrile:methanol=1:1, 20 μM carbutamide as internal standard) was added to each tube and mixed well. Samples were then centrifuged at 14,000 rpm for 10 min (Eppendorf) and supernatants were loaded onto LC-MS/MS for quantitation of malonyl-$^3C$-CoA (Gao et al., Journal of chromatography B, Analytical technologies in the biomedical and life sciences 853, 303-313 (2007)).

Biological Example 3. Quantitation of malonyl-CoA by LC-MS/MS

Shimadzu LC system was used for sample analysis consisting of system controller (Shimadzu CBM-20A), autosampler (Shimadzu SIL-20A), pump A and B (Shimadzu LC-20AD), column oven (Shimadzu CTO-20A), and analytical column (Phenomenex Gemini 5u C18 11A, 100×2 mm). LC was running at 200 μL/min in the binary gradient mode with mobile phase A (5 mM Ammonium Acetate and 5 mM DMBA in water (1,3-Dimethylbutylamine)) and B (methanol). The samples were analyzed on an AB Sciex QTrap4000 LC-MS/MS triple quadrupole mass spectrometer (Applied Biosystems). Malonyl-CoA and malonyl-13C-CoA were monitored in positive ion mode following MRM transitions at 854.2/347.1 and 855.1/246.1, respectively. The product and internal standard were coeluted to the mass spectrometer in 3 s with 50% $H_2O$, 25% MeCN, 25% acetone, and 5 mM ammonium acetate. Ion chromatograms were integrated using the Analyst 1.5.2 software. Peak area ratios were compared against a standard curve and final cellular concentration of malonyl-CoA or production rate of malonyl-13C-CoA was calculated as pmoles/mg protein per minute.

Biological Example 4. Effect of ACC Inhibitors on Cellular Levels of Malonyl-CoA in Human Sebocytes Human sebocytes (Celprogen) were grown in growth media (DMEM with 4.5 g/L glucose, 0.584 g/L L-glutamine (Sigma), 100 units/mL of penicillin and 100 μg/mL of streptomycin (Gibco), 10% fetal bovine serum (Gibco)) at 37° C. in a humidified water jacketed incubator (Forma Scientific) supplemented with 5% $CO_2$ till 100% confluency. Cells grown in 152 cm² cell culture dish (Corning) were trypsinized with 0.25% trypsin-EDTA (Gibco), centrifuged at 800 rpm for 10 min (Eppendorf) and resuspended in 4 mL growth media. To 1 μL serial diluted compounds in DMSO, 99 μL cells (around 0.5 million cells suspended in growth media) were added and mixed well followed by incubation in cell culture incubator for 30 min. Cells were then centrifuged at 800 rpm for 10 min and 70 μL 10% trichloroacetic acid was added to each well to lyse the cells and precipitate proteins. Cellular levels of malonyl-CoA were quantitated by LC-MS/MS.

Biological Example 5. Effect of ACC Inhibitors on Lipogenesis of Human Sebocytes Human sebocytes (Celprogen) were grown in collagen-coated 96-well culture microplate (White/Clear bottom, Corning BioCoat) with growth media till 100% confluency. Culture media was changed to growth media plus 100 μM arachidonic acid (Sigma) and 10 μM rosiglitazone (Tocris) with compounds prepared in DMSO (1:1000 dilution in growth media). Cells were treated with compounds for 96 hours with media containing compounds changed after 48 hours. Upon completion of treatment, cells were washed with 200 μL Phosphate Buffered Saline (PBS) and then fixed by adding 100 μL 4% formaldehyde (Sigma) and incubated at room temperature for 1 hour. Cells were then washed 3 times with PBS. Microplate was stained with 100 μL nile red solution prepared in PBS (2 mg/mL, 1:400 dilution) by incubating at 37° C. for 1 hour and then washed 3 times with PBS. The fluorescence was read at Ex 492 nm and Em 595 nm (TECAN SpectrofluorPlus). Effect of compounds on lipogenesis in sebocytes was calculated by % of DMSO vehicle control.

Biological Example 6. Effect of ACC Inhibitors on Proliferation of Human Sebocytes and Keratinocytes Human sebocytes (Celprogen) and keratinocytes (ATCC) were grown in 96-well culture microplate (Corning) with growth media to around 50% confluency. Media was changed to growth media mixed with serially diluted compounds in DMSO (1:1000 dilution). After treatment for 24 hours, media was changed to 100 µL phenol red free DMEM and cell numbers were quantitated by using Vybrant® MTT Cell Proliferation Assay Kit (Molecular Probes). Ten µL of 12 mM MTT stock solution was added to each well and the microplate was incubated at 37° C. for 4 hours. Then 100 µL of the SDS-HCl solution was added to each well and mixed thoroughly using a pipette. The microplate was incubated at 37° C. for 4 hours in a cell culture incubator. The microplate was mixed again using a pipette and absorbance was read at 570 nm (Dynex MRX$^e$ Magellan Biosciences). Effect of compounds on proliferation of human keratinocytes was calculated by % of DMSO vehicle control.

Biological Example 7. Effect of ACC Inhibitors on Lipogenesis of 3T3-L1 Adipocytes 3T3-L1 fibroblast cells (Zen-Bio) were grown in 96-well culture microplate (Corning) with growth media to around 90-100% confluency. Culture media was changed to differentiation media (growth media supplemented with 3-Isobutyl-1-Methylxanthine 500 µM, Dexamethasone 1 µM, insulin 10 µg/mL, and rosiglitazone 2 µM) plus serially diluted compounds prepared in DMSO (1:1000 dilution). After incubation for 2 days, media was changed to maintenance media (growth media supplemented with insulin 10 µg/mL) plus serially diluted compounds prepared in DMSO (1:1000 dilution) for around 1 week with media changed every 2 days. Upon completion of the treatment, culture media are discarded and 200 µL 0.01% SDS was added to each well and shaken for 1 hour to lyse the cells. Cell lysates were then transferred to 400 µL Folch's solution (chloroform: methanol=2:1) and mixed well. After centrifuge at 2,000 rpm for 20 min, 200 µL of the lower organic phase was transferred to a plate with 10 µL sample buffer (chloroform: Triton-100=3:1). Samples were blown dried under nitrogen and 200 µL triglyceride (TG) quantification reagent (Thermo Fisher Scientific) was added, mixed, and incubated at 37° C. for 30 min. TG concentration was determined by reading absorbance at 535 nm (Dynex MRX$^e$ Magellan Biosciences) and calculated from standard curve.

Biological Example 8. IHC Staining for Human Skin Tissue

Formalin-fixed, Paraffin-embedded slides of skin tissues from humans (Amsbio and ProSci) were baked at 65° C. for 30 min and deparaffinized/hydrated by incubating in three washes of xylene for 5 min each, two washes of 100% ethanol for 10 min each, two washes of 95% ethanol for 10 min each, and finally two washes in dH$_2$O for 5 min each. Slides were then boiled in 1 X antigen unmasking solution (Vector Laboratories) for 10 min. After washing in dH$_2$O, slides were stained with rabbit IgG isotype control antibody or rabbit monoclonal anti-ACC (18 µg/mL, 1:50 dilution, Cell Signaling Technology) at room temperature for 1 hour or at 4° C. overnight. Sections were then washed with wash buffer three times for 5 min each, Rabbit on Rodent HRP-Polymer (BioCare Medical) and DAB Quanto Chromagen and Substrate (Thermo Fisher Scientific) were used to develop the dark brown color to reveal the expression of ACC protein. Slides were counterstained with hematoxylin (RICCA Chemical), dehydrated, and sealed with coverslips by using VectaMount (Vector Laboratories). Pictures were taken by using Zeiss Primo Star and Nikon D800.

Analysis of images of IHC staining of human normal skin structure including layers of epidermis, dermis, and hypodermis in the above study of human skin, show that ACC proteins are abundantly and specifically expressed in sebaceous glands. This represents the first report on the localization of ACC proteins in human skin structure and it suggests that delivering ACC inhibitors to sebocytes, such as by topical administration of ACC inhibitors, will specifically inhibit ACCs in sebaceous gland, thus provides a powerful method of suppressing lipid accumulation and progression of diseases related to overproduction of lipids in sebocytes.

On the other hand, images of IHC staining of human normal skin show that ACC proteins are not abundantly expressed in keratinocytes of human normal skin.

Images of IHC staining of human in situ squamous cell carcinoma with adjacent skin tissue including sebaceous gland show that tumor cells in the squamous cell carcinoma, sebaceous gland and epidermal squamous cells are stained with comparable density of dark color, indicating abundant expression of ACC proteins.

Lastly, in images of IHC staining of human seborrheic keratosis, keratin layer is apparent in this disease and keratinocytes next to the keratin layer are stained with dark color (, indicating abundant expression of ACC proteins in keratinocytes in skin disease of keratosis.

Biological Example 9. Oil Red O Staining of Skin Tissue of Hamsters

Male hamsters at 8-12 weeks of age are treated with vehicle or compounds (0.01, 0.05, and 0.1% in vehicle) by applying the lotion onto the ears, vehicle on the left and compound on the right ear QD for 14 days (n=4). After euthanization by using CO$_2$ inhalation, ears are mounted on O.C.T. Compound and frozen sectioned at 5 µm (Leica CM1900). Slides are stained by using Oil Red O kit following the instruction from the provider (Abcam). Slides are counterstained with Modified Mayer's Hematoxylin (American MasterTech Scientific) and sealed with Aqua-Mount (Lerner Laboratories). Lipid droplet staining area is quantitated by using ImageJ (NIH).

Biological Example 10. In Vivo PK/PD Study in Mice and Hamsters

Tissue PK/PD. Male C57BL/6 mice at 8-12 weeks of age were treated with vehicle or compounds (0.01, 0.05, and 0.1% in vehicle) by applying the lotion on skin on the back (n=5). Animals were euthanized by using CO$_2$ inhalation at 10, 30, 60, 180, 360, and 1440 min post treatment and skin was taken for measuring levels of compounds and malonyl-CoA. Skin weighed around 100 mg is homogenized in 200 µL 10% TCA and centrifuged at 14,000 rpm for 10 min.

Supernatant (10 µL) was loaded to LC/MS for quantitation of compounds and malonyl-CoA.

Standard PK. Male catheterized CD-1 mice were treated with Compound 6 prepared in vehicle (5% DMSO+10% Solutol+85% PBS, PH=7.4) at doses of 1 mg/kg for IV (5 mL/kg) or 5 mg/kg for PO (10 mL/kg). Blood samples (20 VL) were collected at 0.083, 0.25, 0.5, 1, 2, 4, 8, and 24 hrs post dose and mixed with 60 VL 0.1 M sodium citrate. Upon extraction by using acetonitrile, blood concentrations of Compound 6 were quantitated by LC-MS/MS. PK parameters were calculated by using WinNonlin® 6.4.

Biological Example 11. PK Study in Mice for Compound Examples 14 and 15

Pharmacokinetic studies were carried out with male C57 mouse. Compounds (Example 14 and Example 15) were each formulated in 5% DMSO+10% Solutol HS 15+85% Saline, and dosed at 1 mpk for IV injection (5 mL/kg) and 10 mpk for oral gavage (10 mUkg). Plasma samples at various time points were quantitated with LC-MS. Data reported were average of three mice.

Tables 1 and 2 below show plasma concentrations (ng/mL) and PK parameters of Example 14 in male C57 mouse after 1 mpk IV injection and 10 mpk PO gavage, respectively. The plasma concentration (ng/mL) of the acid compound, Example 15, was also measured and reported below.

TABLE 1

Plasma Concentration (ng/mL) and PK Parameters of Example 14 in Male C57 Mouse after 1 mpk IV Injection

| | Example 14 | | Example 15 | |
|---|---|---|---|---|
| Time (h) | Mean | SD | Mean | SD |
| 0.08 | 1877 | 399 | 122 | 9 |
| 0.25 | 1085 | 199 | 161 | 22 |
| 0.50 | 521 | 153 | 107 | 12 |
| 1.00 | 199 | 126 | 55 | 16 |
| 2.00 | 30 | 41 | 16 | 12 |
| 4.00 | 4.4 | NA | 3.4 | 3.1 |
| 8.00 | BLQ | NA | 1.5 | 0.3 |
| 24.00 | BLQ | NA | BLQ | NA |
| PK Parameters | | | | |
| Cl (mL/min/kg) | 18.5 | | NA | |
| $T_{1/2}$ (h) | 0.32 | | NA | |
| MRT (h) | 0.41 | | NA | |
| Vd (L/kg) | 0.49 | | NA | |

TABLE 2

Plasma Concentration (ng/ml) and PK Parameters of Example 14 in Male C57 Mouse after 10 mpk PO Gavage

| | Example 14 | | Example 15 | |
|---|---|---|---|---|
| Time (h) | Mean | SD | Mean | SD |
| 0.25 | 3658 | 795 | 152 | 54 |
| 0.50 | 5966 | 4373 | 168 | 15 |
| 1.00 | 3156 | 1623 | 146 | 37 |
| 2.00 | 1006 | 551 | 84 | 17 |
| 4.00 | 345 | 207 | 43 | 8 |
| 8.00 | 125 | 64 | 23 | 6 |
| 24.00 | BLQ | NA | 2.1 | NA |
| PK Parameters | | | | |
| Cmax (ng/ml) | 6328 | | 185 | |
| Tmax(h) | 0.42 | | 0.58 | |

TABLE 2-continued

Plasma Concentration (ng/ml) and PK Parameters of Example 14 in Male C57 Mouse after 10 mpk PO Gavage

| | Example 14 | | Example 15 | |
|---|---|---|---|---|
| Time (h) | Mean | SD | Mean | SD |
| MRT (h) | 1.6 | | 3.1 | |
| F (%) | 88% | | NA | |

Tables 3 and 4 below show plasma concentrations (ng/mL) and PK parameters of Example 15 in male C57 mouse after 1 mpk IV injection and 10 mpk PO gavage, respectively.

TABLE 3

Plasma Concentration (ng/ml) and PK Parameters of Example 15 in Male C57 Mouse after 1 mpk IV Injection

| | Example 15 | |
|---|---|---|
| Time (h) | Mean | SD |
| 0.08 | 3009 | 1273 |
| 0.25 | 414 | 158 |
| 0.50 | 95 | 56 |
| 1.00 | 28 | 11 |
| 2.00 | 6.6 | 1 |
| 4.00 | BLQ | NA |
| 8.00 | BLQ | NA |
| 24.00 | BLQ | NA |
| PK Parameters | | |
| Cl (mL/min/kg) | 23.3 | |
| $T_{1/2}$ (h) | 0.29 | |
| MRT (h) | 0.11 | |
| Vd (L/kg) | 0.49 | |

TABLE 4

Plasma Concentration (ng/mL) and PK Parameters of Example 15 in Male C57 Mouse after 10 mpk PO Gavage

| | Example 15 | |
|---|---|---|
| Time (h) | Mean | SD |
| 0.25 | 164 | 116 |
| 0.50 | 99 | 30 |
| 1.00 | 63 | 26 |
| 2.00 | 11 | 3 |
| 4.00 | 3.2 | 2 |
| 8.00 | 2 | NA |
| 24.00 | BLQ | NA |
| PK Parameters | | |
| Cmax (ng/ml) | 164 | |
| Tmax(h) | 0.25 | |
| MRT (h) | 0.99 | |
| F (%) | 1.7% | |

Biological Example 12. Chronic Treatment with ACC Inhibitors for Reducing Liver Triglycerides in C57BL/6J Mice Male C57BL/6J mice (Jackson Laboratory) at around 9 weeks of age were treated with vehicle (0.5% methylcellulose or PEG400) or Example 14 (30 mg per kilogram body weight, dosing solution prepared in PEG400) and Example 20 (20 mg per kilogram body weight, dosing solution prepared in 0.5% methylcellulose) by oral gavage at ~9:00 am, once per day for 2 weeks. Concentrations of Example 14 and Example 20 were 15 mg/ml and 2 mg/ml, respectively. The dosing volumes of Example 14 and Example 20 were 2 ml per kilogram body weight and 10 ml per kilogram body weight, respectively. After 14-day treatment, animals were euthanized in $CO_2$ at 2 hours post dose and liver was frozen and kept on dry ice. Liver TG was measured by extracting lipids with chloroform:methanol 2:1 (v/v) followed by quantitation with Infinity™ Triglycerides Reagent (Thermo Scientific).

The results shown in FIG. 1 indicate that both Examples 14 and 20 reduced liver TG in C57BL/6J mice.

TABLE 5

Data for some Examples

| | IC50 (nM) | | | | | | | | |
|---|---|---|---|---|---|---|---|---|---|
| Example | EA-CoA hACC 1 | EA-CoA hACC 2 | EA-CoA mACC | Malonyl-CoA in Sebo | LG-3T3 Sebo | LG-Sebo | AP-Sebo | m-PK | PPB (h/m) % free |
| 1 | | | 3.7 | 41.5 | 1.3 | 10 | 93.3 | | |
| 2 | | | 2.4 | | 0.8 | 25 | 57.1 | Cl: 46.5 mL/min/kg $T_{1/2}$ 0.42 h F: 4.9% | 0.37%/ 0.28% |
| 3 | | | 3.4 | | 1.4 | | 44.4 | | |
| 4 | | | 11.3 | | 27.7 | | 148.3 | | |
| 5 | | | 0.37 | | | | | | |
| 6 | 36.2 | 31.2 | 0.34 | 47.4 | 21.9 | | 2.5 | Cl: 15.2 mL/min/kg $T_{1/2}$ 0.50 h F: 53% | 0.36%/ 0.73% |
| 7 | | | | 6146 | | | | | |
| 8 | | | | 442.1 | | | | | |
| 9 | | | | 713.7 | | | | | |
| 10 | | | | 675.9 | | | | | |
| 11 | | | | 142 | | | | | |
| 12 | | | | 3490 | | | | | |
| 13 | | | | 2437 | | | | | |
| 15 | 27.5 | 33 | | | | | | | |
| 19 | 1117 | 740.2 | | | | | | | |
| 20 | 148 | 152 | | | | | | | |
| 21 | 295.6 | 221.2 | | | | | | | |
| 22 | 23.9 | 11.1 | | | | | | | |

The data in Table 5 were obtained by following the methods disclosed in this application and/or those standard techniques known in the art. ACC enzyme activities were measured according to Biological Examples 1 and 2; Malonyl-CoA in sebocytes were measured according to Biological Example 4; Effect on lipogenesis of 3T3-L1 adipocytes were measured according to Biological Example 7; Effect on lipogenesis of sebocytes were measured according to Biological Example 5; Effect on proliferation of sebocytes were measured according to Biological Example 6; Mouse PK were measured according to Biological Example 10; and Plasma protein binding (human or mouse) were measured by standard technique.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A method of treating a disease or disorder in a subject in need thereof, the method comprising administering to the subject:
   (a) a therapeutically effective amount of a compound of Formula Ia, or a pharmaceutically acceptable salt thereof, or a pharmaceutical composition comprising the compound of Formula Ia, or a pharmaceutically acceptable salt thereof, and a pharmaceutically acceptable excipient; and
   (b) one or more additional agents in a therapeutically effective amount for inhibiting the one or more activities or treating the disease or disorder;
wherein the compound of Formula Ia is

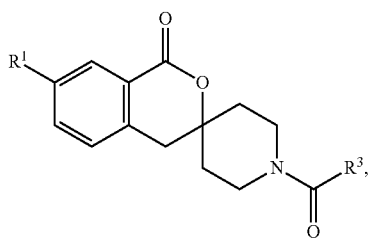

Formula Ia wherein
   $R^1$ is hydrogen, halogen, cyano, an optionally substituted $C_{1-6}$ alkyl, an optionally substituted $C_{3-6}$ cycloalkyl, an optionally substituted $C_{2-6}$ alkenyl, an optionally substituted $C_{2-6}$ alkynyl, an optionally substituted $C_{6-10}$ aryl, an optionally substituted 5-10 membered heteroaryl, an optionally substituted 4-6 membered heterocyclyl, $NR^{10}R^{11}$, $COOR^{12}$, $CONR^{13}R^{14}$, CN, $S(O)_nR^{15}$, or $OR^{16}$;
   $R^{10}$ and $R^{11}$ are each independently hydrogen, an optionally substituted $C_{1-6}$ alkyl, an optionally substituted $C_{3-6}$ cycloalkyl, an optionally substituted $C_{1-6}$ alkanoyl, an optionally substituted $C_{3-6}$ cycloalkanoyl, an optionally substituted $C_{6-10}$ aryl, an optionally substituted 5-10 membered heteroaryl, an optionally substituted 4-6 membered heterocyclyl, $COOR^{12}$, or $CONR^{13}R^{14}$;
   $R^{12}$, $R^{13}$ and $R^{14}$ are each independently hydrogen or an optionally substituted $C_{1-6}$ alkyl; n is 0, 1, or 2;
   $R^{15}$ is an optionally substituted $C_{1-6}$ alkyl, an optionally substituted $C_{3-6}$ cycloalkyl, or $N^{10}R^{11}$;
   $R^{16}$ is hydrogen, an optionally substituted $C_{1-6}$ alkyl, an optionally substituted $C_{3-6}$ cycloalkyl, an optionally substituted $C_{1-6}$ alkanoyl, an optionally substituted $C_{3-6}$ cycloalkanoyl, an optionally substituted $C_{6-10}$ aryl, an optionally substituted 5-10 membered heteroaryl, an optionally substituted 4-6 membered heterocyclyl or $CONR^{13}R^{14}$; and
   $R^3$ is an optionally substituted $C_{6-10}$ aryl or optionally substituted 5 to 10 membered heteroaryl, provided that when $R^1$ is hydrogen, then $R^3$ is not an optionally substituted phenyl;
wherein the disease or disorder is associated with aberrant sebocyte and/or keratinocyte activity, or the disease or disorder is a non-alcoholic fatty liver disease, obesity, and/or diabetes.

2. The method of claim 1, wherein the compound of Formula Ia has a Formula Ib,

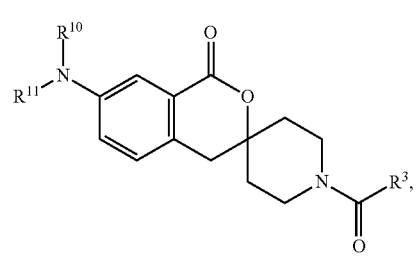

Formula Ib wherein one of $R^{10}$ and $R^{11}$ is an optionally substituted phenyl or optionally substituted 5 or 6 membered heteroaryl.

3. The method of claim 2, wherein one of $R^{10}$ and $R^{11}$ is a 5-membered heteroaryl having 2-4 ring nitrogen atoms, which is optionally substituted with 1 or 2 substituent independently chosen from halogen, cyano and $C_{1-4}$ alkyl.

4. The method of claim 2, wherein one of $R^{10}$ and $R^{11}$ is a pyrazolyl, triazolyl or tetrazolyl, each optionally substituted with a $C_{1-4}$ alkyl.

5. The method of claim 1, wherein $R^1$ is an optionally substituted 5 or 6 membered heteroaryl.

6. The method of claim 5, wherein $R^1$ is an optionally substituted tetrazolyl or pyridinyl.

7. The method of claim 5, wherein the compound of Formula Ia has a Formula Ic

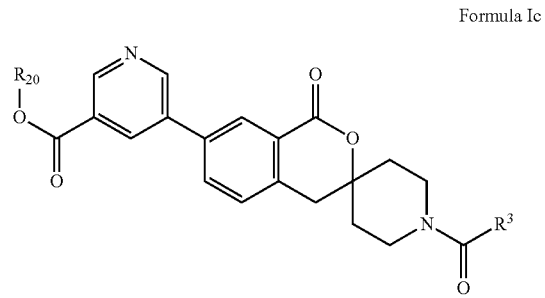

Formula Ic wherein $R^{20}$ is hydrogen, an optionally substituted alkyl, or an optionally substituted cycloalkyl.

8. The method of claim 7, or pharmaceutically acceptable salt thereof, wherein $R^{20}$ is

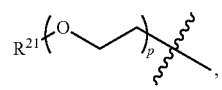

wherein p is an integer from 1-500, and $R^{21}$ is hydrogen, a $C_{1-4}$ alkyl or an oxygen protecting group.

9. The method of claim 7, wherein $R^{20}$ is

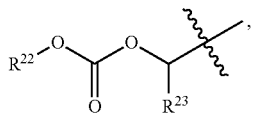

wherein $R^{22}$ is a $C_{1-4}$ alkyl, and $R^{23}$ is hydrogen or a $C_{1-4}$ alkyl.

10. The method of claim 1, wherein $R^3$ is selected from the group consisting of (i) $C_{6-10}$ aryl optionally substituted with 1-3 substituents independently chosen from halogen, hydroxyl, cyano, optionally substituted $C_{1-4}$ alkyl, optionally substituted $C_{1-4}$ alkoxy, optionally substituted $C_{3-6}$ cycloalkyl, and optionally substituted $C_{3-6}$ cycloalkoxy, and (ii) 8-10 membered bicyclic heteroaryl optionally substituted with one or more substituents independently chosen from halogen, cyano, hydroxyl, $C_{1-4}$ alkyl optionally substituted with 1-3 halogens, $C_{1-4}$ alkoxy optionally substituted with 1-3 halogens, $C_{3-6}$ cycloalkyl optionally substituted with 1-3 halogens, and $C_{3-6}$ cycloalkoxy optionally substituted with 1-3 halogens.

11. The method of claim 1, wherein the compound is 1'-(4,8-dimethoxy-2-naphthoyl)-7-isopropylspiro[isochroman-3,4'-piperidin]-1-one, 1'-(4,8-dimethoxyquinoline-2-carbonyl)-7-isopropylspiro[isochroman-3,4'-piperidin]-1-one, 1'-(4,8-dimethoxy-2-naphthoyl)-7-ethylspiro[isochroman-3,4'-piperidin]-1-one, 1'-(4,8-dimethoxyquinoline-2-carbonyl)-7-ethylspiro[isochroman-3,4'-piperidin]-1-one, 1'-(4,8-dimethoxy-2-naphthoyl)-7-((1-methyl-1H-pyrazol-5-yl)amino)spiro[isochroman-3,4'-piperidin]-1-one, 1'-(4,8-dimethoxyquinoline-2-carbonyl)-7-((1-methyl-1H-pyrazol-5-yl)amino)spiro[isochroman-3,4'-piperidin]-1-one, 7-isopropyl-1'-(2-methyl-1H-benzo[d]imidazole-6-carbonyl)spiro[isochroman-3,4'-piperidin]-1-one, 1'-(1H-indazole-5-carbonyl)-7-isopropylspiro[isochroman-3,4'-piperidin]-1-one, 7-isopropyl-1'-(1H-pyrrolo[3,2-b]pyridine-2-carbonyl)-spiro[isochroman-3,4'-piperidin]-1-one, 1'-(1H-indazole-6-carbonyl)-7-isopropylspiro-[isochroman-3,4'-piperidin]-1-one, 7-isopropyl-1'-(6-methoxyquinoline-3-carbonyl)spiro [isochroman-3,4'-piperidin]-1-one, 1'-(2-ethyl-1H-benzo[d]imidazole-6-carbonyl)-7-isopropylspiro [isochroman-3,4'-piperidin]-1-one, 7-isopropyl-1'-(3-methyl-2-oxo-2,3-dihydro-1H-benzo [d]imidazole-5-carbonyl)spiro[isochroman-3,4'-piperidin]-1-one, methyl 5-(1'-(4,8-dimethoxyquinoline-2-carbonyl)-1-oxospiro [isochroman-3, 4'-piperidin]-7-yl) nicotinate, 5-(1'-(4,8-dimethoxyquinoline-2-carbonyl)-1-oxospiro [isochroman-3,4'-piperidin]-7-yl)nicotinic acid, 1-((ethoxycarbonyl)oxy)ethyl 5-(1'-(4,8-dimethoxy-quinoline-2-carbonyl)-1-oxospiro[isochroman-3,4'-piperidin]-7-yl)nicotinate, 2-(2-(2-methoxyethoxy)ethoxy)ethyl 5-(1'-(4,8-dimethoxyquinoline-2-carbonyl)-1-oxospiro [isochroman-3, 4'-piperidin]-7-yl)nicotinate, 2-(2-methoxyethoxy)ethyl 5-(1'-(4,8-dimethoxy-quinoline-2-carbonyl)-1-oxospiro [isochroman-3, 4'-piperidin]-7-yl)nicotinate, methyl 5-(1'-(8-cyclopropyl-4-methoxyquinoline-2-carbonyl)-1-oxospiro[isochroman-3,4'-piperidin]-7-yl)nicotinate, 5-(1'-(8-cyclopropyl-4-methoxyquinoline-2-carbonyl)-1-oxospiro [isochroman-3, 4'-piperidin]-7-yl)nicotinic acid, methyl 5-(1'-(1-cyclopropyl-4-methoxy-3-methyl-1H-indole-6-carbonyl)-1-oxospiro[isochroman-3,4'-piperidin]-7-yl)nicotinate, or 5-(1'-(1-cyclopropyl-4-methoxy-3-methyl-1H-indole-6-carbonyl)-1-oxospiro[isochroman-3,4'-piperidin]-7-yl)nicotinic acid.

12. The method of claim 1, wherein the disease or disorder associated with aberrant sebocyte and/or keratinocyte activity is acne, seborrhea, sebaceous hyperplasia, seborrheic keratosis, actinic keratosis, sebaceous adenoma, sebaceous cyst, sebaceous carcinoma, squamous cell carcinoma, melanoma, phymatous rosacea, fibrofolliculomas in Birt-Hogg-Dube syndrome, or a combination thereof.

13. The method of claim 12, wherein the compound of Formula Ia, or pharmaceutically acceptable salt thereof, or the pharmaceutical composition is administered to the subject topically.

14. The method of claim 12, wherein the one or more additional agents are an antibiotic or retinoid.

15. The method of claim 1, wherein the non-alcoholic fatty liver disease is non-alcoholic steatohepatitis (NASH).

16. The method of claim 15, wherein the one or more additional agents are chosen from angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacyl glycerol O-acyltransferase 1 (DGAT1) inhibitors, dipeptidyl peptidase IV (DPPIV) inhibitors, farnesoid X receptor (FXR) agonists, galectin-3 inhibitors, glucagon-like peptide 1 (GLP1) agonists, glutathione precursors, hepatitis C virus NS3 protease inhibitors, HMG Co A reductase inhibitors, Iiβ-hydroxysteroid dehydrogenase (11β-HSD1) inhibitors, IL-1β antagonists, IL-6 antagonists, IL-10 agonists, IL-17 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPAR-alpha agonists, PPAR-gamma agonists, PPAR-delta agonists, Rho associated protein kinase 2 (ROCK2) inhibitors, sodium glucose transporter-2 (SGLT2) inhibitors, stearoyl CoA desaturase-1 inhibitors, thyroid hormone receptor 3 agonists, tumor necrosis factor alpha (TNF-alpha) ligand inhibitors, transglutaminase inhibitors, transglutaminase inhibitor precursors, and combinations thereof.

17. The method of claim 15, wherein the one or more additional agents are chosen from acetylsalicylic acid, alipogene tiparvovec, aramchol, atorvastatin, BLX-1002, cenicriviroc, cobiprostone, colesevelam, emricasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, PX-102, remogliflozin etabonate, SHP-626, solithromycin, tipelukast, TRX-318, ursodeoxycholic acid, VBY-376, and combinations thereof.

18. The method of claim 1, wherein the disease or disorder is obesity and/or diabetes.

19. The method of claim 18, wherein the one or more additional agents are chosen from angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacyl glycerol O-acyltransferase 1 (DGAT1) inhibitors, dipeptidyl peptidase IV (DPPIV) inhibitors, farnesoid X receptor (FXR) agonists, galectin-3 inhibitors, glucagon-like peptide 1 (GLP1) agonists, glutathione precursors, hepatitis C virus NS3 protease inhibitors, HMG Co A reductase inhibitors, Iβ-hydroxysteroid dehydrogenase (11β-HSD1) inhibitors, IL-1β antagonists, IL-6 antagonists, IL-10 agonists, IL-17 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPAR-alpha agonists, PPAR-gamma agonists, PPAR-delta agonists, Rho associated protein kinase 2 (ROCK2) inhibitors, sodium glucose transporter-2 (SGLT2) inhibitors, stearoyl CoA desaturase-1 inhibitors, thyroid hormone receptor 3 agonists, tumor necrosis factor alpha (TNF-alpha) ligand inhibitors, transglutaminase inhibitors, transglutaminase inhibitor precursors, and combinations thereof.

20. The method of claim 18, wherein the one or more additional agents are chosen from acetylsalicylic acid, alipogene tiparvovec, aramchol, atorvastatin, BLX-1002, cenicriviroc, cobiprostone, colesevelam, emricasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, PX-102, remogliflozin etabonate, SHP-626, solithromycin, tipelukast, TRX-318, ursodeoxycholic acid, VBY-376, and combinations thereof.

* * * * *